United States Patent
Miller et al.

(10) Patent No.: US 11,920,865 B2
(45) Date of Patent: *Mar. 5, 2024

(54) SYSTEMS AND METHODS FOR DRYING AND/OR CLEANING ENDOSCOPIC DEVICES

(71) Applicant: GI Scientific, LLC, Arlington, VA (US)

(72) Inventors: Scott Miller, Arlington, VA (US);
Frank Carter, Wormleysburg, PA (US);
Carl Gauger, Kansas City, MO (US)

(73) Assignee: GI Scientific, LLC, Arlington, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/226,492

(22) Filed: Jul. 26, 2023

(65) Prior Publication Data
US 2023/0375268 A1 Nov. 23, 2023

Related U.S. Application Data

(63) Continuation of application No. 17/739,146, filed on May 8, 2022, which is a continuation-in-part of
(Continued)

(51) Int. Cl.
*F26B 5/14* (2006.01)
*A61B 1/12* (2006.01)
(Continued)

(52) U.S. Cl.
CPC ............... *F26B 5/14* (2013.01); *A61B 1/122* (2013.01); *B08B 9/0436* (2013.01); *F26B 5/16* (2013.01); *B08B 2209/04* (2013.01)

(58) Field of Classification Search
CPC ......... A61B 1/121; A61B 1/122; A61B 1/125; A61B 1/126; A61B 90/70; A61B 2090/701; F26B 5/14; F26B 5/16
See application file for complete search history.

(56) References Cited

U.S. PATENT DOCUMENTS 8,490,235 B2 7/2013 Soetermans
8,566,995 B2 10/2013 Asano
(Continued)

FOREIGN PATENT DOCUMENTS

KR 20-0483788 Y1 6/2017

OTHER PUBLICATIONS

USPTO Office Action; U.S. Appl. No. 17/509,304; dated Jan. 13, 2022.

*Primary Examiner* — Laura C Guidotti
(74) *Attorney, Agent, or Firm* — Farber LLC

(57) ABSTRACT

Devices and methods for cleaning and/or drying endoscopic instruments, such as endoscopes, are provided. A drying device for use with an endoscopic instrument comprises an elongate member configured for advancement through an internal lumen within the endoscopic instrument and a drying member removably coupled to a portion of the elongate member. The drying element comprises a variable pressure region shaped and configured to increase the hydrodynamic fluid friction force and fluid pressure force applied to the wall of the internal lumen of the endoscope to more effectively remove all of the moisture and fluid from the internal surfaces of an endoscopic instrument.

20 Claims, 31 Drawing Sheets

PRESSURE DISTRIBUTION

Related U.S. Application Data application No. 17/509,304, filed on Oct. 25, 2021, now Pat. No. 11,357,394.

(60) Provisional application No. 63/105,072, filed on Oct. 23, 2020.

(51) Int. Cl.
*B08B 9/043* (2006.01)
*F26B 5/16* (2006.01)

(56) References Cited

U.S. PATENT DOCUMENTS

| | | |
|---|---|---|
| 9,115,945 B2 | 8/2015 | Williams |
| 9,968,247 B2 | 5/2018 | Kaye |
| 11,357,394 B2 * | 6/2022 | Miller .................... A61B 90/70 |
| 2022/0373258 A1 * | 11/2022 | Miller ..................... F26B 5/14 |

* cited by examiner

PRESSURE DISTRIBUTION

VISCOUS SHEAR STRESS ON THE INNER WALL

PRESSURE ON THE INNER WALL

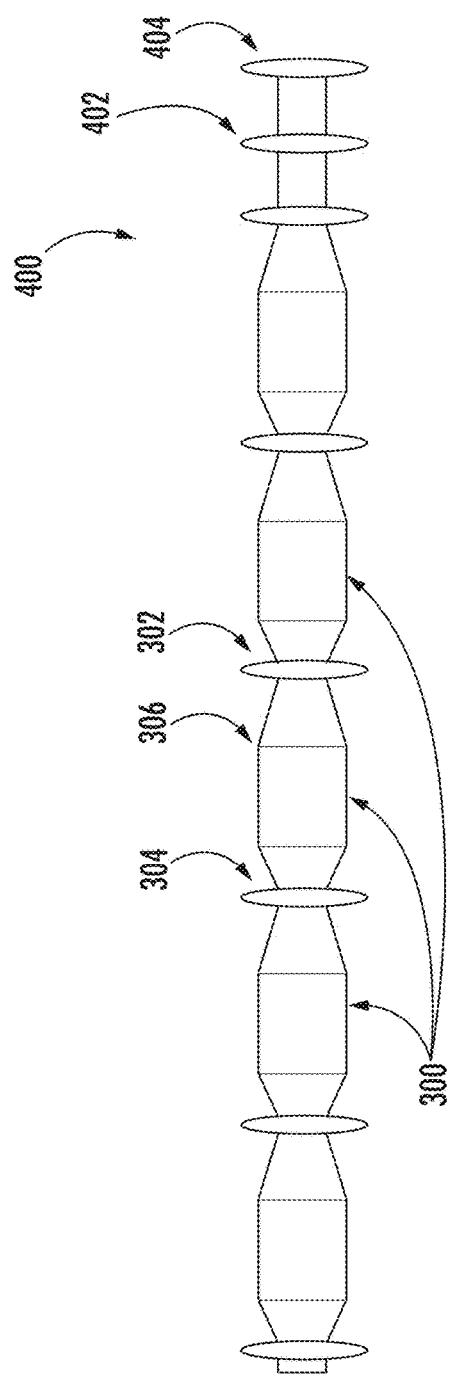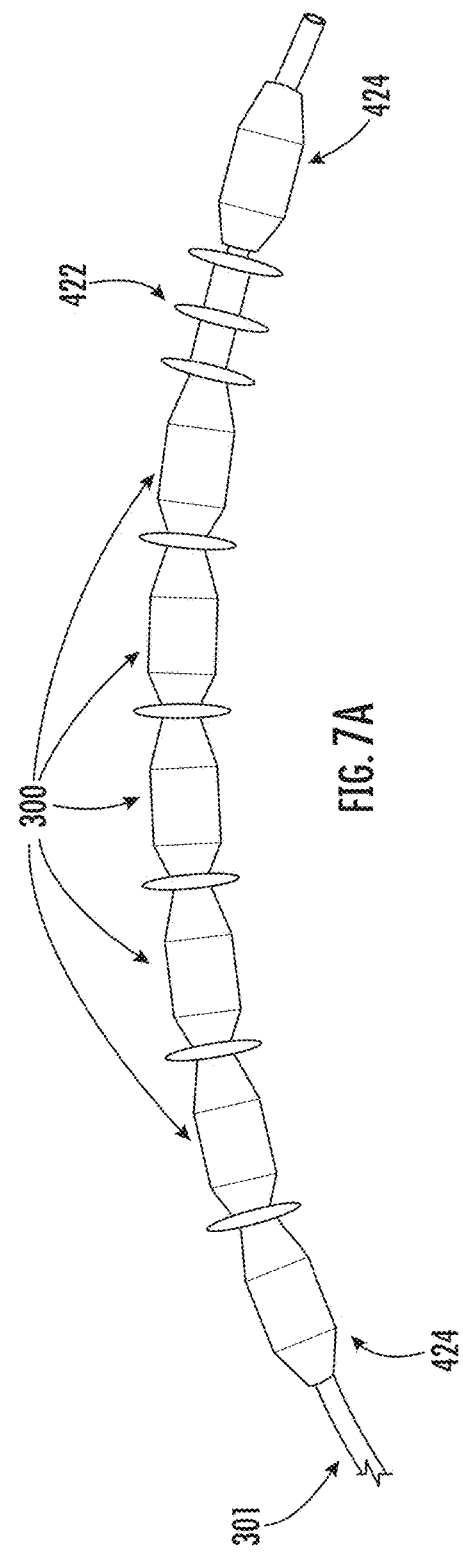

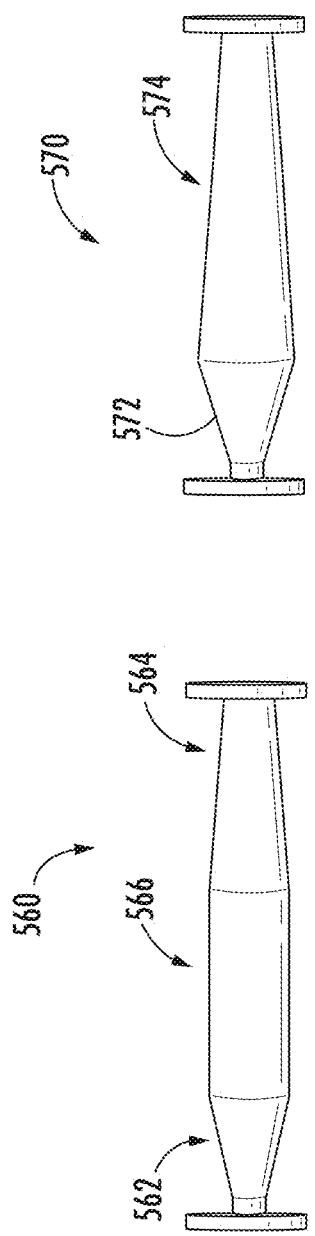
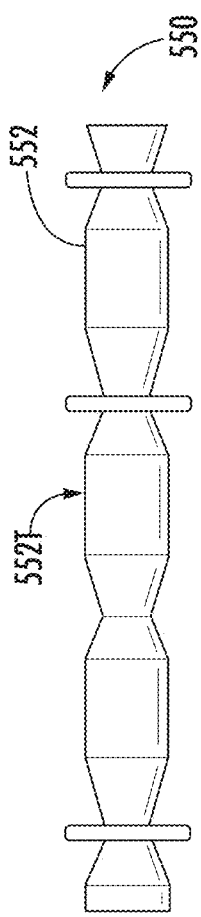
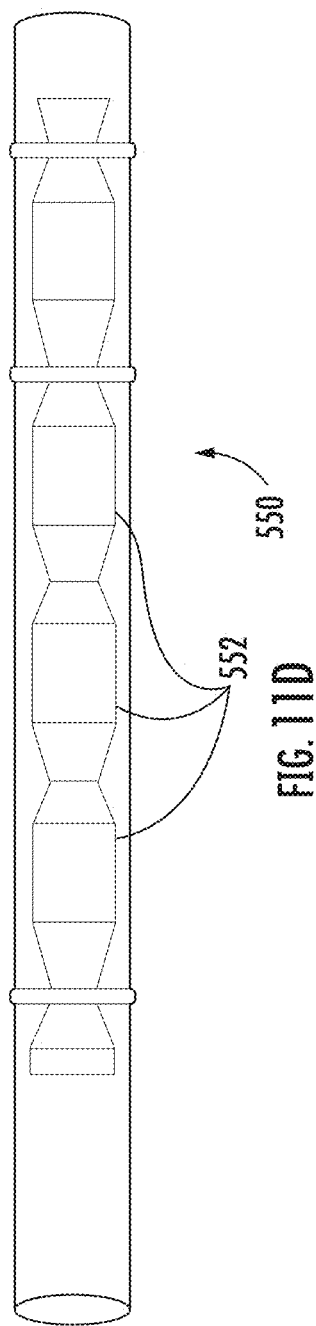
FIG. 11A
FIG. 11B
FIG. 11C
FIG. 11D

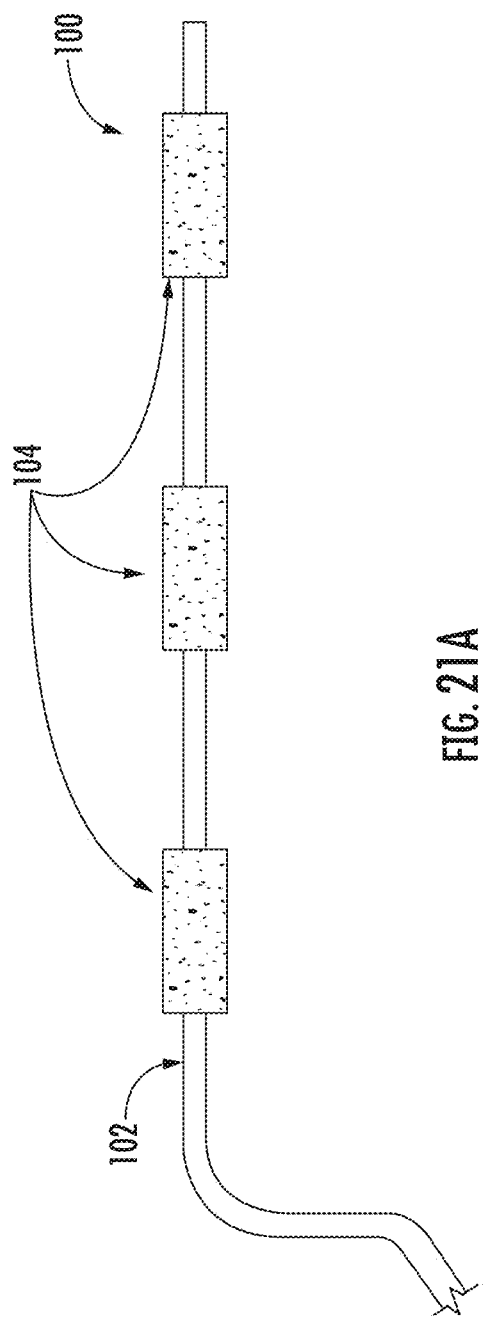

SYSTEMS AND METHODS FOR DRYING AND/OR CLEANING ENDOSCOPIC DEVICES

CROSS-REFERENCE TO RELATED APPLICATIONS

This application is a Continuation of U.S. patent application Ser. No. 17/739,146, filed on May 8, 2022, and entitled "Systems and Methods for Drying and/or Cleaning Endoscopic Devices," which is a Continuation-in-Part of U.S. patent application Ser. No. 17/509,304, filed on Oct. 25, 2021, Issued as U.S. Pat. No. 11,357,394 on Jun. 14, 2022, which claims the benefit of U.S. Provisional Application No. 63/105,072, filed on Oct. 23, 2020, the entire disclosures of which are incorporated herein by reference in their entirety for all purposes.

BACKGROUND

Endoscopes are used and reprocessed numerous times each day to deliver highly advanced optical performance, consistent real-time imaging transmission, predictable scope handling and other functionality important to successful diagnosis and treatment of clinical conditions. This also occurs in non-medical applications involving the inspection, cleaning and repair of remote locations with non-medical endoscopes. This includes, by way of example, but not limitation, the inspection and repair of hydraulic lines, oil field pipelines, oil refinery lines and lumens, sewer and plumbing lines, the internal areas of a combustion engine and other non-medical applications involving remote visualization of an area that benefits from remote access and assessment.

Endoscopes are high technology instruments, typically having advanced, expensive optical chips at the distal end of the scope to facilitate exceptional visualization. These imaging signals are captured on the chip and communicated in turn through high definition image transfer technology involving sophisticated software and imaging processing hardware that processes the optical signals. These signals in turn are translated and projected through the software and processor at numerous frames per second to an imaging screen, console or other means of transmitting the image to a user distant from the optical chip.

The exceptional imaging capability of endoscopes has enabled numerous advances in medical and non-medical fields. This is due in significant part to the combination of excellent optical performance and scope handling joined to the reusable nature of nearly all endoscopes. This powerful combination allows for advanced, premium optical elements to be made available at a reasonable per use cost due to the ability to clean, disinfect (as applicable) and reuse the endoscope with its advanced optical capability. The ability to reuse these scopes effectively spreads the high cost of the endoscope's capability across multiple procedures/uses, thereby enabling reasonable, low cost access to advanced technologies for multiple beneficial uses on a global basis. Endoscopes with these advanced optical capabilities are too expensive to be used once and discarded. In addition, the environmental impact of discarding the advanced electronics that facilitate the endoscope's capability is considerable, unwarranted and unsafe for the environment. Reusable scopes provide a way to make peak optical capability available for a variety of procedures where otherwise one would not be able to afford the cost to use such technology.

Even with the considerable advances and capabilities offered by reusable endoscopes, recent concerns have arisen regarding one's ability to consistently and predictably clean and thereby remove all soil and biomatter that contaminates endoscopes during use. Successful cleaning is the critical step to support disinfection and/or sterilization (as applicable) to reprocess these scopes for their next use. Cleaning non-medical scopes is also important to avoid inhibiting scope performance with the next use because of retained matter that can accumulate and adversely impact scope performance. This applies to both non-robotic scopes and scopes connected to or otherwise used with robotic technology to use remote visualization to see, navigate and treat, as applicable.

Multiple contamination-related reprocessing issues leading to potential patient infections and/or scope performance issues have been noted with these scopes. These include issues with the cleanliness of reusable valves used to facilitate suction and air/water expression, the presence of residual matter that cannot be consistently removed from the complex distal end of certain scopes (especially duodenoscopes and endoscopic ultrasound scopes), and concerns regarding successful cleaning of the long biopsy/working channel(s) in certain scopes that are important for passing instruments to the distal end of the scope.

Nearly all of these issues are addressable through the use of new, relatively low cost technologies and practices that have been created in response to these concerns and which can be applied in the context of current workflows and procedure economics, and which are environmentally friendly, especially when compared to single-use scope alternatives. These relatively low cost technologies and practices include the use of single-use disposable tubing and disposable valves instead of reusable tubing and valves, the use of sterile, single-use endoscopic shields to seal the complex distal end of the scope during use and initial pre-cleaning instead of leaving this area open and exposed to contamination, the use of forced-air drying, improved adherence to reprocessing approaches, and the implementation of post-procedure culturing and monitoring to address other areas of concern.

With all of these advances, an area that remains to be addressed is the cleaning of the internal lumens of the endoscope. During a medical procedure, the internal biopsy and suction channels become heavily contaminated with bacteria, biomatter and debris through the passing of multiple instruments through the biopsy channel and through the actuation of suction to remove mucus, debris and other matter that may obscure the physician's visualization during the procedure. All of these activities benefit patients by delivering care through the scope in a less invasive manner, but in parallel with these beneficial activities the scope experiences heavy contamination of these channels, which then must be cleaned effectively to return the scope to use for the next patient (or non-medical use) without exposing the next patient (or non-medical use) to the risk of a scope-related infection (or a poor performing, unclean non-medical scope). It is well known that without successful cleaning, an endoscope cannot be disinfected or sterilized successfully. Unremoved biomatter and debris act as a shield for pathogens, protecting the pathogens from being killed by disinfectants and sterilants used to reprocess the scope. Additionally, unremoved biomatter, and pathogens create the opportunity for organisms to attach to surfaces inside the scope, engage in replication and form biofilm, which makes removal of these organisms particularly difficult and which, in turn, creates risk for the transmission of multi-drug resistant infections through the scope. Biofilm can replicate, detach and then attach in a new location and repeat this process, while also recruiting other organisms into the biofilm during the process, creating additional multi-drug resistant organisms (MDRO) that cannot be effectively treated with antibiotics. MDRO infections are exceptionally dangerous and have resulted in multiple deaths around the world from contaminated endoscopes that were not reprocessed successfully.

In the current Covid-19 pandemic, the importance of successful cleaning becomes even more pronounced. It is now well documented that Covid-19 infections begin in the lungs, but quickly migrate to the gastrointestinal tract, with virus replication occurring in these organs prior to detectable symptoms. A significant number of endoscopic procedures involve the use of endoscopes, including by way of example, but not limitation, to examine and treat pulmonary conditions (e.g. bronchoscopies using a specialty endoscope called a bronchoscope), and to diagnose and treat conditions in the gastrointestinal tract (e.g. use of gastroscopes, duodenoscopes, endoscopic ultrasound scopes and colonoscopes), raising the potential that Covid-19 virus could become encapsulated in biofilm resulting from an incomplete cleaning of an endoscope and in turn progress to a drug resistant strain of Covid-19 that could be transmitted to subsequent patients. In view of all of these concerns, a new innovation is needed to notably improve the effectiveness and predictability of successful cleaning of the lumens of endoscopes.

Current Cleaning Practices and Technologies

Current endoscope channel cleaning practices utilize certain cleaning technologies that can increase the variability and even have a potentially adverse effect on the success of cleaning endoscope channels. The most commonly used cleaning approach involves passing a nylon wire bristle brush on the end of a long pushing/pulling element into the proximal end of the biopsy channel of the endoscope. The wire brush is inserted at the biopsy port at the proximal end of the scope and advanced down the biopsy channel to the distal end of the scope, and repeated with other internal channels as well. This action should be performed while the scope is submerged in a cleaning fluid with the intent being for the mechanical action of the wire bristles to remove biomatter and debris after immersing the scope in the cleaning fluid.

With this activity, after the wire bristle brush immerges at the distal end of the biopsy channel, the person performing the cleaning is supposed to examine the brush for any visible signs of debris and if any debris is noticed, repeat this activity until no visible debris is noticed on the brush. The goal with this series of actions is to remove all visible debris and biomatter from the internal channels in the scope through the mechanical action of the brush. The brushing occurs following immersing the scope briefly in cleaning fluid, which is intended to loosen up contaminants before passing the brush.

Limitations of Current Approaches

Current endoscopic channel cleaning approaches have a number of notable limitations that increase the variability of cleaning results and have an overall adverse effect on the success of cleaning endoscope channels. The first issue is current cleaning approaches involve advancing a cleaning brush from the proximal end of the scope at the opening of the biopsy channel, down the channel to the distal end of the scope, where instruments exit the scope inside the patient. This approach means that any biomatter, debris, bacteria and other contaminants present in the channel are pushed from the proximal end of the scope, which is the least complex part of the scope to clean, to the distal tip of the scope, which is the most complex part of the scope to successfully clean and reprocess, and which is the area that has been linked to the most scope-related infections and deaths. In essence, the cleaning brush acts as a tool that not only partially removes debris in the channel, but it also shovels or pushes contaminates out of the biopsy channel into the most difficult to clean area on the scope, with the highest level of scope-related infection risk. Logically, one would want to do everything possible to do the opposite of what is currently done with the direction for passing cleaning brushes through the biopsy channel and suction channel (i.e. pass from distal end to proximal end exit of the biopsy channel). This current approach with brushes occurs with certain complex scopes, such as duodenoscopes, because of limitations with current technologies, including, by way of example not limitation, demonstrated issues where the complex distal end of the scope resulting in the wire bristle brush becoming stuck at the distal end and therefrom becoming not advanceable to clean the scope's biopsy/working channel.

In addition to this limitation, the cleaning brushes themselves also have a number of notable limitations that inhibit consistent, repeatable scope reprocessing success. Pictures of the interior of the scope biopsy channels after cleaning with a nylon wire bristle brush reveals that the bristles deflect while being passed through the channels, leaving streaks along the interior of the channels rather than a clean consistent cleaning result. These channels can be highly contaminated with debris, biomatter and bacteria after experiencing repeated passing of therapeutic instruments during procedures, as well as from the actuation of suction to remove debris, mucus and other biomatter during a procedure. Using brushes that deflect and cause streaks means that channel cleaning is incomplete and will be highly variable. In addition, trying to offset this limitation through the use of repeated nylon wire bristle brush passes, which is recommended by the scope manufacturers, does not overcome this issue and does not result in in a predictably and completely clean channel. Instead, the combination of repeated passes using a stiff bristle brush causes injury to the surface of the interior endoscope channel, as the bristles create scratches and crevasses from the effects of the multiple wire passes. These scratches and crevasses allow bacteria and biomatter to infiltrate and reside in these new spaces even with multiple brush passes to clean the scope after the next case, limiting the consistency of the cleaning result and thereby inhibiting the ability of disinfectants and sterilants to successfully disinfect and sterilize the scope to safely return it for use in the next case. All biomatter and debris must be successfully removed in order to successful disinfection and reprocess a scope. Left behind biomatter and debris acts as a shield over pathogens that may reside in these channels (including naturally occurring bacteria from the patient) preventing successful treatment with disinfectants and sterilants that kill the pathogens and make the scope safe for reuse with the next patient.

Related to this circumstance is the assumption that personnel cleaning a scope will engage in repeated wire bristle brush passes. The scope manufacturer's instructions for use direct the person cleaning the scope to pass the wire bristle brush until there is no visible debris, which is not clear evidence that brush passes have resulted in successful cleaning, given the deflecting bristles. Additionally, it is not clear that all persons involved in cleaning with wire bristle brushes always engage in repeated brush passes (plus a visual test is not completely accurate). A device that can clean the biopsy channel effectively and in a single pass would be a significant way to remedy these issues.

An additional issue involves instrument injury to the biopsy channel through incorrect passing of instruments. The biopsy channel is typically made with PTFE or other polymeric material. It is designed to allow for predictable passing of instruments and typically has a low coefficient of friction to support instrument passing. The channel is compatible with a wide range of instruments and the diameters of the instruments passed are meaningfully smaller than the diameter of the endoscope's biopsy/working channel, providing room for safe advancement of instruments through the channel. That said, occasionally instruments are not used correctly, such as attempting to open a biopsy forceps in the biopsy channel, or attempting to withdraw a biopsy forceps back through the channel without having the forceps properly closed. When this occurs, a scratch, divot, or crevasse can result in the biopsy channel, which in turn increases the difficulty of achieving successful and predictable removable of biomatter and debris when cleaning the biopsy channel. There is no evidence a wire bristle brush can remove debris from injuries to the biopsy channel in a predictable and consistent manner. Recently published data from a nationwide survey indicates cleaning of the biopsy channels with current methods fails to remove biomatter and debris up to 15% of the time with two complex specialty endoscopes: duodenoscopes and endoscopic ultrasound scopes.

An alternative technology to the nylon wire bristle brush is a pull thru brush cleaner, such as the Pull Thru™ Cleaning Brush manufactured for Cantel Medical. The pull thru brush cleaner is designed with five cylindrical fins, which are arranged in very close proximity to each other with two of the fins clustered together, followed by a larger space and then three additional fins clustered together. The fins are a flexible polymer overmolded on to a rod of stiffer material that is used to advance the cleaner down the scope biopsy channel from the proximal end of the scope to the distal end, while the scope is submerged in cleaning fluid. The space between each cluster of fins is uniform and the polymer between the fins is a thin, uniform thickness that is overmolded to adhere to the cylindrical monofilament. The benefit of the pull thru cleaner is less trauma to the walls of the biopsy channel compared to a wire brush cleaner. There is also some evidence that the pull thru cleaner is able to more effectively remove biomatter from a contaminated biopsy channel.

There are, however, multiple drawbacks with pull thru cleaning brushes. Similar to the wire bristle brush, the pull thru cleaning brush is designed to pull debris from the proximal end of the biopsy channel to the high-risk, difficult to clean distal end of the scope, raising the potential contamination of the distal end as it attempts to clean the scope's biopsy channel. An additional limitation with these devices is that the cylindrical fins are significantly oversized relative to the diameter of the biopsy channel, resulting in meaningful deflection at the end of the fins, which creates a buckling effect that results in a gap between the fin and biopsy channel. This gap or lack of consistent wall conformance can mean that not all potential contaminants are addressed when the pull thru brush is moved through the biopsy channel. Additionally, this gap means that a change in the surface of the wall of the biopsy channel, such as a change due to a scratch or crevasse from an instrument pass, is unlikely to be addressed by the pull thru brush as it is moved through the biopsy channel. The fins are unable to impact scratches and crevasses as the fins pass over injuries to the channel wall.

An additional limitation that exists with all of the technologies used to clean the internal lumens of endoscopes is the lack of a collaborative and complementary element between the two technologies used for the cleaning steps. All reusable endoscope manufacturers require as a first step in the cleaning process that the endoscope be placed in a fluid that is formulated to assist with the removable of biomatter and debris, followed by a second step of brushing the internal channels while the scope is immersed in the cleaning fluid. Multiple formulations of cleaning fluid exist, but the most commonly used are either an enzymatic cleaner, or a ph-neutral non-enzymatic cleaner. The cleaners are intended to loosen the adhesion of biomatter and bacteria to the walls of the channel, though this is not effective on its own and even with brushing, evidence exists that not all biomatter is consistently removed.

One of the significant limitations of this current approach is that the cleaning fluids and brushing applications are independent technologies that are used together (i.e. a scope submerged in cleaning fluid while brushing of channels occurs), but these technologies are not designed in a way where the technologies actively complement and enhance the effectiveness of each other. A new innovation is needed that addresses the notable limitations of current brushing technologies and that can actively complement and work-in-concert with the cleaning fluids used in this important cleaning step with reusable endoscopes. A new innovation is needed to address these critical limitations and assure predictable and consistent cleaning of the biopsy and suction channels and other lumens (as applicable) of reusable endoscopes.

Current Drying Practices and Technologies

Another significant unmet need with these instruments and with this process is a downstream issue associated with drying the instrument after the cleaning and/or disinfection or sterilization process is completed. Most, if not all, of the disinfection or sterilization approaches involve some element of liquid or gas delivery of the disinfectant or sterilant, followed in most protocols by flushing with an agent, such as water or sterile water, or in select and very limited instances, evaporation of the agent.

In all of these processes, a critical final step after the disinfection or sterilization is drying of the instrument. For external surfaces of the medical device, this aspect of the process is fairly straight-forward, but for recessed areas and especially relatively narrow and sometimes long channels, the drying of these areas is difficult, lengthy and not predictable or consistent. Failing to effectively dry counteracts the benefits of the entire reprocessing approach, including the disinfection and/or sterilization steps. This is because wet surfaces promote the proliferation of pathogens and biofilm. If the instrument is dry, then pathogens and biofilm cannot grow. Hydration is a central element for the growth of pathogens and biofilm, which lead to infections, including nosocomial, drug-resistant and other deadly infections. For non-medical uses, residual hydration promotes the growth of biofilm and pathogens which can effect device performance and even expose a user eventually to one or more pathogens.

Current approaches to drying have applied a number of inconsistent, variable methods that do not provide consistent assurance that the moisture within these channels and recessed areas is removed and therefore the remote and/or recessed areas are dry. Unsuccessful attempts have been made to just hang devices vertically, so wet channels are positioned so the effect of gravity causes water inside channels to eventually run down and evaporate. This approach has been disproven with evidence that even after days in this position, these channels are not consistently and completely dry.

Attempts to overcome these issues have included flushing these channels with alcohol, under the premise this may accelerate drying and act as an additional bacteriostatic agent (though the instrument in medical applications had already been disinfected or sterilized at this point). Data shows this does not clearly accelerate drying times or drying effectiveness and can even lengthen the drying process in certain instants. In addition, there are concerns that the use of alcohol may actually fixate certain otherwise inert or innocuous bacteria and pathogens in the channel that in turn can be passed on to the patient or user.

Other approaches involve using air drying approaches, which is inherently difficult, time-consuming and variable due to the recessed and at times long thin channels that must be dried. Certain of these channels are four to six feet long with diameters that are only a few millimeters or less. Efforts to dry include aiming compressed air at or into a channel, or hanging the instrument in a cabinet with circulating air that uses motorized fans to blow air into small spaces to improve drying. Certain of these approaches have filtered air that is blown by a motorized fan through tubing into tight areas, such as endoscope channels and labeled "forced air drying." Even these more proactive and more targeted approaches have variable results, which is due, at least in part, to the distance that the air must travel to dry the channel, the variable channel diameters of the channels, which impact the air velocity, and the surface tension of the water, which can be greater than the force of the air at different points, preventing effective and timely removal of the water. Additionally, the tight spaces essentially trap or help retain and promote a humid environment, inhibiting evaporation. Challenges beyond even these significant difficulties include endoscopes and other instruments with curved internal channels and lumens where one or more channels come together creating even more variable surfaces, such as Y-junctions and connectors where water can pool and areas adjacent to and/or outside of valves that interact with a channel.

Accordingly, it would be desirable to provide improved systems and methods for cleaning biomatter from endoscopic instruments, such as endoscopes and other instruments with remote channels and lumens, and then drying those endoscopes after they have been cleaned so that the channels and lumens can be effectively sterilized or disinfected. In particular, it would be desirable to provide devices that can effectively clean and/or dry all internal surfaces of endoscopic technologies, including crevasses, Y-junctions, and scratches or other irregularities, without further damaging these surfaces.

SUMMARY

Devices and methods are provided for cleaning biomatter, tissue or other debris from endoscopic instruments, such as endoscopes, particularly internal lumens or other spaces within the endoscopic instruments. Devices and methods are also provided for drying the internal lumens of these endoscopic instruments after they have been cleaned, and for testing to confirm successful cleaning and drying. The methods and devices disclosed herein may be used with, or may be incorporated into, a variety of different reusable or disposable endoscopic instruments and devices that include internal lumens or other internal spaces, such as endoscopes, trocars, cannulas, dilatation devices, Foley catheters and other in-dwelling catheters, guidewires, central venous catheters, bipolar or monopolar electrosurgical or ultrasonic devices, arterial lines, drainage catheters, peripherally inserted central catheters, endotracheal tubes, feeding tubes, ventilators, respirators, robotic surgery devices and other devices that in-dwell, penetrate and/or navigate in the body. The dimensions of the cleaning and drying devices disclosed herein would, or course, be adjusted for the size of the particular instrument or device.

The disclosed innovations address the multiple limitations with current approaches for cleaning and/or drying endoscope lumens or channels, and provide new, important capabilities to improve cleaning and drying performance. In some embodiments, the devices disclosed herein overcome the notable defects with the current channel cleaning approaches wherein brushes and cleaning fluids are not designed to work together and complement each technology's respective capabilities. These innovations not only address the current issues with brushes, but also complement and enhance the effectiveness of cleaning fluids used in the channels of endoscopes. In addition, certain embodiments provide the advantages that the lumen(s) of endoscopic instruments can be cleaned without creating defects in the surfaces of the internal lumen. This increases the life of the instrument and allows the instrument to be cleaned multiple times without providing additional areas for biomatter, pathogens or other debris to reside. In certain embodiments, these innovations provide devices that can rapidly and consistently dry the internal lumens or channels of endoscopic instruments.

In one embodiment, a drying device for use with an endoscopic instrument comprises an elongate member configured for advancement through a lumen within the endoscopic instrument and a drying element coupled to at least a portion of the elongate member. The drying element includes certain portions that have an outer diameter equal to or greater than the outer diameter of the elongate member.

In embodiments, the elongate member comprises an attachable pushing and pulling element, such as a navigation element, that can be advanced from the proximal end of an internal lumen of an endoscopic instrument, such as a biopsy channel on an endoscope, to the distal end of the biopsy channel in order to exit from the biopsy channel and connect to the drying element. In certain embodiments, the drying element is removably attachable to a distal end portion of the advancing or navigation element. In other embodiments, the drying element is permanently attached to the navigation element. These embodiments allow the drying element to be translated from the distal end of the scope lumen to its proximal end or vice versa.

In one embodiment, the drying member comprises distal and proximal end portions having a diameter substantially equal to or greater than an inner diameter of the lumen and a variable pressure central portion between the distal and proximal end portions. Alternatively, the proximal and distal end portions may have a diameter substantially less than an inner diameter of the lumen. The variable pressure central portion is shaped to create a pressure gradient along the central portion from the distal end portion to the proximal end portion. This pressure gradient causes an increase in a relative velocity between the drying member and any air or fluid within the lumen as the drying member is advanced through the lumen. The increased velocity of the air fluid increases the shear stress between the air or fluid and the lumen wall, thereby creating more force to dry the wall.

In certain embodiments, the drying device is sterilized or disinfected so that the disinfected and/or sterilized device channel is not compromised by the drying process. Instead, when the drying device is passed through the already disinfected or sterilized device channel, water and moisture is removed without altering or contaminating the disinfected or sterilized state of the device with the channel.

In embodiments, the proximal and distal end portions of the drying member create consistent circumferential contact with the interior wall of an endoscope channel, such as a biopsy or suction channel. In certain embodiments, these channel contact elements preferably have a substantially circumferential, cylindrical or conical shape with at least one portion of the element having a diameter approximately equal to or slightly larger than the diameter of the internal lumen. In an exemplary embodiment, the diameter of the proximal and distal end portions is about 1 to about 1.5 times the diameter of the internal lumen, preferably about 1 to about 1.25 times this diameter. This avoids deflection of the proximal and distal end portions, thereby reducing the buckling and the creation of a gap between the drying element and the internal wall of the lumen.

The variable pressure central portion is designed to create variable pressure between the two circumferential elements and the wall of the channel being cleaned. Thus, as the drying member is advanced inside a channel and the scope and its channels, the variable pressure design between the two circumferential elements creates a venturi effect between the drying element and the walls of the endoscope channel when the drying element is moved through the lumen.

In certain embodiments, the central portion of the drying member comprises a contraction section coupled to the proximal end portion, a diffusion section coupled to the distal end portion and a throat section coupling the diffusion and contraction sections. The throat section has a diameter less than the diameter of the proximal and distal end portions and greater than a diameter of the diffusion and contraction sections.

The variable pressure region between the two cylindrical elements may include an inverted, partial venturi shape, a parabolic shape, a variable slope shape or such other shape that creates variable pressure between the two cylinders and the wall of the channel being dried, thereby increasing the force against the channel wall when the drying member is advanced. In an exemplary embodiment, the throat section is substantially cylindrical. The contraction section preferably increases in diameter from the proximal end portion to the throat section and the diffusion section preferably decreases in diameter from the throat section to the distal end portion, thereby creating a venturi effect between the distal and proximal end portions of the drying element.

The angle of the slope of the contraction section may vary depending on the diameter of the channel being dried and other factors and should be sufficient to support a variable pressure flow between the cylinders when the drying element is advanced. In certain embodiments, the contraction section defines an angle with the proximal end portion that is about 4 degrees to about 85 degrees, preferably between about 15 degrees to about 30 degrees. Similarly, the diffusion section defines an angle with the distal end portion that is about 4 degrees to about 85 degrees, preferably about 15 degrees to about 30 degrees. In other embodiments, the contraction section may have more than one slope, a curve shape, a variable shape or such other shape which assists in varying the pressure between the two cylindrical elements.

Likewise, the angle between contraction and diffusion sections and the throat section may vary depending on the diameter of the channel being dried, and other factors and should be sufficient to support a variable pressure between the cylinders when the drying element is advanced. In certain embodiments, this angle is about 10 degrees to about 50 degrees, preferably about 15 degrees to about 30 degrees and more preferably about 20 degrees to about 25 degrees.

The length and diameter of each section of the variable pressure region are preferably selected to optimize the Venturi Effect (or in embodiments, an inverted Venturi Effect) and will vary based on the diameter of the internal lumen and other factors. For example, in a lumen having a diameter of about 4.2 mm, the length of the throat section may be about 2 mm to 10 mm, preferably about 3 mm to 5 mm, and more preferably about 4 mm. The diameter of the throat section will also depend on the diameter of the inner lumen as well as the diameter of the contraction and diffusion sections. In certain embodiments, the throat section has a diameter less than the diameter of the internal lumen, but greater than 50% of the diameter of the lumen, preferably greater than about 60% of the diameter of the lumen, and more preferably equal to or greater than about 70% of the diameter of the lumen.

When the drying element is advanced through a lumen, the variable pressure region of the drying element is configured to generate pressure against the internal wall of the lumen. In certain embodiments, the variable pressure region is configured to generate a peak pressure of at least about 75 Pa in at least one area between the distal and proximal end portions of the drying element. This peak pressure is preferably at least 100 Pa and more preferably at least 125 Pa. In an exemplary embodiment, the peak pressure may be approximately 150 Pa. This direct pressure against the lumen wall is sufficient to completely remove all fluid and moisture from the internal surface of the lumen.

The variable pressure region of the drying element is configured to generate an average or mean pressure across the distance between the proximal and distal end portions of the drying element of at least about 10 Pa, preferably about 20 Pa and more preferably about 30 Pa. In an exemplary embodiment, the mean pressure is about 36 Pa.

The variable pressure region of the drying element is also configured to generate a peak shear stress of at least about 4 Pa in at least one area between the distal and proximal end portions of the drying element, preferably at least about 5 Pa and more preferably at least about 8 Pa. The average or mean shear stress across the distance between the proximal and distal end portions of the drying element is at least about 1 Pa, preferably about 2 Pa and more preferably greater than 2.5 Pa. In an exemplary embodiment the mean shear stress is about 2.8 Pa.

In certain embodiments, the drying device/element includes more than one drying member. For example, in one such embodiment, the drying device includes 2-10 drying members, preferably 2-5 drying members. The drying members may be coupled to each other to provide a string of such drying members along the navigation element, or separated by various distances, to increase the effectiveness of the device. In these embodiments, for example, the proximal end portion of one drying member may be coupled to, or may be integral with, the distal end portion of the next drying member along the string. Each of the drying members comprises distal and proximal end portions having a diameter substantially equal to or greater than an inner diameter of the lumen and a central portion between the distal and proximal end portions. The central portion of each drying member is shaped to create a pressure gradient along the central portion from the distal end portion to the proximal end portion. The variable pressure elements in each drying member may be the same or may vary to create alternating pressure profiles. The multiple cylindrical elements with variable pressure elements between the cylindrical elements may be greater or less than five sets, as appropriate for the given application.

In one embodiment, the drying element is removably coupled to the elongate navigation element such that the navigation element can be advanced from the proximal end of an endoscope lumen, such as a biopsy channel, through the lumen to its distal end. The navigation element may then be attached to the drying element so that the entire system can then be pulled from the distal end of the endoscope back through the lumen to its proximal end. This approach to drying can also be used to dry other lumens in the scope, including the suction channels and the air/water channel(s), as applicable. In other circumstances, the devices can be used to dry from the proximal to the distal end of the channel or other endoscopic instrument to be cleaned.

In embodiments, the drying member, or the elongate navigation member, may include an element which centers the navigation element and the drying element as the device is pulled or pushed through lumens around turns and navigates through corners and other complex areas, including junctions of multiple lumens and internal channels in the scope or other instrument being cleaned. This centering element, in embodiments, is smaller than the diameter of the lumen through which the device is being advanced, but has a significant enough size to prevent misalignment and deflection of the navigation element to one side or another of the lumen as it navigates, including as the cleaning element is pulled or pushed around curves, corners and junctions of various lumens (including Y junctions).

In some embodiments, the centering element may comprise a series of shaped elements projecting from the elongate member or the navigation member. This series of shaped elements may, for example, comprise struts, spikes, or other projections extending radially outward from the elongate member and sized to substantially center the elongate member and/or the drying/cleaning elements within the internal channel of the endoscopic device.

The centering element may be any shape that keeps the device generally centered in the lumen and prevents this deflection, with a preferred embodiment being a cylindrical shape with a tapered distal end. When this sort of misalignment occurs, which is an issue with existing brushes and pull thru devices, the brushes and other elements are pulled to one side of the lumen as the devices are pulled around curves, corners and junctions of lumens, with the result being contact with the lumen wall and the drying element (whether a brush, pull thru or other device) is minimized, altered in an adverse way, or lost, resulting in an adverse impact on the effectiveness of the drying approach. By placing a centering element at the front or back, or both of the device, this issue is corrected, resulting in more consistent, effective drying, especially around curves, corners, channel junctions and other complex areas inside an endoscope or other endoscopic instrument or device.

In a preferred embodiment, the centering element is between 50 percent and 90 percent of the diameter of the lumen being cleaned, with a further preferred embodiment having a diameter or height between 70 percent and 85 percent of the diameter of the lumen being cleaned. The centering element can be any shape that preserves the centering of the drying element as it is navigated through a channel. In embodiments, this includes cylindrical, conical, spherical and a centering element may be placed at the distal area of the device, at the distal and proximal end, between drying members, or the proximal end, as appropriate to aid in centering the drying element, especially as it navigates around curves, across Y-junctions and other aspects of a lumen.

In certain embodiments, the drying device includes a programmable motor coupled to the elongate member and configured to translate the device through the lumen of the endoscopic instrument. The programmable motor is preferably configured to withdraw the elongate member through the lumen a specified distance for a specified duration of time. For example, the motor may be programmed to withdraw the elongate member at a specific velocity that optimizes the increased velocity created by the variable pressure region within the drying member, thereby ensuring that the internal lumen is sufficiently dried without damaging the surface.

In another aspect, a kit for cleaning and drying an endoscopic instrument comprises a drying device having an advancement element configured for advancement through a lumen within the endoscopic instrument and at least one drying member coupled to a portion of the advancement element. At least a portion of the drying member is shaped and configured to substantially maintain contact with a wall of the lumen as the advancement element is advanced through the lumen. The kit further comprises a cleaning device having an elongate member configured for advancement through the lumen within the endoscopic instrument and at least one cleaning member coupled to a portion of the second elongate member. The cleaning member comprises distal and proximal end portions and a central portion between the distal and proximal end portions and wherein the central portion is shaped to create a pressure gradient along the central portion from the distal end portion to the proximal end portion.

In one embodiment, the drying device is one of the embodiments described above and comprises distal and proximal end portions and a central portion between the distal and proximal end portions and wherein the central portion is shaped to create a pressure gradient along the central portion from the distal end portion to the proximal end portion.

The cleaning device may also comprise any of the combinations of the elements described above with respect to the drying device. The variable pressure central portion of the cleaning device is designed to create variable pressure between the two circumferential elements and the wall of the channel being cleaned. Thus, as the cleaning member is advanced inside a channel and the scope and its channels are submerged in cleaning fluid (as required by scope manufacturers), the variable pressure design between the two circumferential elements creates a venturi effect between the cleaning element and the walls of the endoscope channel when the cleaning element is moved through the lumen. As a result, when the cleaning fluid flows across the variable pressure area, this impacts the fluid flows as it transfers from an area of high pressure across an area of low pressure and then back to another area of high pressure between the two cylindrical elements. This directs the cleaning fluid at the channel walls with an increased velocity and force, thereby removing more biomatter and other debris than conventional devices. This same approach applies, in embodiments, with a drying device where air is directed through the creation of a venturi effect between the drying element and the walls of the channel as the device is move through the channel to remove fluid and moisture and dry the channel.

In certain embodiment, the drying device of the kit comprises an advancement element that may be a filament, wire, tube or other element capable of advancement into an internal channel, including a long, curved, or other channel that is difficult to access because it is recessed or internal. In embodiments, this element can be grasped at an end once it is pulled through the internal channel and then pulled through the channel as part of the drying process. It also can be advanced from the other end through pushing the advancement element. This element may include a version that is able to advance air through the device and into the channel, including to a removed location well inside the channel and beyond the typical effectiveness of forced air drying in a channel.

The drying member may comprise one or more substantially cylindrical members spaced from each other along the advancement member. The cylindrical members are configured to maintain contact with the channel wall to displace and remove any moisture as the advancement element travels through the channel. The advancement element may be advanced through being pushed, pulled or by other means, including back and forth agitation, advancement and withdrawal based on a pattern. The advancement element may travel through the scope by connection to an automated or mechanized approach or any other means of moving the channel drying element through the channel to displace, absorb and or remove water at least in part through direct contact with the surface area to be dried.

The drying members may be discs, fins, squeegees, or other projections extending outward from the elongate member. In embodiments, the drying members are shaped to create consistent circumferential contact with the interior wall of an endoscope channel, such as a biopsy or suction channel, as the elongate member is advanced therethrough.

In certain embodiments, the drying members preferably have a substantially annular, circumferential, cylindrical or conical shape with at least one portion of the element having a diameter approximately equal to or slightly larger than the diameter of the internal lumen. In an exemplary embodiment, the diameter of the proximal and distal end portions is about 1 to about 1.5 times the diameter of the internal lumen, preferably about 1 to about 1.25 times this diameter. This avoids deflection of the proximal and distal end portions, thereby reducing the buckling and the creation of a gap between the drying element and the internal wall of the lumen.

In certain embodiments, the elongate member of the drying device comprises a filament, wire, tube, shaft or other element capable of advancement into an internal channel, including a long, curved, or other channel that is difficult to access because it is recessed or internal. In embodiments, this element can be grasped at an end once it is pulled through the internal channel and then pulled through the channel as part of the drying process. It also can be advanced from the other end through pushing the advancement element. This element may include a version that is able to advance air through the device and into the channel, including to a removed location well inside the channel and beyond the typical effectiveness of forced air drying in a channel.

The drying member may comprise one or more substantially annular or cylindrical members spaced from each other along the elongate member. The cylindrical members are configured to maintain contact with the channel wall to displace and remove any moisture as the elongate element travels through the channel. The elongate element may be advanced through being pushed, pulled or by other means, including back and forth agitation, advancement and withdrawal based on a pattern. The elongate element may travel through the scope by connection to an automated or mechanized approach or any other means of moving the channel drying element through the channel to displace, absorb and or remove water at least in part through direct contact with the surface area to be dried.

In embodiments, the drying element of the invention may be any shape or form that can displace water and moisture through advancement and withdrawal, including a squeegee, disc, fin, cylinder, series of absorptive strips, venturi or inverted venturi, oblong and round shapes, a ball or spherical shaped drying element. The fins, discs, squeegees or other annular member, or other drying member, may be at any angle to the channel wall that promotes and enhances drying, including perpendicular, angled backward and an angle of between 1 and 89 degrees, angled forward at an angle of between 1 and 89 degrees or any other angle that promotes drying. In embodiments, these angles shall not be limited to this description and shall vary based on what is most effective for the drying for a given channel drying application.

In embodiments, the drying member may comprise a series of one or more cylindrical squeegees that are designed to make wall contact with the internal walls of the channel to remove fluid and moisture from the channel. These cylindrical squeegees may be arranged in any manner that is effective at removing fluid and moisture from the channel. This includes in groups of two and then three squeegees, or vice versa, or in other configurations of squeegees, such as groups of one and then two squeegees, two and then four, three and three, four in a row, five in a row or any other number and configuration of squeegees that is effective for the removal of water and moisture, depending on the channel diameter, length, curves, junctures with other channels and other factors.

In embodiments, certain of these squeegees may be of different heights in order to make the device more adaptable to use in channels of different sizes. For example, the device may have a squeegee that is 5 to 5.2 mm in diameter followed by a smaller squeegee that is between 2 to 2.2 mm in diameter, followed by another squeegee that is 3.8 to 4 mm in diameter to create variable wall contact across a variety of channel sizes. In embodiments, the height and arrangement of squeegees is not limited to this description and these diameters, placements, squeegee thickness and other shall vary based on what is most effective for the drying for a given channel drying application.

The spacing between squeegees and any other elements, including drying elements, may be any spacing that supports rapid and predictable channel drying, including a spacing of 1 mm, 1.25 mm, 1.5 mm, 2 mm, close spacing of 1.25 mm and then a 4 mm gap and then spacing of 1.25 to 1.5 mm or other spacing closer or farther or more variable that optimizes and supports rapid and predictable channel drying. Spacing, diameters and alignment and grouping of drying elements may vary based on channel size, channel material, the number of curves to navigate around, the number of junctions with other channels, if any, the channel dryer material, and other factors specific to the given channel drying application, in embodiments.

The thickness of squeegees and fins are any thickness that aids in channel drying and the positioning of the fins and squeegees to dry and, in embodiments, clean. In embodiments, this includes squeegee and fin thickness of between 0.2 and 0.5 mm, other variants with a thickness of 0.5 to 1.0 mm; other variances with tapered thickness with the thickness greater at the base of the squeegee or fin and tapering closer to the channel wall to enhance deflection and conformance of the element to the channel wall, while providing support and a certain rigidity and flexibility around the advancing element.

The annular members are spaced from each other along the elongate member. In some embodiments, the distance between each of the annular members is substantially equal. In other embodiments, this distance may vary between some or all of the annular members. For example, the device may include first, second and third annular members, with the first and second annular members being spaced from each other by a distance greater than the second and third annular members.

In one embodiment, the device includes at least first and second groups of annular members with each group having a plurality of annular members. The annular members within each group may be spaced substantially equally from each other, or they may vary in spacing. The first group is spaced from the second group by a distance greater than the spacing within each of the first and second groups.

In another embodiment, elongate member comprise a rod member having a first end, a second end and loop coupled to the first end. The device may further include a swab member having a first end attached to the loop and a second end comprising a tail. The swab member may have first and second ends where the first end is attached to the loop and the second end comprises a tail such as the tail of a kite where the tail can be of any length. The swab member may comprise one or more materials that can be braided or twisted with the tail end of the swab member comprising the unbraided or untwisted ends of the material or materials that comprise the swab member. In addition, the swab member may comprise a foam material and/or a microfiber material.

In addition, the rod member may comprise one continuous polymer rod with the looped end of the rod member comprising one thickness or diameter and the straight end of the rod member comprising two thicknesses or two diameters of the looped end of the rod. The two thicknesses or diameters of the polymer rod that form the straight end of the rod member may be fused or bonded together, laminated together, or co-extruded.

In embodiments, the drying device includes a centering element, so that the drying element(s) remain centered as they are advanced through the channel to dry. This centering element prevents a drying element from losing contact with the wall of the channel being dried, enhancing drying action. The centering element may be any shape that keeps the device generally centered in the lumen and prevents this deflection, with a preferred embodiment being a cylindrical shape with a tapered distal end. When this sort of misalignment occurs, which is an issue with existing brushes and pull thru devices, the brushes and other elements are pulled to one side of the lumen as the devices are pulled around curves, corners and junctions of lumens, with the result being contact with the lumen wall and the drying element (whether a brush, pull thru or other device) is minimized, altered in an adverse way, or lost, resulting in an adverse impact on the effectiveness of the drying approach. By placing a centering element at the front or back, or both of the device, this issue is corrected, resulting in more consistent, effective drying, especially around curves, corners, channel junctions and other complex areas inside an endoscope or other endoscopic instrument or device.

In a preferred embodiment, the centering element is between 50 percent and 90 percent of the diameter of the lumen being cleaned, with a further preferred embodiment having a diameter or height between 70 percent and 85 percent of the diameter of the lumen being cleaned.

In some embodiments, the centering element may comprise a series of shaped elements projecting from the elongate member or the navigation member. This series of shaped elements may, for example, comprise struts, spikes, or other projections extending radially outward from the elongate member and sized to substantially center the elongate member and/or the drying/cleaning elements within the internal channel of the endoscopic device.

In another aspect, a kit for cleaning and drying an endoscopic instrument comprises a drying/cleaning device having an elongate member configured for advancement through the lumen within the endoscopic instrument and at least one cleaning/drying member coupled to a portion of the second elongate member. The cleaning/drying member comprises distal and proximal end portions and a central portion between the distal and proximal end portions and wherein the central portion is shaped to create a pressure gradient along the central portion from the distal end portion to the proximal end portion.

In this aspect, the drying/cleaning device is configured to both clean and dry an internal lumen while being passed therethrough In embodiments, this version may be particularly useful to clean and dry after the use of liquid chemical sterilants and disinfectants.

In a preferred embodiment, the invention is configured for use with an endoscope. The advancing element is a polymer filament, wire or tube. The materials for the advancing element are any that are appropriate for the application, which, in embodiments, could be polypropylene, PET, nylon, PEEK, PTFE, ETFE, polyurethane, high or low density polyethylene, or other suitable polymer material. The advancing element could also be a metal wire (including stainless steel, nitinol or other material), or a combination of materials, including polymer reinforced by a wire, or a wire covered with a polymer or a combination thereof.

In one embodiment, the drying element is injection molded, 3d printed, or otherwise formed or otherwise formed or attached either over the advancing element or connected or glued to the advancing element. The drying element is any durometer that aids in drying the channel, though in a preferred embodiment, the durometer of the material is between 35 and 75 Shore A. In embodiments, the drying element may be made of any elastomer or any elastic material, including pebax, polyurethane, santoprene, silicone, high or low density polyethylene, EVA and other elastomeric materials. In embodiments, the drying element could be a combination of materials, including a combination of hard and soft materials with varying elasticity.

In embodiments, a version of the drying portion of the invention may include material that can absorb water, such as a sponge, an absorptive cloth or other material that can absorb and hold moisture and water. This material may be attached to the advancing element as a cylinder, as strips of material in singular or various lengths, as overlapping material, as a round ball, or as any other shape that aids in removable of water and moisture from a channel as the advancing element is passed through a channel. This absorptive material may be at the end or beginning of a drying element or interspersed between other drying elements, such as squeegees or fins.

In embodiments, the drying element of the invention may be any shape or form that can displace water and moisture through advancement and withdrawal, including a squeegee, cylinder, series of absorptive strips, venturi or inverted venturi, oblong and round shapes, a ball or spherical shaped drying element.

The invention may include coatings that aid in attracting or repelling water and in navigation by changing levels of friction. The invention may have a lumen that allows air to be blown through the invention to delivery forced air deep inside a channel in close or direct proximity to a channel wall In another aspect, a method for drying one or more lumens within an endoscopic instrument comprises advancing an elongate member having at least one drying member through the lumen within the endoscopic instrument and creating a pressure gradient along a central portion of the drying member. This pressure gradient causes an increase in a relative velocity between the drying member and any air or fluid within the lumen as the drying member is advanced through the lumen. The increased velocity of the fluid or air increases the shear stress between the fluid or air and the lumen wall, thereby creating more force to dry the wall.

In embodiments, the central portion of the drying member comprises a contraction section coupled to the proximal end portion, a diffusion section coupled to the distal end portion and a throat section coupling the diffusion and contraction sections, wherein the throat section has a diameter less than the diameter of the proximal and distal end portions and greater than a diameter of the diffusion and contraction sections.

In embodiments, the method further comprises centering the drying member within the lumen as the drying member is advanced through the lumen. The centering element is preferably smaller than the diameter of the lumen through which the device is being advanced, but has a significant enough size to prevent misalignment and deflection of the navigation element to one side or another of the lumen as it navigates, including as the drying element is pulled or pushed around curves, corners and junctions of various lumens (including Y junctions).

The method comprises introducing a guidance element through a first opening in a lumen of an instrument and advancing an elongate drying device through a second opening in the lumen such that at least a portion of the elongate drying device engages the guidance element. The guidance element engages and couples with the drying device such that the drying device can be withdrawn towards the first opening of the lumen with the guidance element.

In certain embodiments, the endoscope lumen comprises first and second lumens coupled to each other at a junction, such as the Y junction between the biopsy and suction channels in an endoscope. In these embodiments, the method further comprises introducing the guidance element through the first lumen past the junction into the second lumen and advancing the elongate drying device through the second lumen such that the elongate drying device engages the guidance element. The guidance element may then be used to withdraw the drying device past the junction and through the first lumen. This ensures that the drying device dries the biopsy channel, rather than being deflected and continuing past the Y-junction proximally further into the suction channel.

In other embodiments, the endoscope lumen includes a turn or bend having a relatively small radius of curvature that would otherwise be difficult to advance the drying element therethrough. In these embodiments, the guidance element is introduced through a lumen on one side of the turn and advanced therethrough. The drying device is advanced or retracted through the lumen on the other side of the turn until it engages with the guidance element. The guidance element is then withdrawn to pull the drying device through the turn.

The guidance element may comprise a tubular sheath or similar device having a distal end portion configured for engaging an end portion of the cleaning element. In some embodiments, the tubular sheath is removably coupled to the cleaning element. In other embodiments, the tubular sheath may have an inner diameter larger than an outer diameter of the proximal end portion of the elongate drying element, and may be further configured to deflect or otherwise direct the drying element past a junction or other tortuous area in the lumen In certain embodiments, the tip of the guidance element is angled to further conform to the shape of a multi-channel internal junction in the scope. In other embodiments, the end of the navigation element may have a flange that is larger than the entry opening to the specific scope channel where the navigation element is inserted, so that the navigation element cannot be advanced entirely into the channel and result in difficult withdrawal. In an alternative embodiment, the navigation element may not have a flange, but may have a marker, including for example, a pad printed or other line, demarcating the maximum recommended point of advancement of the navigation element into the scope or other channel.

In other embodiments, the cleaning/drying device may have one or more absorbent sponges placed in front of or at the end of the cleaning/drying device or in between one or more of the cylindrical elements to absorb biomatter and debris. The absorbent sponges may be of a single cell configuration or have multiple sponges with different cell configurations to provide scrubbing, absorption, lifting, diffusion of cleaning fluid, or a combination of these attributes. The absorbent sponges may comprise any material that absorbs biomatter, fluid or other debris, such as a polymer, foam, sponge, bamboo, hemp, microfibers, polyurethane, polyvinyl alcohol, or the like. In one embodiment, the cleaning member comprises a sponge-like material, such as cellulose, dry, natural and/or compressed cellulose. In an exemplary embodiment, the material comprises a mixture of cellulose and compressed cellulose that allows the sponge to expand when it is hydrated. Preferably, the material is selected such that the sponge has the ability to expand to at least the internal surface of the lumen, while, in a preferred embodiment, maintaining sufficient absorbability to absorb a volume of material or fluid at least equal to the volume of the segment of the lumen it occupies.

In embodiments, the sponges are soft and atraumatic when immersed in fluid, and expand to a size that is at least sufficient to remove debris from the channel being cleaned (and/or remove moisture and fluid from the channel), and in a preferred embodiment is larger than the channel being cleaned. The sponges may be any shape and size that conforms and aids in cleaning the scope's channel, including by way of example, not limitation, cylindrical in shape, spiral in shape, conical, triangular, square or any combination thereof.

In embodiments, the cleaning member or the drying member may have more than one cylindrical element placed in close proximity to another, including one or more elements, cylindrical or other shapes, with a spacing that does not create variable pressure on average between the elements, followed by or, alternatively, before, a cylindrical element with a spacing between the next cylindrical element that creates variable pressure between the cleaning/drying member and the wall of the channel being cleaned. In embodiments, a series of cylindrical elements may be organized in various spacing to create variable pressure between the cylindrical elements and certain spacing to create constant pressure between the cylindrical elements.

In other embodiments, the devices disclosed herein may be used to dry and/or clean in-dwelling devices. In these embodiments, the devices may further include a sheath or similar structure to cover the cleaning and/or drying elements and/or the navigation element while translating through the lumen of the instrument to avoid disturbing biomatter and any accumulated biofilm therein. The system may also include a measuring device, such as a marker on the navigation element or a separate elongated element to confirm positioning of the device within the lumen of the catheter. The polymers that form the cleaning and/or drying elements may expand once the sheath has been withdrawn. Alternatively, electrically responsive polymers may be used to change shape and enlarge with the application of energy, causing them to expand and contact the walls of the catheter, or at least in part.

The device may include a coating that is hydrophobic. In yet another embodiment, the device is superhydrophobic and/or oleophobic. In even still another embodiment, the device is anti-infective and hydrophobic. Further yet in another embodiment, the device is anti-infective and superhydrophobic. In further still another exemplary embodiment, anti-inflammatory coatings are incorporated into the device. In other embodiments, the anti-inflammatory coatings may comprise a hydrophilic material, or a coating is hydrophilic.

It is to be understood that both the foregoing general description and the following detailed description are exemplary and explanatory only and are not restrictive of the description. Additional features of the description will be set forth in part in the description which follows or may be learned by practice of the description.

BRIEF DESCRIPTION OF THE DRAWINGS

The accompanying drawings, which are incorporated in and constitute a part of this specification, illustrate several embodiments of the description and together with the description, serve to explain the principles of the description.

FIG. 7A is a side view of a cleaning and/or drying device including multiple cleaning and/or drying elements coupled to each other;

FIG. 7B is a side view of another embodiment of a cleaning and/or drying device with multiple cleaning and/or drying elements;

FIGS. 11A-11D illustrate further alternative embodiments of a cleaning and/or drying device;

FIGS. 21A and 21B illustrate alternative embodiments of the cleaning and/or drying device of FIG. 19;

DESCRIPTION OF THE EMBODIMENTS

Figure 1:
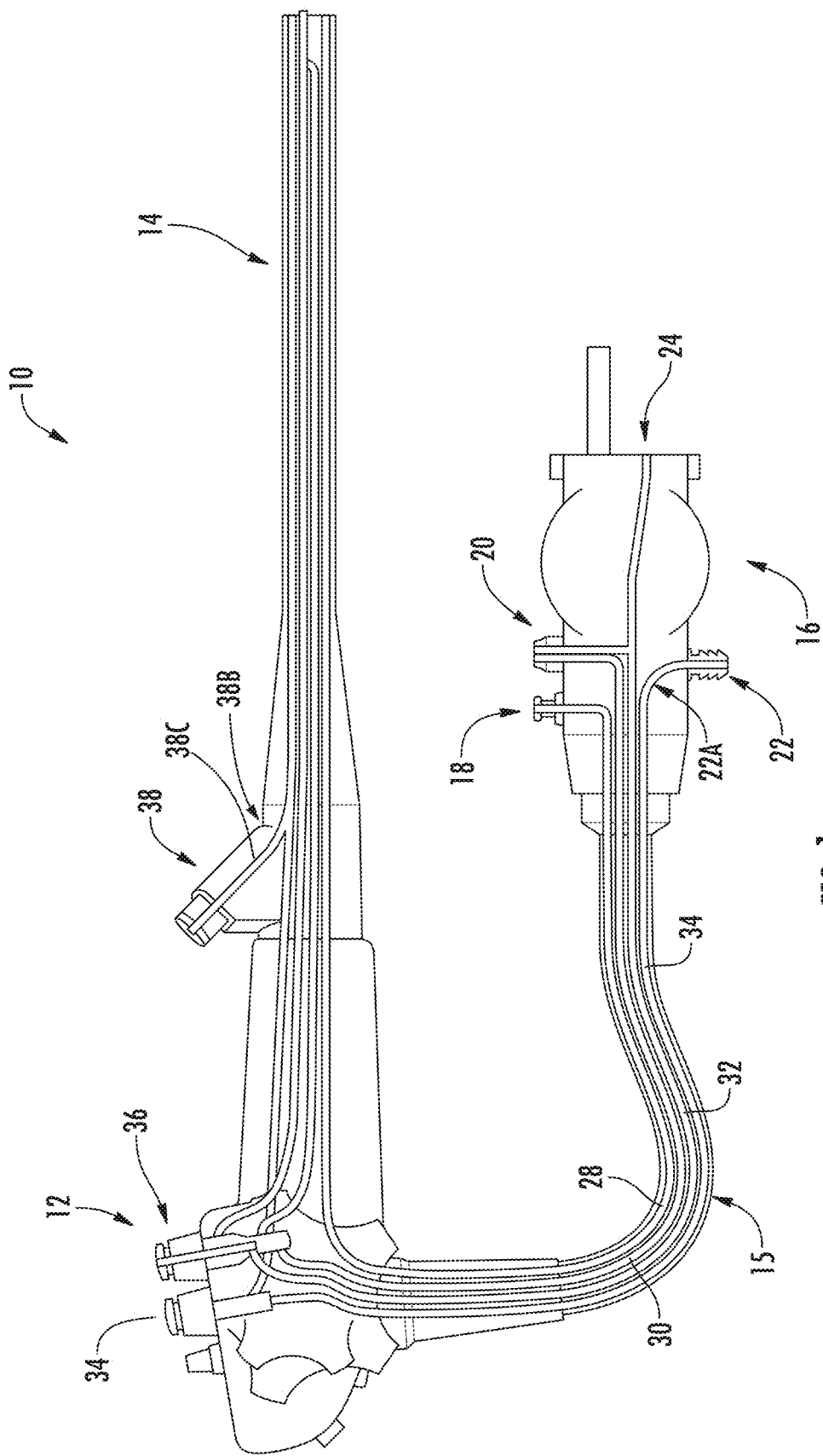
FIG. 1 illustrates a representative endoscope for use with the disinfection systems and methods disclosed herein.

This description and the accompanying drawings illustrate exemplary embodiments and should not be taken as limiting, with the claims defining the scope of the present description, including equivalents. Various mechanical, compositional, structural, and operational changes may be made without departing from the scope of this description and the claims, including equivalents. In some instances, well-known structures and techniques have not been shown or described in detail so as not to obscure the description. Like numbers in two or more figures represent the same or similar elements. Furthermore, elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment. Moreover, the depictions herein are for illustrative purposes only and do not necessarily reflect the actual shape, size, or dimensions of the system or illustrated components.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

While the following description is primarily directed to an endoscope and a device for cleaning and/or drying the endoscope, it should be understood that the features of the presently described disinfection system may be readily adapted for use with a variety of reusable or disposable endoscopic instruments and devices that include internal lumens or other internal spaces, such as endoscopes, trocars, cannulas, dilatation devices, Foley catheters, guidewires, central venous catheters, bipolar or monopolar electrosurgical or ultrasonic devices, ventilation machines, respirators, CPAP and other positive airway machines, robotic and remote surgery equipment, arterial lines, drainage catheters, peripherally inserted central catheters, endotracheal tubes, feeding tubes, and other devices that in-dwell, penetrate and/or navigate in the body.

The term "endoscope" as used herein refers generally to any scope used on or in a medical application, which includes a body (human or otherwise) and includes, for example, a laparoscope, arthroscope, colonoscope, gastroscope, duodenoscope, endoscopic ultrasound scope, bronchoscopes, enteroscope, cystoscope, laparoscope, laryngoscope, sigmoidoscope, thoracoscope, cardioscope, and saphenous vein harvester with a scope, whether robotic or non-robotic, or in a non-medical application.

When engaged in remote visualization inside the patient's body, a variety of scopes are used. The scope used depends on the degree to which the physician needs to navigate into the body, the type of surgical instruments used in the procedure and the level of invasiveness that is appropriate for the type of procedure. For example, visualization inside the gastrointestinal tract may involve the use of endoscopy in the form of flexible gastroscopes and colonoscopes and specialty duodenum scopes with lengths that can run many feet and diameters that can exceed 1 centimeter. These scopes can be turned and articulated or steered by the physician as the scope is navigated through the patient. Many of these scopes include one or more working channels for passing and supporting instruments, fluid channels and washing channels for irrigating the tissue and washing the scope, insufflation channels for insufflating to improve navigation and visualization and one or more light guides for illuminating the field of view of the scope.

Smaller and less flexible or rigid scopes, or scopes with a combination of flexibility and rigidity, are also used in medical applications. For example, a smaller, narrower and much shorter scope is used when inspecting a joint and performing arthroscopic surgery, such as surgery on the shoulder or knee. When a surgeon is repairing a meniscal tear in the knee using arthroscopic surgery, a shorter, more rigid scope is usually inserted through a small incision on one side of the knee to visualize the injury, while instruments are passed through incisions on the opposite side of the knee. The instruments can irrigate the scope inside the knee to maintain visualization and to manipulate the tissue to complete the repair Other scopes may be used for diagnosis and treatment using less invasive endoscopic procedures, including, by way of example, but not limitation, the use of scopes to inspect and treat conditions in the lung (bronchoscopes), mouth (enteroscope), urethra (cystoscope), abdomen and peritoneal cavity (laparoscope), nose and sinus (laryngoscope), anus (sigmoidoscope) and other aspects of the gastrointestinal tract (gastroscope, duodenoscope, colonoscope), chest and thoracic cavity (thoracoscope), and the heart (cardioscope). In addition, robotic medical devices rely on scopes for remote visualization of the areas the robotic device is assessing and treating.

These and other scopes may be inserted through natural orifices (such as the mouth, sinus, ear, urethra, anus and vagina) and through incisions and port-based openings in the patient's skin, cavity, skull, joint, or other medically indicated points of entry. Examples of the diagnostic use of endoscopy with visualization using these medical scopes includes investigating the symptoms of disease, such as maladies of the digestive system (for example, nausea, vomiting, abdominal pain, gastrointestinal bleeding), or confirming a diagnosis, (for example by performing a biopsy for anemia, bleeding, inflammation, and cancer) or surgical treatment of the disease (such as removal of a ruptured appendix or cautery of an endogastric bleed).

Referring now to FIG. 1, a representative endoscope 10 includes a proximal handle 12 adapted for manipulation by the surgeon or clinician coupled to an elongate shaft 14 adapted for insertion through an endoscopic or percutaneous penetration into a body cavity of a patient. Endoscope 10 further includes a fluid delivery system 16 coupled to handle 12 via a universal cord 15. Fluid delivery system 16 may include a number of different tubes coupled to internal lumens within shaft 14 for delivery of fluid(s), such as water and air, suction, and other features that may be desired by the clinician to displace fluid, blood, debris and particulate matter from the field of view. This provides a better view of the underlying tissue or matter for assessment and therapy. In the representative embodiment, fluid delivery system 16 includes a water-jet connector 18, water bottle connector 20, a suction connector 22 and an air pipe 24. Water-jet connector 18 is coupled to an internal water-jet lumen 28 that extends through handle 12 and elongate shaft 14 to the distal end of endoscope 10. Similarly, water bottle connector 20, suction connector and 22 air pipe 24 are each connected to internal lumens 30, 32, 34 respectively, that pass through shaft 14 to the distal end of endoscope 10.

Proximal handle 12 may include a variety of controls for the surgeon or clinician to operate fluid delivery system 16. In the representative embodiment, handle 12 include a suction valve 34, and air/water valve 36 and a biopsy valve 38 for extracting tissue samples from the patient. Suction channel 34 extends from suction connector 22, where it creates a relatively tight turn or bend 22A through universal cord 15 into handle 12. Suction channel 34 then extends through shaft 14 to the distal end of endoscope 10. As suction channel 34 passes biopsy valve 38, it creates an internal Y junction 38B with the channel 38C extending into biopsy valve 38. This Y junction 38*b* creates challenges for cleaning and/or drying suction channel 34 with conventional devices, as discussed in more detail below.

Handle 12 may in certain embodiments also include an eyepiece (not shown) coupled to an image capture device (not shown), such as a lens and light transmitting system. The term "image capture device" as used herein also need not refer to devices that only have lenses or other light directing structure. Instead, for example, the image capture device could be any device that can capture and relay an image, including (i) relay lenses between the objective lens at the distal end of the scope and an eyepiece, (ii) fiber optics, (iii) charge coupled devices (CCD), (iv) complementary metal oxide semiconductor (CMOS) sensors. An image capture device may also be merely a chip for sensing light and generating electrical signals for communication corresponding to the sensed light or other technology for transmitting an image. The image capture device may have a viewing end—where the light is captured. Generally, the image capture device can be any device that can view objects, capture images and/or capture video.

In some embodiments, endoscope 10 includes some form of positioning assembly (e.g., hand controls) attached to a proximal end of the shaft to allow the operator to steer the scope. In other embodiments, the scope is part of a robotic element that provides for steerability and positioning of the scope relative to the desired point to investigate and focus the scope.

Figure 2:
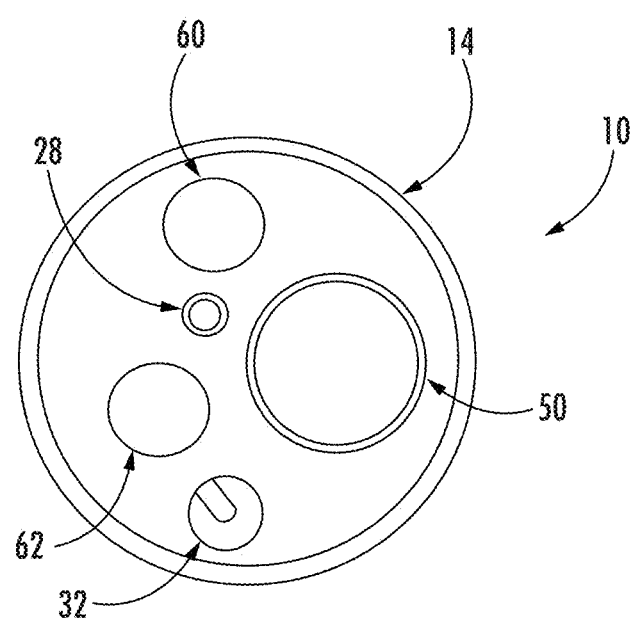
FIG. 2 is a cross-sectional view of a representative endoscope, showing one or more lumens within the endoscope.

As shown in FIG. 2, endoscope 10 may further include a camera lens 62, a scope washer 32, and a light source 60 for providing a view of the surgical site in the patient, and a biopsy channel 50 for passing instruments therethrough. The biopsy channel 50 permits passage of instruments down the shaft 14 of endoscope 10 for removing tissue. Biopsy channel 50 may also function as a working channel for other instruments to pass through endoscope 10 for assessment and treatment of tissue and other matter. Such instruments may include cannulas, catheters, stents and stent delivery systems, papillotomes, wires, other imaging devices including mini-scopes, baskets, snares and other devices for use with a scope in a lumen. Alternatively, endoscope 10 may include a separate working channel for these instruments.

Figure 3:
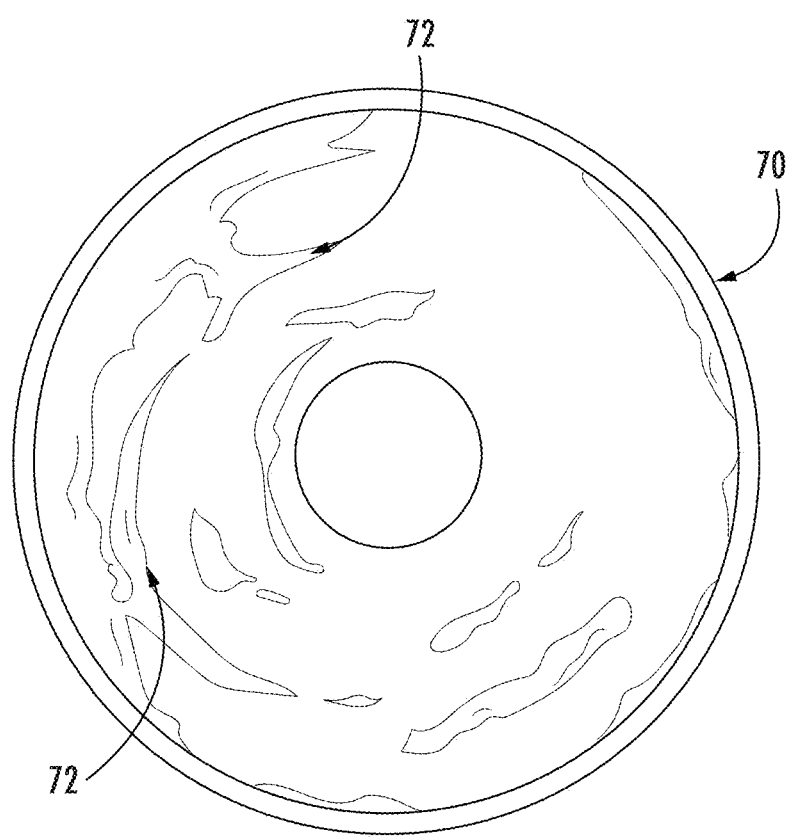
FIG. 3 illustrates damage that may occur to a representative endoscope during use and/or cleaning with conventional devices.

FIG. 3 illustrates an internal lumen 70, such as a biopsy channel, working instrument channel or water/air channel, of a representative endoscope. As shown, the internal surface of lumen 70 has been damaged either during previous procedures, or by conventional cleaning devices. As such, lumen 70 includes numerous defects 72 that provide extremely small areas for harboring pathogens, biomatter, tissue or other debris therein. These defects 72 are very difficult to clean and dry with conventional devices. Moreover, as they harbor biomatter, the biomatter protects the pathogens therein from conventional sterilization and disinfection techniques.

An exemplary cleaning and/or drying device will now be described. The cleaning and/or drying device comprises an elongate shaft and a cleaning and/or drying member disposed on one portion of shaft. The cleaning and/or drying member may be removably attached to, or permanently affixed to, the shaft. The shaft may comprise any suitable material that provides sufficient rigidity for the shaft to be advanced through a lumen of an endoscope. The elongate shaft has an outer diameter sized to fit within, and translate through, the internal lumens in endoscope 10. In the exemplary embodiment, the shaft will have an outer diameter in the range of about 0.5 to about 5 mm, preferably about 1 to 4 mm.

In certain embodiments, the device includes a pull cable configured to withdraw or advance elongate the shaft within an internal lumen in endoscope 10. Device may also include an energy source and a motor for advancing and/or withdrawing the elongate shaft. Of course, it will be recognized that the elongate shaft may be manually translated through internal lumen via a proximal handle or suitable actuator (i.e., no motor).

Figure 4:
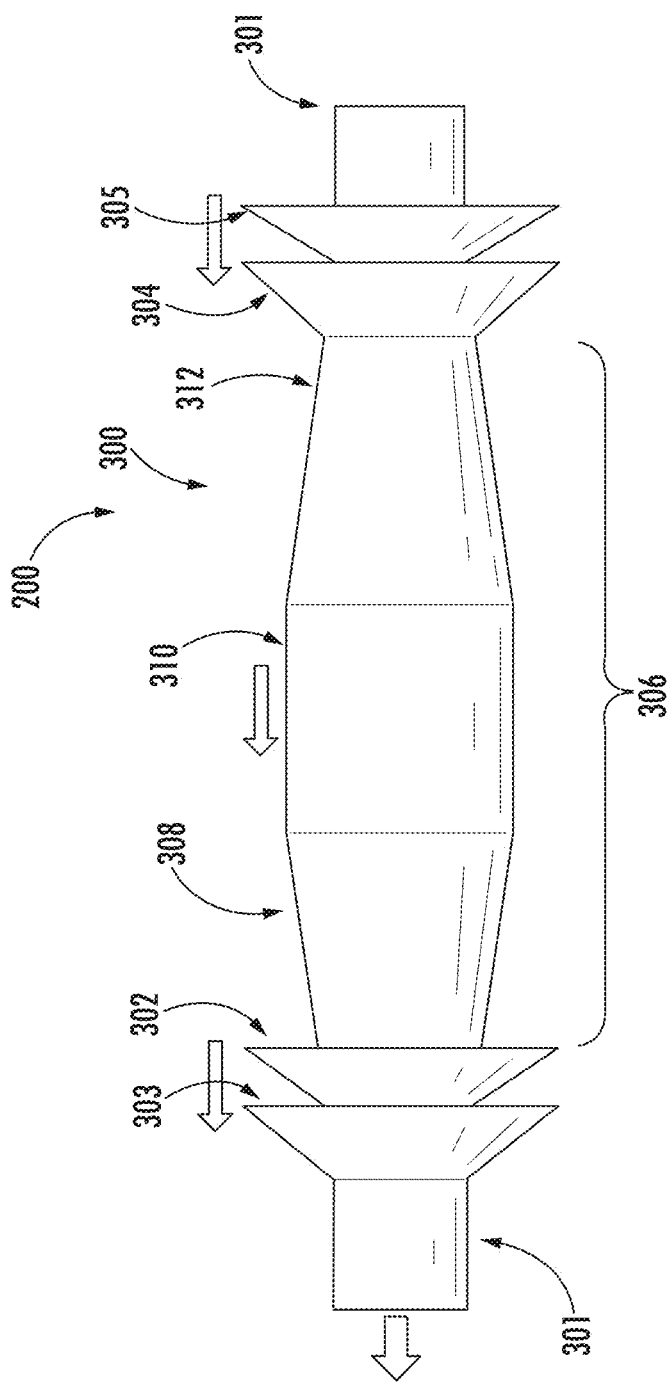
FIG. 4 is a side view of an exemplary embodiment of a cleaning and/or drying element.

Referring now to FIG. 4, a portion of a cleaning and/or drying device 200 according to certain embodiments will now be described. Cleaning and/or drying device 200 includes one or more cleaning and/or drying element(s) 300, which are attached to a pushing and pulling element, such as a navigation element 301 (only a portion of which is shown in FIG. 4). Navigation element 301 can be advanced from the proximal end to the distal end (or vice versa) of any internal lumen with the endoscope. For example, in one embodiment, navigation element 301 is advanced from the scope's biopsy channel to the distal end of the biopsy channel in order to exit from the biopsy channel and connect to a cleaning and/or drying element. Navigation element 301 may also be advanced from the proximal end of the scope's biopsy channel to the distal end of the biopsy channel (or suction channel, as applicable) in order to exit from the biopsy channel and connect to a cleaning and/or drying element, or alternatively, advanced and pulled through the channel from the proximal end of the biopsy channel (or suction channel) to the distal end. This pushing and/or pulling navigation element is attachable and in embodiments also detachable, and in other embodiments may be permanently attached to cleaning and/or drying element 300.

As shown in FIG. 4, cleaning and/or drying element 300 is a separate element that is connectible to navigation element 301 such that navigation element 301 can be passed through an internal lumen of an endoscopic device. For example, navigation element 301 can be advanced from the proximal entry to biopsy channel 38C down biopsy channel 38C, emit from the distal end of the biopsy channel and then connect to cleaning and/or drying element 300 so that the entire system can then be pulled from the distal end of the scope up the biopsy channel to then exit the proximal end of the biopsy channel. This approach allows the biopsy channel to be successfully cleaned without creating the problems with current technologies that accumulate debris and biomatter and push this out the distal end of the biopsy channel, resulting in additional contamination at the most difficult to clean part of the scope. This approach also allows for the successful drying of the biopsy channel.

The unique ability to advance a navigation element and then connect to a cleaning and/or drying element at the distal end of the scope and withdraw the navigation element from the distal end to the proximal end of the scope provides for successful cleaning and/or drying without increasing the contamination level of the distal end of the scope, which is the most difficult to clean part of the scope, or otherwise enter a deflection tube to pass a Y junction in a scope to enable distal to proximal cleaning and/or drying with passage through a preferred side of a Y junction. This approach to cleaning and/or drying can also be used to clean or dry other lumens in the scope, including the suction channels and the air/water channel(s), as applicable.

In other embodiments, navigation element 301 and cleaning and/or drying element 300 are adhered to each other and advanced or retracted through one or more lumens together. Navigation element 301 and cleaning and/or drying element 300 may be manufactured as one integral device, or they may be manufactured separately and attached to each other prior to use.

Channel element 300 comprises proximal and distal end portions, that are preferably at least two channel wall contact elements 302, 304, which are typically cylindrical in shape in order to match the shape of the endoscope's channels. Wall contact element 302, 304 create a consistent circumferential contact with the interior wall of an endoscope channel, such as a biopsy or suction channel. In certain embodiments, channel element may include secondary wall contact elements 303, 305 (or additional ones if desired) to enhance the engagement between the wall contact elements and the internal lumen walls and to ensure that the variable pressure region (discussed below) is effective.

Channel contact elements 302, 304 may comprise any suitable shape that substantially conforms to the walls of the internal lumen. In certain embodiments, channel contact elements 302, 304 preferably have a substantially circumferential, cylindrical or conical shape with at least one portion of the element 302, 304 having a diameter approximately equal to or slightly larger than the diameter of the internal lumen. In an exemplary embodiment, the largest diameter of channel contact elements 302, 204 is about 1 to about 1.5 times the diameter of the internal lumen, preferably about 1 to about 1.23 times this diameter. For example, if the diameter of the internal lumen is about 5 mm, the largest diameter portion of elements 302, 304 may be about 4.2 to 5.5 mm, preferably about 5 mm. This additional size allows elements 302, 304 to deform slightly as they pass through the lumen, ensuring that they will remain in contact with the lumen.

In certain embodiments, the contact elements are substantially conical such that they angle downwards in the proximal direction (or the direction of travel of the cleaning and/or drying device through the lumen of the endoscope), as shown in FIG. 4. This configuration allows contact elements 302, 304 to create a contact friction force along the internal walls of lumen so that they can slide along the walls of internal lumen of the endoscope without getting caught or otherwise stuck in the lumen, while still ensuring that at least a portion of contact elements 302, 304 remain in contact with the lumen. In an exemplary embodiment, contact elements 302, 304 are about 0.75 mm and taper to about 0.5 mm at their tips (or the point of contact with the internal wall of the lumen).

Cleaning and/or drying element 300 further includes a variable pressure region 306 between wall contact elements 302, 304. Variable pressure region 306 is designed to create variable pressure between the two circumferential contact elements 302, 304 and the wall of the channel being cleaned. Thus, as the cleaning and/or drying member is advanced inside a channel and the scope and its channels are submerged in cleaning fluid (as required by scope manufacturers, which may be saline or any other biocompatible material safe to use with an in-dwelling catheter), the variable pressure design between the two circumferential elements creates a venturi effect between the cleaning and/or drying element and the walls of the endoscope channel when the cleaning and/or drying element is moved through the lumen. As a result, when the cleaning fluid flows across the variable pressure area, this impacts the fluid flow as it transfers from an area of high pressure across an area of low pressure and then back to another area of high pressure between the two cylindrical elements. This directs the cleaning fluid at the channel walls with an increased velocity and force, similar to the venturi effect created when putting one's thumb partially over the end of a garden hose to increase the force of the water emitting from the hose.

When used for drying a lumen, the forces created by the variable pressure region 306 increase the drying performance of element 300. These forces allows the cleaning and/or drying element to substantially remove all fluid and moisture from within the lumen.

Alternatively, variable pressure region 306 may be designed to create areas of low pressure on either end of region 306 with an area of high pressure there between. In this embodiment, when the cleaning fluid or air flows across the variable pressure area, this impacts the fluid or air flow as it transfers from an area of low pressure across an area of high pressure and then back to another area of low pressure between the two cylindrical elements.

As shown in FIG. 4, variable pressure region 306 comprises a contraction section 308 coupled to the proximal contact element 302, a diffusion section 312 coupled to the distal contact element 304 and a throat section 310 coupling the diffusion and contraction sections 308, 310. The throat section 320 has a diameter less than the diameter of the contact elements 302, 204 and greater than a diameter of the diffusion and contraction sections 308, 310. This design enhances the performance of the cleaning fluid (or air) by turning the fluid (or air, as applicable) from a static point of interaction with the walls of a scope channel, to a dynamic point of interaction where the lifting action of the cleaning fluid's chemistry (or air in the case of drying) is enhanced through cleaning and/or drying member's direction of the fluid or air at the walls of the scope channel with pressure.

Variable pressure region 306 may include an inverted, partial venturi shape, a parabolic shape, a variable slope shape or such other shape that creates variable pressure between the two cylinders and the wall of the channel being cleaned, thereby increasing the force by which the cleaning fluid or air is projected at the channel wall when the cleaning and/or drying member is advanced.

In an exemplary embodiment, throat section 310 is substantially cylindrical. The contraction section 308 preferably increases in diameter from the contact section 302 to the throat section 310 and the diffusion section 312 preferably decreases in diameter from the throat section 310 to contact section 304, thereby creating a venturi effect between the distal and proximal end portions 302, 304 of the cleaning and/or drying element 310.

In a preferred embodiment, variable pressure region 306 has an inverted, partial venturi shape with three distinct areas of various spacing from the wall of the scope channel, which creates accelerated hydrodynamic action or similar action with air to project the cleaning fluid (or air) at the channel wall to clean more effectively. These areas include a contraction section 308, which is the start of the area where cleaning fluid (or air) is present on the other side of the first cylindrical element. The contraction section 308 is the start of the area in which fluids accumulate and are subject to changing pressure as the space available for the fluid varies and becomes smaller as cleaning and/or drying element 300 is advanced and the fluids (or air) are directed into the throat section 310 that further alters the pressure between the cleaning and/or drying element and the channel wall. The throat section 310, wherein the shape available for the fluid is reduced further in a manner that changes the pressure on the fluid (or air) compared to the pressure on the fluid (or air) in the contraction section, creates an acceleration of the fluid as cleaning and/or air as the drying element 300 is advanced; followed by a diffusion section 312 which supports the diffusion of the cleaning fluid (or air) at an accelerated speed as it exits the throat section. Collectively, these sections between the cylindrical elements create a hydrodynamic force for cleaning fluids sufficient to remove bacteria, biomatter and debris from the walls of the channels of the endoscope or a similar force with air to displace water and moisture to dry the channel of the endoscope. This hydrodynamic force applied to air is also sufficient to remove substantially all moisture and fluid from the lumens during a drying process.

The angle of the slope of the contraction section 308 (defined as the angle made between the vertical section of conical section 302 and the sloped portion of contraction section 308) may vary depending on the diameter of the channel being cleaned, the viscosity of the fluid (or thickness of air) and other factors and should be sufficient to support a variable pressure flow of cleaning fluid or air between the cylinders when the cleaning and/or drying element is advanced. In certain embodiments, the contraction section defines an angle with the proximal end portion (i.e., contact section 302) that is about 4 degrees to about 85 degrees, preferably between about 15 degrees to about 30 degrees. Similarly, the diffusion section defines an angle with the distal end portion (i.e., contact section 304) that is about 4 degrees to about 85 degrees, preferably about 15 degrees to about 30 degrees. Of course it will be recognized that various pressure regions 306 may have more than one slope, a curved shape, a variable shape or such other shape which assists in varying the pressure between the two cylindrical elements 302, 304.

Likewise, the angle between contraction and diffusion sections 308, 312 and throat section 310 may vary depending on the diameter of the channel being cleaned, the viscosity of the fluid or air and other factors, and should be sufficient to support a variable pressure flow of cleaning fluid or air between the cylinders when the cleaning and/or drying element is advanced. In certain embodiments, this angle is about 10 degrees to about 50 degrees, preferably about 15 degrees to about 30 degrees and more preferably about 20 degrees to about 25 degrees.

The length and diameter of each section of variable pressure region 306 are preferably selected to optimize the venturi effect and will vary based on the diameter of the internal lumen, the viscosity of the fluid or air and other factors. For example, in a lumen having a diameter of about 4.2 mm, the length of throat section 310 may be about 2 mm to 10 mm, preferably about 3 mm to 5 mm, and more preferably about 4 mm. The outer diameter of throat section 310 will also depend on the diameter of the inner lumen as well as the diameter of contraction and diffusion sections 308, 312. In certain embodiments, throat section 310 is less than the diameter of the internal lumen, but greater than 50% of the diameter of the lumen, preferably greater than about 60% of the diameter of the lumen, and more preferably equal to or greater than about 70% of the diameter of the lumen (e.g., about 3 mm in a lumen having an inner diameter of about 4.2 mm).

The outer diameter of navigation element 301 is preferably less than the diameter of throat region 310. In an exemplary embodiment, this diameter is less than about 2.5 mm, preferably less than about 2.0 mm, and more preferably about 1.75 mm.

The venturi effect created by variable pressure region 306 impacts the fluid flows (and air flows, as applicable) as it transfers from an area of high pressure across an area of low pressure between the two cylindrical elements, and then back to another area of high pressure, such that the cleaning fluid or air is directed at the channel walls with an increased force, similar to the venturi effect created when putting one's thumb partially over the end of a garden hose to increase the force of the water emitting from the hose. This variable pressure design means that when cleaning and/or drying element 300 is attached and withdrawn or pulled with the navigation element through a scope channel, the cleaning fluid or air in the channel and between the cylindrical elements and the wall of the endoscope channel is moved across the variable pressure area between the two cylindrical spheres, creating a jetting of the cleaning fluid to pressure wash the channel walls of the endoscope channel with the cleaning fluid, or pressure of air to dry the channel walls.

This unique capability has the powerful effect of enhancing the performance of the cleaning fluid by turning the fluid from a static point of interaction with the walls of a scope channel, to a dynamic point of interaction where the lifting action of the cleaning fluid's chemistry is enhanced through the cleaning and/or drying element's direction of the fluid (or air) at the walls of the scope channel with pressure. Computational modeling using fluid and pressure dynamics shows that, in embodiments, the application of inverted venturi principles to create variable pressure between two cylindrical elements directs the cleaning fluid (or air) at all of the channel wall with hydrodynamic (or air) pressures of variable and increasing force to create a new, highly effective cleaning and/or drying capability that can remove debris, biomatter and bacteria from the channel, or dry, including addressing changes in the surface topography of the channel due to the ability to direct the cleaning fluid with hydrodynamic force (or air) into any scratches and crevasses in the scope channel.

Computational modeling and test data assessing the performance of the cleaning and/or drying element indicates this innovation impacts the direction and force of the cleaning fluid or air, changing the fluid from a static soaking detergent or air, into an active pressure washing and cleaning and/or drying modality where the cleaning and/or drying element's variable pressure design creates a direct and beneficial fluid or air force against the wall of the channel. This pressure washing or air drying, in the form of a directed, hydrodynamic fluid force or air against the channel walls, is a measurable force we call fluid or air friction force.

In embodiments, this variable pressure region 306 causes the cleaning fluid or air to be projected at the channel wall with a pressure that exceeds the adhesion force of bacteria or moisture that may attach to the wall, creating a powerful benefit that is not present with existing brushing technologies. This capability enhances cleaning or drying, just as using a detergent with a pressure washer enhances the cleaning of an external surface, such as using a pressure washer with detergent to remove contaminants from the side of a building or a walkway, or an air dryer. This innovation enhances the cleaning fluid or drying in a new and powerful way, plus adds other capabilities in its design, changing channel cleaning performance so that the successful cleaning of a scope channel is not dependent on the performance of a single element, such as the unpredictable wall contact force of a bristle brush or a pull thru cleaner, or the static performance of a cleaning detergent, or drying based on evaporation over time. The variable pressure region 306 of cleaning/drying element 300 creates hydrodynamic/air pressure that directs cleaning detergent/air at the wall of the scope's channels. Cleaning or drying action using the hydrodynamic pressure force to enhance cleaning fluid performance or air drying and doing this in combination with mechanical pressure force is the best way to achieve consistent, predictable and repeatable success with removing biomatter and debris or moisture through drying from the channels of endoscopes, or other endoscopic instruments, without injury to these important channels.

The combination of cylindrical elements and a variable pressure element is important for creating the hydrodynamic or air force and it adds additional cleaning and/or drying force, by making atraumatic contact with the walls of the scope channel. These cylindrical elements add a channel wall contact pressure force as an additional cleaning or drying modality to remove debris and biomatter from the channel wall or to dry as an additional, complementary cleaning or drying capability that works in concert with the variable pressure element between the cylinders.

When the cleaning element is advanced through a lumen having cleaning fluid or air therein, the variable pressure region of the cleaning element is configured to generate fluid or air pressure against the internal wall of the lumen. In certain embodiments, the variable pressure region is configured to generate a peak pressure of at least about 75 Pa in at least one area between the distal and proximal end portions of the cleaning element. This peak pressure is preferably at least 100 Pa and more preferably at least 125 Pa. In an exemplary embodiment, the peak pressure may be approximately 150 Pa. This direct pressure against the lumen wall is sufficient to remove substantially all biomatter or moisture from the internal surface of the lumen.

The variable pressure region of the cleaning element is configured to generate an average or mean pressure across the distance between the proximal and distal end portions of the cleaning element of at least about 10 Pa, preferably about 20 Pa and more preferably about 30 Pa. In an exemplary embodiment, the mean pressure is about 36 Pa.

The variable pressure region of the cleaning/drying element is also configured to generate a peak shear stress of at least about 4 Pa in at least one area between the distal and proximal end portions of the cleaning element, preferably at least about 5 Pa and more preferably at least about 8 Pa. The average or mean shear stress across the distance between the proximal and distal end portions of the cleaning element is at least about 1 Pa, preferably about 2 Pa and more preferably greater than 2.5 Pa. In an exemplary embodiment the mean shear stress is about 2.8 Pa.

The variable pressure region of the cleaning/drying element is configured to generate a substantially high pressure across a relatively large coverage area between the proximal and distal ends of the cleaning element. This increases the amount of time that the inner surface of the lumen is subjected to this substantially high pressure, thereby increasing the amount of biomatter or moisture that can be removed with the device. For definitional purposes, Applicant has defined the Peak Cleaning Pressure Coverage Area (PPAC™) as the distance between the proximal and distal ends of the cleaning element in which the variable pressure region generates a pressure above 50 Pa. In certain embodiments, the cleaning/drying element is configured to generate a PPAC in at least about 10% of this distance, preferably at least about 25% of this distance and more preferably at least about 40% of this distance.

The variable pressure region of the cleaning/drying element is also configured to generate at least some positive pressure against the internal lumen across a relatively large coverage area between the proximal and distal ends of the cleaning element. This increases the amount of time that the inner surface of the lumen is subjected to at least some cleaning or drying pressure, thereby increasing the amount of biomatter or moisture that can be removed with the device. For definitional purposes, Applicant has defined the Positive Pressure Cleaning Area (+PAC™) as the distance between the proximal and distal ends of the cleaning element in which the variable pressure region generates a positive pressure (i.e., above zero). In certain embodiments, the cleaning/drying element is configured to generate a +PAC in at least about 25% of this distance, preferably at least about 50% of this distance and more preferably at least about 75% of this distance. In an exemplary embodiment, the +PAC may be as high as 81%.

In embodiments, a ratio of contraction may be determined between the contraction section 308 and the throat section 310, though the ratio may change and vary depending on the diameter of the scope channel being cleaned, the durometer of the material used for cleaning element 300, the projected speed and force applied to withdraw the navigation element 301 after it is attached to cleaning element 300 or otherwise advanced through the channel, the viscosity of the fluid used for cleaning or air for drying, the desired fluid friction force of the cleaning fluid or air projected by cleaning element 300 and the direction of the flow exiting the throat section, including whether a narrow or broader flow is desired with the design.

The overall length of variable pressure region 306 will depend on a variety of factors, including but not limited to, the diameter of the lumen, the viscosity of the fluid or air within lumen, the specific shape and angles of contraction, 308, throat 310 and diffusion 312 sections and the like. In an exemplary embodiment, the length of variable pressure region is about 5 mm to about 20 mm, preferably about 10 mm.

Additionally, the angle of the surface of the diffusion section 312 may be a single plane or multiple planes. In embodiments the angle of the surface of the diffusion section 312 increases the space between the wall of the endoscope channel and cleaning element 300, in embodiments, in the diffusion section. This variation allows the fluid or air to accelerate at a higher pressure and velocity out of the throat section to create elevated and increasing fluid or air pressure force against the walls of the endoscope channel as cleaning element 300 is advanced through the endoscope channel.

In embodiments, cleaning and/or drying element 300 may not have a three section arrangement and instead could have other shapes and forms intended to modify the pressures between the two cylinders and create elevated pressure sufficient to remove biomatter and debris from the walls of the scope's channels or to dry the walls of the scope's channels.

In embodiments, the delivery of hydrodynamic force or air drying force covers a meaningful area of the scope's channel between the two cylindrical elements, such that the application of the elevated force caused by cleaning element 300 is not narrow and instead involves elevated force that is broader and thereby has greater success at removing biomatter and debris, or drying. In certain embodiments, the hydrodynamic force exceeds the attachment force of bacteria commonly encountered in the medical procedures, or the adhesion force of moisture against the channel.

Figure 5:
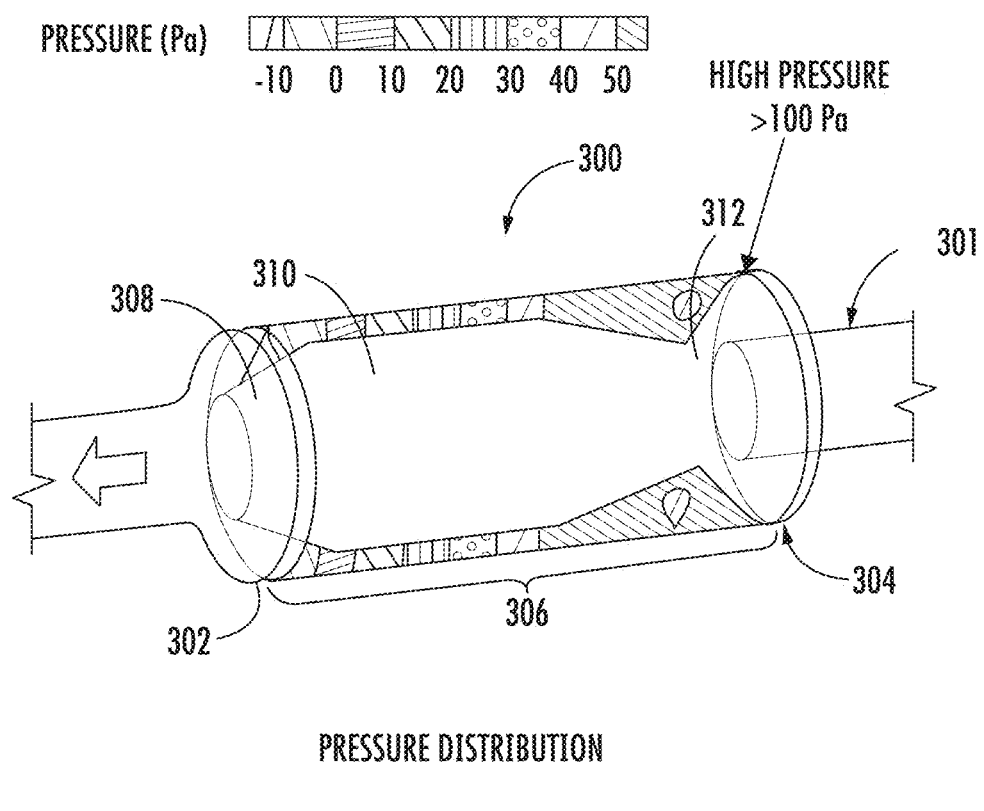
FIG. 5 illustrates a fluid pressure distribution created by the cleaning and/or drying element of FIG. 4.
Figure 6B:
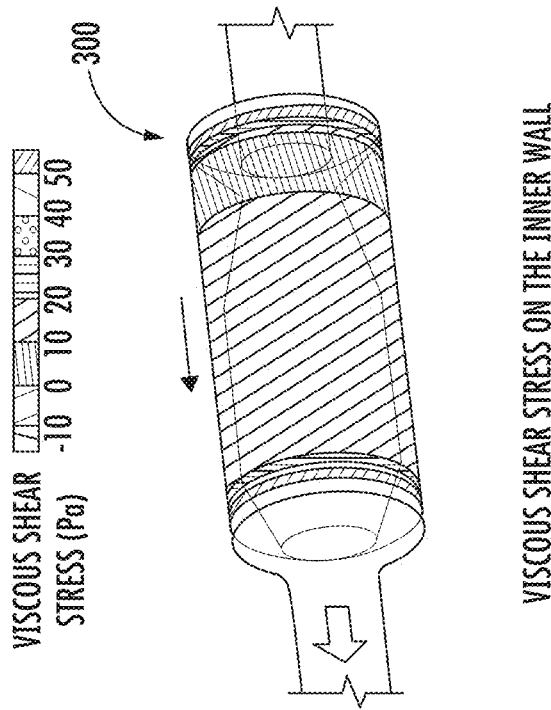
FIGS. 6A and 6B illustrate direct and shear stress pressures created against and along an internal lumen with the cleaning and/or drying element of FIG. 4.
Figure 6A:
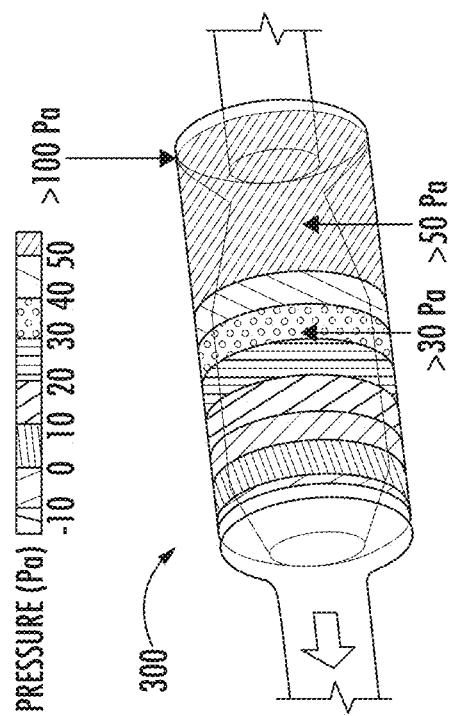

FIGS. 5 and 6 illustrate the overall flow pattern of fluid or air flowing past cleaning/drying element 300 within an internal lumen of an endoscope device. As shown in FIGS. 5 and 6A, the overall pressure distribution between cleaning/drying element 300 and the internal walls of the lumen creates a relatively low pressure region around contraction section 308, a higher pressure region around throat section 310 and even higher pressure region around diffusion section 312. The hydrodynamic or air force is directed at a force level greater than 10 Pa across at least 50% of the distance between the two cylindrical elements 302, 304. In a preferred embodiment, the hydrodynamic or air force is directed at a level greater than 10 Pa across at least 75% of the distance between the two cylindrical elements 302, 304. In an exemplary embodiment the force is greater than 20 Pa across at least 50% of the distance between elements 302, 304.

FIGS. 5 and 6A also illustrate the peak pressure formed around diffusion section 312. As shown, the peak pressure can reach as high as 100 Pa or greater in this region. In certain embodiments, the pressure in the entire diffusion section 312 is greater than 50 Pa.

The relative fluid or air velocity increases from one end of cleaning/drying element 300 to another as cleaning element 300 is advanced proximally (or distally depending on the direction of cleaning). In addition, diffusion section 312 creates swirling fluid or air (not shown) in diffusion section 312 that increases the pressure applied by the fluid or air to the internal walls of the lumen.

FIG. 6B further illustrates the viscous shear stress created by cleaning/drying element 300 along the internal wall of the lumen as fluid passes between element 300 and internal wall. As shown, the shear stress is greater near cylindrical elements 302, 304. The peak shear stress is preferably greater than about 4 Pa and more preferably greater than 7 Pa. In an exemplary embodiment, the peak shear stress reaches about 8 Pa or higher. The average shear stress across the entire internal wall form element 302 to element 304 is preferably greater than about 1.5 Pa, and more preferably greater than 2.5 Pa (reaching almost 2.8 Pa in certain embodiments).

In certain embodiments, the distance between the two cylindrical elements is any distance necessary to a variable pressure shape between the two cylindrical elements. In embodiments, the distance may be between 5 and 10 mm if the diameter of the scope channel being cleaned is between 4 mm and 4.5 mm. In other embodiments, the distance may be a ratio relative to the diameter of the scope channel, such as less than 4:1, less than 2:1 or less than 1.5:1 or other ratio (distance: diameter of scope channel).

The diameter of the cylindrical elements may be designed to avoid deflection of proximal and distal end portions 302, 304. Deflection of these cylindrical elements can create a gap due to buckling that results in less than idea cleaning or drying results. This is one of the issues with pull thru cleaners, which are as large as 5.2 mm in diameter, but are applied in channels ranging in size from 2.8 mm to 5.0 mm in diameter and which must buckle to advance through the channel. In embodiments, the diameter of the cylindrical elements are between 1.0 and 1.23 times the diameter of the channel being cleaned or dried to keep the cleaning/drying device 200 centered in the channel being cleaned, with minimal to limited deflection of the ends of the cylindrical elements. Additionally, a deflection equation may be used to obtain the optimal cylindrical elements.

If the cylindrical elements are too high in diameter relative to the channel size, this can result in ineffective cleaning or drying due to gaps in the cylinders, deflection of the cleaning/drying device, too much resistance to pull the cleaning/drying device 200 consistently through the channel, among other issues. The materials selected can also impact this result. In embodiments, the material has a durometer between 35 and 70 shore A, depending on the cylinder size and design, though different durometers and multiple durometers in the same device may be used.

In embodiments, the dimensions of cleaning/drying device 200 may allow for the advancement of the cleaner from the distal end without being caught on the elevator of duodenoscopes or endoscopic ultrasound scopes, which is an issue with current bristle brushes and pull through cleaners, though the dimensions of the cleaning/drying device 200 may also allow for passing through the scope channel in the opposite direction, from proximal to distal.

In embodiments, the cleaning and/or drying device 200 may have one or more absorbent sponges placed in front of or at the end of cleaning and/or drying element 300 or in between one or more of the cylindrical elements to absorb biomatter and debris and fluid. The absorbent sponges may be of a single cell configuration or have multiple sponges with different cell configurations to provide scrubbing, absorption, lifting, diffusion of cleaning fluid, or a combination of these attributes. The absorbent sponges may be of any material, including polyurethane, polyvinyl alcohol, or other absorbent material. In embodiments, the sponges are soft and atraumatic when immersed in fluid, and expand to a size that is at least the size of the channel being cleaned, and in a preferred embodiment is larger than the channel being cleaned. The sponges may be any shape that conforms and aids in cleaning and/or drying the scope's channel, including by way of example, not limitation, cylindrical in shape, spiral in shape, conical, triangular, square or any combination thereof. In an exemplary embodiment, the sponge(s) will have a pore size of between about 200 to 1500 PPC, preferably between about 200 PPC and about 600 PPC.

The design of cleaning device 200 may vary based on the viscosity of the cleaning fluid used to clean the scope channels. In a preferred embodiment, the cleaning fluid has the viscosity of water. The design of cleaning device 200 may also vary based on the target temperature used to submerge the scope for cleaning. In embodiments, the target cleaning temperature is between 25 and 35 degrees Celsius.

In embodiments, cleaning/drying device 200 may include a brush of various designs which contacts a portion of the channel wall in addition to the other aspects of cleaning/drying element 300. The brush may be of a length that is in the ration of 1.0 to 1.4 times the diameter of the channel to be cleaned or dried. In embodiments, the brush is preferably made of an atraumatic polymer, such as polyurethane, with a thickness and durometer designed to limit trauma and injury to the channel wall, while maintaining sufficient rigidity to remove contamination or moisture from the walls of the channel. The diameter of the brush elements contacting the channel wall may be any diameter, but in embodiments may be between 0.5 and 2 mm. The brush elements may be perpendicular to the navigation element and in embodiments, may be part of a separate, shorter navigation element designed to reach only a few a limited distance into the biopsy channel. This shorter version may be any length appropriate for cleaning or drying the initial entry points into the biopsy channel, but in a preferred embodiment is between 4.5 and 15 cm long. This brushing element, whether part of the cleaning element or in a separate shorter version, may also utilize nylon wire bristles or other bristles if arranged in a pattern that is effective in cleaning or drying and minimizes trauma to the scope channel. A grip element of the brush may have a shape at one end or in the center of the element that is larger to facilitate introduction into the biopsy channel.

In certain embodiments, cleaning and/or drying device 300 may contain multiple cylindrical elements with variable pressure elements in between the cylindrical elements, such as, for example, a series of five sets of cylindrical elements with a variable pressure element between each of the cylinders. The variable pressure element may be the same or may vary to create alternating pressure profiles. The multiple cylindrical elements with variable pressure elements between the cylindrical elements may be greater or less than five sets, as appropriate for the given application.

Referring now to FIG. 7B, one embodiment of a cleaning and/or drying device 400 with multiple cleaning and/or drying elements 300 will now be described. As shown, each cleaning and/or drying element 300 includes proximal and distal end portions 302, 304 and a variable pressure region 306 therebetween, as described above. Proximal and distal end portions 302, 304 are preferably cylindrical elements having an outer diameter substantially the same as the inner diameter of the lumen to be cleaned (as discussed in detail below). In this embodiment, the cleaning and/or drying elements are coupled to each other at the proximal and distal end portions. In an exemplary embodiment, the proximal end portion of one cleaning and/or drying element is integral with the distal end portion of the next cleaning and/or drying element, although it will be recognized that other configurations are possible. For example, cleaning and/or drying device 400 may have more than one cylindrical element placed in close proximity to another cylindrical element with a spacing that does not create variable pressure, followed by or, alternatively, before, a cylindrical element with a spacing between the next cylindrical element that creates variable pressure between cleaning and/or drying element 300 and the wall of the channel being cleaned. In embodiments, a series of cylindrical elements may be organized in various spacing to create variable pressure between the cylindrical elements and certain spacing to create constant pressure between the cylindrical elements.

Cylindrical elements 302, 304 may be made of any shape and size that makes contact and conforms at least in part to the walls of the channel being cleaned, including in embodiments, cylindrical elements with a taper, a reverse taper, cylindrical elements that deflect and contact each other or which deflect and do not contact another cylindrical element, or which contact or do not contact a variable pressure shape between the cylindrical elements. The cylindrical elements do not have to be cylindrical, but need to be able to assist with creating a variable pressure result with the rest of the elements of cleaning and/or drying device 400, which means they must have wall contact that is meaningful enough to support creating a variable pressure area to accelerate fluid flow or air flow and thereby direct the cleaning fluid or air at the channel wall with hydrodynamic or air pressure.

Cleaning device 400 may be designed to capture a certain volume of debris relative to the dimensions and level of contamination of the channel being cleaned or a certain level of moisture with drying. For example, additional cylinders and variable pressure elements may be added increasing the length of cleaning device 400 to capture and remove more contamination or moisture. In addition, in embodiments, a sponge or sponges of various pore size, diameter and length may be added to increase the removal of contaminants or moisture.

In embodiments, each cleaning and/or drying element 300 is between 2.5 cm and 7.5 cm long and cleaning and/or drying device 400 contains multiple variable pressure areas separated by multiple cylindrical elements. In a preferred embodiment, cleaning and/or drying device 400 contains five variable pressure areas separated by six cylindrical elements. In certain embodiments, cleaning and/or drying device 400 may include two additional cylindrical elements 402, 404 at a distal end of the device 400.

Referring now to FIG. 7A, another embodiment of a cleaning and/or drying device with multiple cleaning and/or drying elements will now be described. As in the previous embodiment, each cleaning and/or drying element 300 includes proximal and distal end portions and a variable pressure region therebetween, as described above. The proximal and distal end portions are preferably cylindrical elements having an outer diameter substantially the same as the inner diameter of the lumen to be cleaned (as discussed in detail below). In this embodiment, the cleaning and/or drying elements are coupled to each other at the proximal and distal end portions. In an exemplary embodiment, the proximal end portion of one cleaning and/or drying element is integral with the distal end portion of the next cleaning and/or drying element, although it will be recognized that other configurations are possible.

In this embodiment, the cleaning and/or drying device further includes one or more substantially cylindrical cleaning and/or drying members 422 located at or near the proximal end of the cleaning and/or drying device. Cleaning and/or drying members 422 are substantially cylindrical and, therefore, do not include the variable pressure region discussed above.

The cleaning and/or drying device may further include a centering element 424 on either or both of the proximal and distal end portions of the cleaning and/or drying device. Centering element(s) 424 serve to center navigation element 301 and the cleaning and/or drying device as the device is pulled or pushed through lumens around turns and navigates through corners and other complex areas, including junctions of multiple lumens and internal channels in the scope or other instrument being cleaned. Centering element(s) 424, in embodiments, may be smaller than the diameter of the lumen through which the device is being advanced, but have a significant enough size to prevent misalignment and deflection of the navigation element 301 to one side or another of the lumen as it navigates, including as the cleaning and/or drying device as it is pulled or pushed around curves, corners and junctions of various lumens (including Y junctions).

Centering element(s) 424 may be any shape that keeps the device generally centered and prevents this deflection, with a preferred embodiment being a cylindrical shape with a tapered distal end. When this sort of misalignment occurs, which is an issue with existing brushes and pull thru cleaners, the brushes and other elements are pulled to one side of the lumen as the cleaners are pulled around curves, corners and junctions of lumens, with the result being contact with the lumen wall and the cleaning and/or drying element (whether a brush, pull thru or other cleaner) is minimized, adversely changed, or lost, resulting in an adverse impact on the effectiveness of the cleaning and/or drying approach. By placing a centering element at the front or back, or both of the device, this issue is corrected, resulting in more consistent, effective cleaning and/or drying, especially around curves, corners, channel junctions and other complex areas inside an endoscope or other endoscopic instrument or device.

In some embodiments, centering element (424) may comprise a series of shaped elements projecting from the elongate member or the navigation member. This series of shaped elements may, for example, comprise struts, spikes, or other projections extending radially outward from the elongate member and sized to substantially center the elongate member and/or the drying/cleaning elements within the internal channel of the endoscopic device.

In a preferred embodiment, centering element(s) 424 are between 50 percent and 90 percent of the diameter of the lumen being cleaned, with a further preferred embodiment having a diameter or height between 70 percent and 85 percent of the diameter of the lumen being cleaned. Centering element(s) 424 can be any shape that preserves the centering of the cleaning and/or drying element as it is navigated through a channel. In embodiments, this includes cylindrical, conical, spherical and a centering element may be placed at the distal area of the device, at the distal and proximal end, between cleaning and/or drying members, or the proximal end, as appropriate to aid in centering the cleaning and/or drying element, especially as it navigates around curves, across Y-junctions and other aspects of a lumen.

Figure 8:
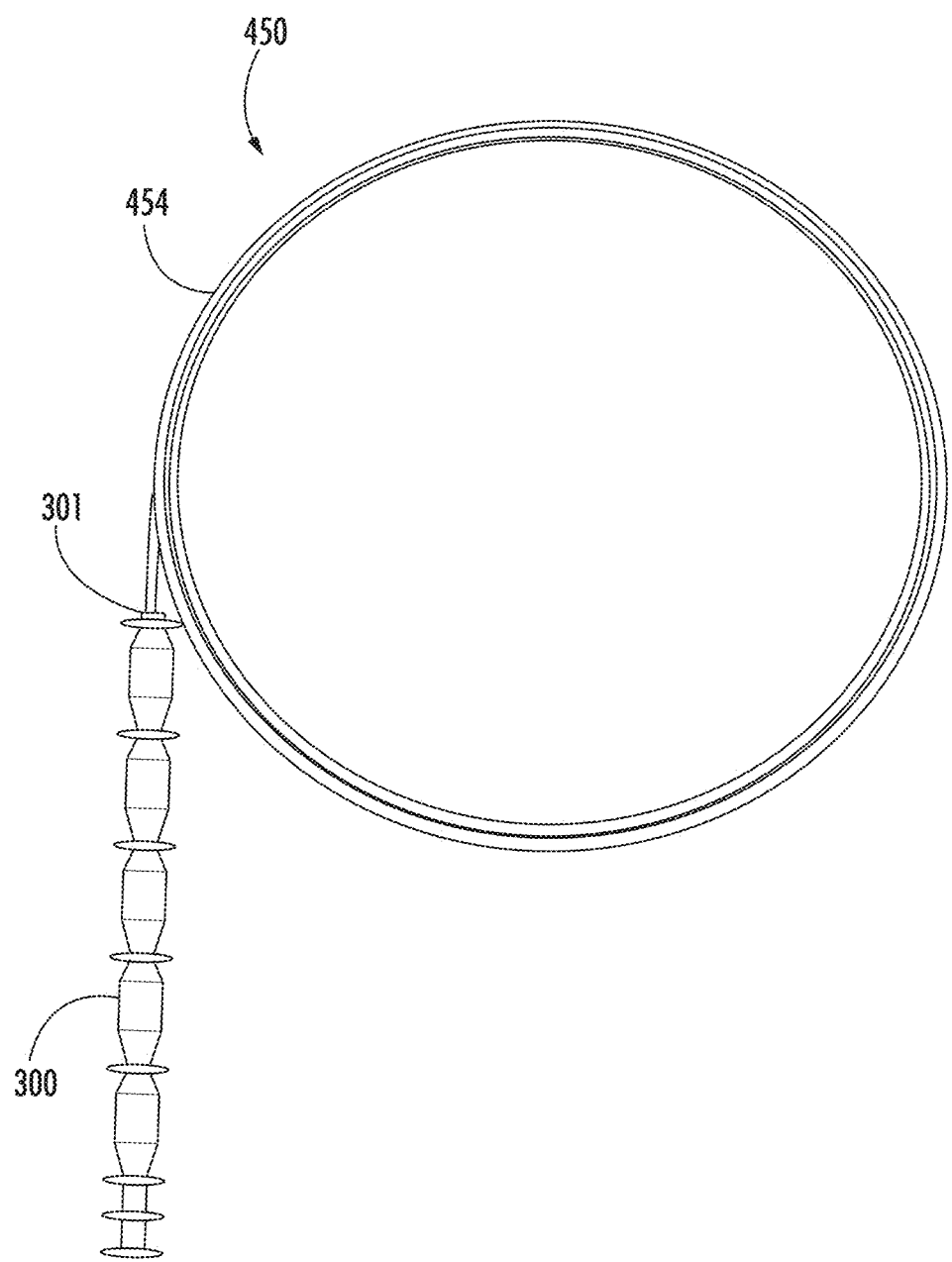
FIG. 8 is a top view of a system for cleaning and/or drying a lumen within an endoscopic device.

FIG. 8 illustrates a system 450 for advancing a cleaning and/or drying device 400 through one or more lumens of an endoscopic device. As described above, cleaning and/or drying device 300 is coupled to a navigation device 301 that may, for example, comprise an elongate wire, tube, filament or similar component, that is flexible but has sufficient rigidness for advancement through a lumen. Navigation device 301 is coupled to a pulling element 454 that may comprise, for example, a flexible silicone or plastic tube that has sufficient length to pass through the entire lumen of, for example, an endoscope or the like.

Figure 9:
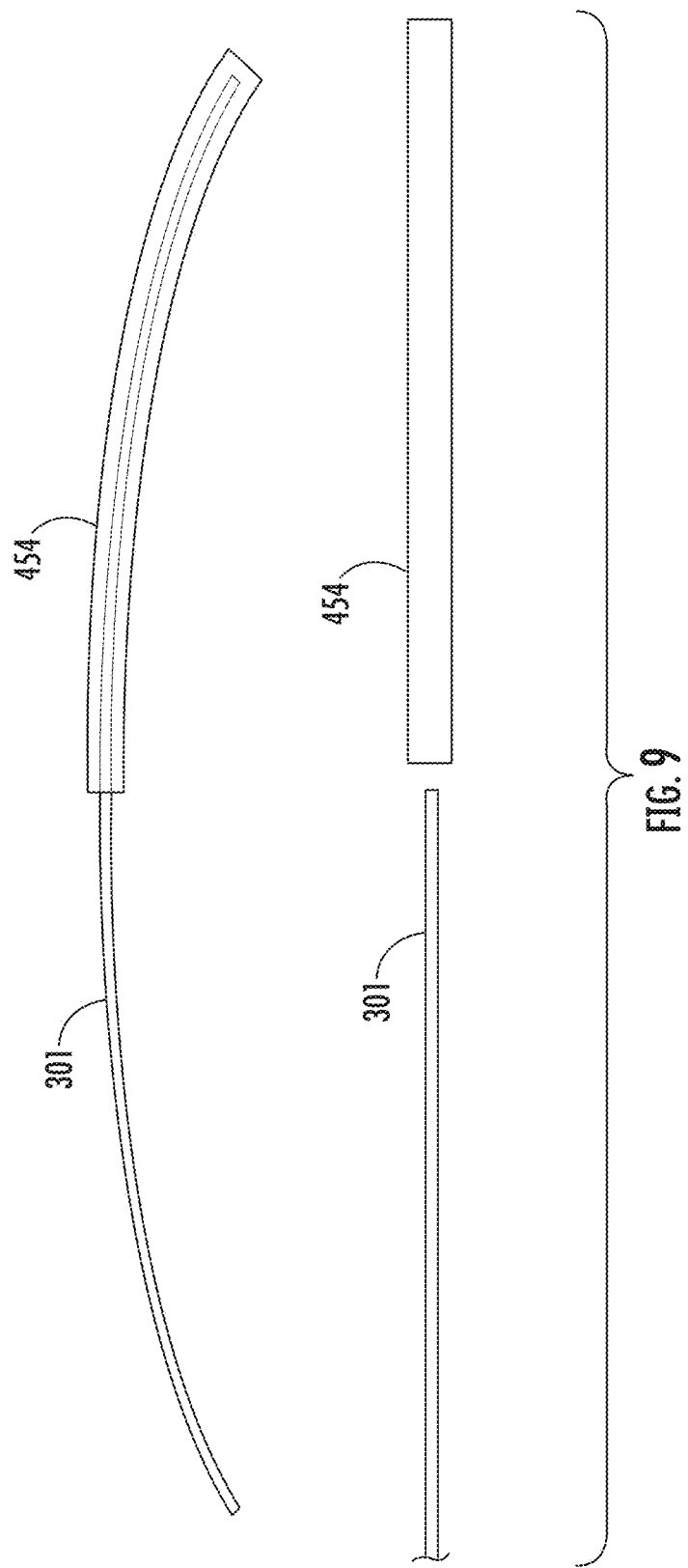
FIG. 9 is a side view of a cleaning and/or drying element and a navigation element.

As shown in FIG. 9, pulling element 454 can be molded to provide a frictional resistance such that navigation device 301 can be advanced into a tube, but friction makes it difficult to withdraw device 301 from pulling element 454. In this manner, as pulling element 454 is withdrawn through the lumen of the endoscope, the cleaning and/or drying element 300 will follow pulling element 301 through the lumen.

Figure 30:
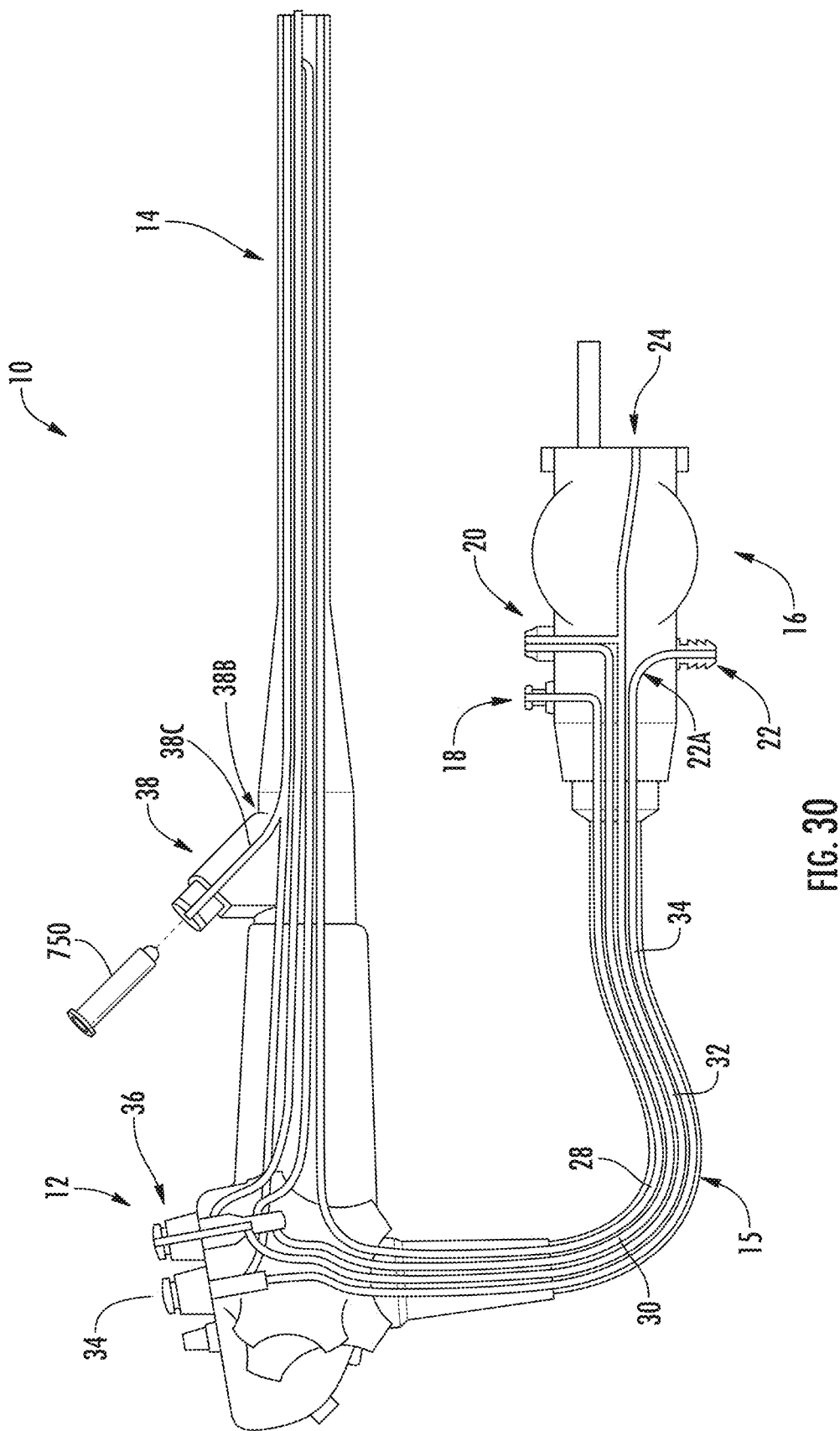
FIG. 30 illustrates a guidance element for use with the cleaning and/or drying devices disclosed herein.
Figure 31:
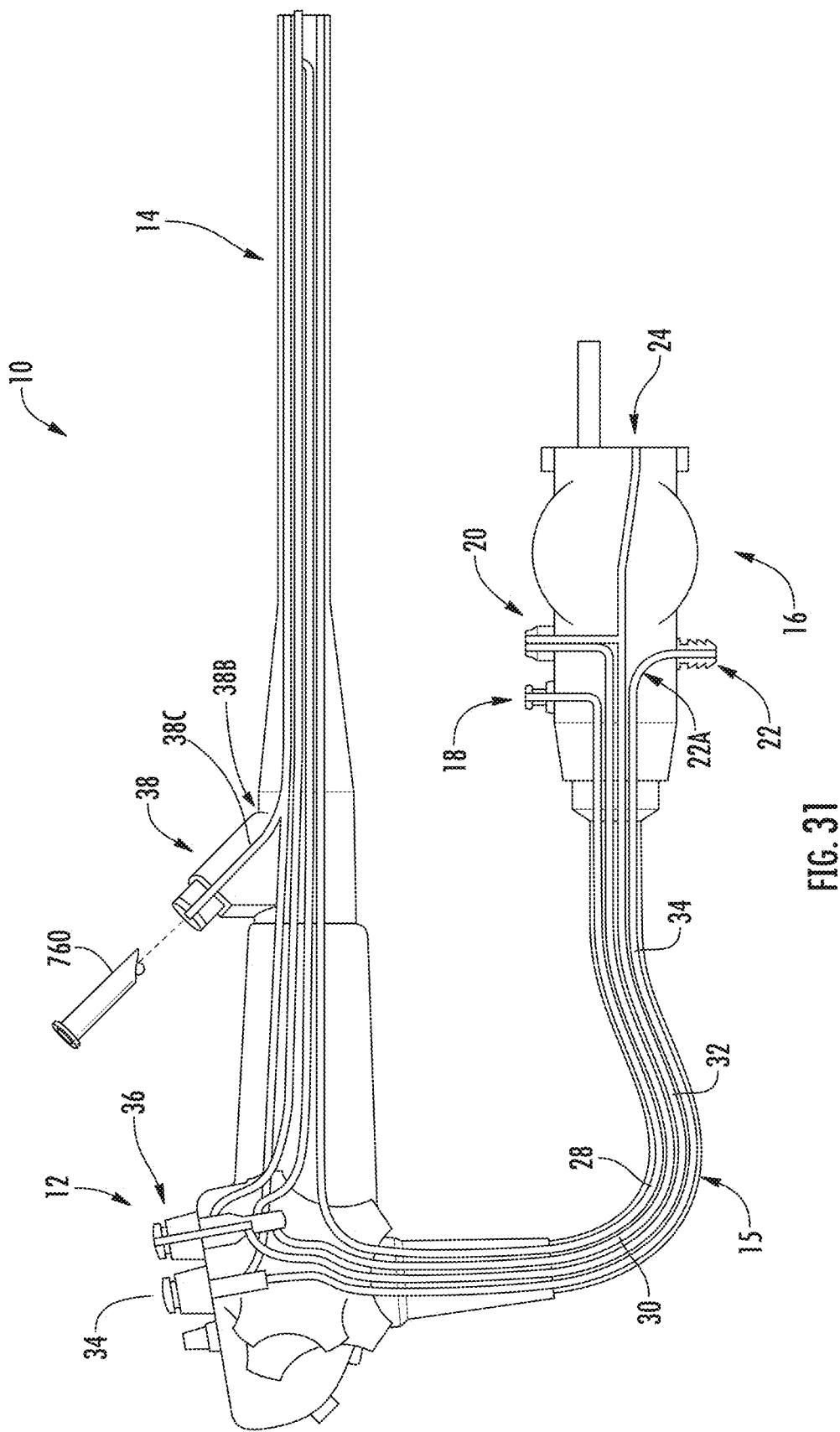
FIG. 31 illustrates another guidance element for use with the cleaning and/or drying devices disclosed herein.

As shown in FIGS. 30 and 31, the system may further include a guidance element (750 in FIGS. 30 and 760 in FIG. 31) to aid in passing the cleaning and/or drying device 200 through certain difficult areas of the endoscope. In particular, the guidance element inhibits the navigation element from deflecting into the wrong channel when passing an internal junction between multiple channels, such as Y junction 38B between suction channel 22 and biopsy channel 38C. Alternatively, the guidance device may be used to navigate the cleaning and/or drying device through tight turns or bends in endoscopic lumens.

In use, the guidance element 750 or 760 may be inserted into one of the scope's internal channels, such as biopsy channel 38C or suction channel 22, in order to aid in passing cleaning and/or drying device 200 from the distal end of scope 10 to the proximal end of biopsy channel 38C or suction channel 22 to facilitate cleaning and/or drying in a manner where the debris is pulled away from the complex, hard-to-clean distal end of the scope in a distal to proximal motion.

Referring now to FIG. 30, guidance element 750 comprises a hollow tube, such as a tubular sheath or the like, that may be temporarily inserted in the desired branch of an internal junction between two channels, such that a portion of cleaning and/or drying device 200 enters into, or engages with, guidance element 750 as it is advanced through the channel and deflects or passes into guidance element 750 to avoid advancing cleaning and/or drying device 200 into an unintended side of a junction or intersection of internal channels. For example, when cleaning and/or drying the biopsy channel portion 38C of the scope 10, if the navigation element of cleaning and/or drying device 200 is advanced from the distal to proximal end of the channel (i.e., from the distal end of shaft 14 to biopsy valve 38), the navigation element will need to pass internal Y junction 38B to advance up the last portion of the biopsy channel 38C. In certain embodiments, guidance element 750 may be inserted from the entry point to the biopsy channel 38C past the Y junction 38B, so that the navigation element of cleaning and/or drying device 200 enters into, or engages with, the guidance element and emits at the end of the biopsy channel 38C, rather than deflecting at Y junction 38B and advancing toward suction portion of the endoscope [see, for example, the suction valve 36 in FIG. 1].

In a similar manner, guidance element 750 can be inserted from the suction valve 36 and advanced just past the internal Y junction 38B so that passage of the navigation element of cleaning and/or drying device 200 from the distal end of the scope to the proximal end of the suction channel occurs without a potential deflection of the navigation element at the internal Y junction 38B.

Guidance element 750 may also be used to assist, if needed, with advancing cleaning and/or drying device 200 around a tight internal turn in the internal channel of the endoscope, such as the exit of the channel 22 in FIG. 1 and for other assistance, if needed, with advancing the navigation or the cleaning and/or drying element.

In certain embodiments, guidance element 750 is tubular or cylindrical with an outer diameter smaller than an inner diameter of the internal lumen (e.g., the biopsy channel 38) and an inner lumen having a diameter that is at least larger than the diameter of the navigation element of cleaning and/or drying device 200. In a preferred embodiment, guidance element 750 is of a shape that conforms as closely as possible to the diameter of the scope channel leading up to internal Y junction 38B or other internal areas of scope 10, with a length that reaches or extends past the junction 38B, which, in embodiments, can be between 8 and 20 cm. As a further preferred embodiment, with a scope with an inner channel with a diameter of 4.2 mm, the outer diameter of the guidance element would be between 3.5 mm and 4.15 mm and the inner diameter would be between 1.5 mm and 4.05 mm.

In embodiments, guidance element 750 may comprise an angled tip to further conform to the shape of a multi-channel internal junction in the scope. In embodiments, the proximal end of guidance element 750 may have a flange that is larger than the entry opening to the specific scope channel where the navigation element is inserted, so that the navigation element cannot be advanced entirely into the channel and result in difficult withdrawal. In an alternative embodiment, guidance element 750 may not have a flange, but may have a marker, including for example, a pad printed or other line, demarcating the maximum recommended point of advancement of the navigation element into the scope channel.

FIG. 31 illustrates another embodiment of a guidance element 760 that comprises a substantially circular rod having an angle distal tip so that the elongate navigation member 301 can be passed from the distal end of the scope to the suction valve opening while deflecting up into the biopsy channel 38C at the Y junction 38B.. In embodiments, the proximal end of guidance element 760 may have a flange that is larger than the entry opening to the specific scope channel where the navigation element is inserted, so that the navigation element cannot be advanced entirely into the channel and result in difficult withdrawal. It may also include an angle cut at its distal end to further conform to the shape of a multi-channel internal junction in the scope.

Figure 10:
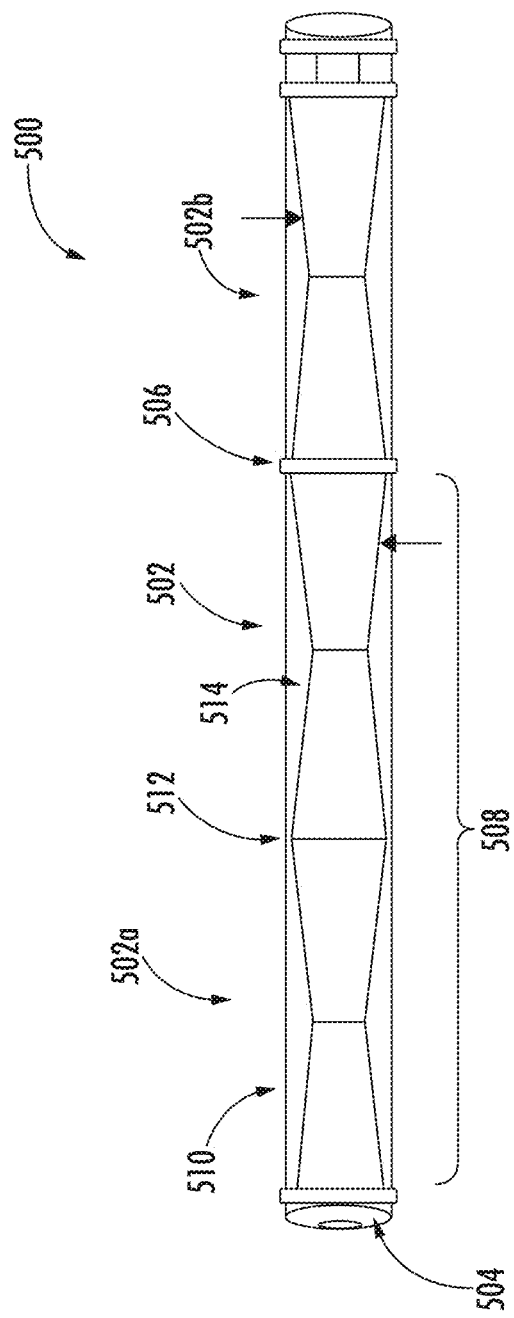
FIG. 10 is a side view of an alternative embodiment of a cleaning and/or drying device.

FIG. 10 illustrates another embodiment of a cleaning and/or drying device 500 with multiple cleaning and/or drying elements 502a, 502b coupled to a navigation element 504. As shown, cleaning and/or drying elements 502a, 502b each include cylindrical wall contact portions 506 and a variable pressure central portion 508. In this embodiment, each central portion 508 of cleaning and/or drying elements 502a, 502b includes at least one contraction portion 510 that angles downwards and then a throat portion 512 that angles upwards again 512 towards the luminal wall. As shown cleaning and/or drying element 502a includes an additional portion 514 that also includes a contraction and throat portion, forming two separate variable pressure elements within a single cleaning and/or drying element 502a. Cleaning and/or drying element 502b only includes one variable pressure region, although it will be understood that various combinations of these features may be included. For example, cleaning and/or drying device 500 may include multiple cleaning and/or drying elements that each include multiple variable pressure regions. Alternatively, each of the cleaning and/or drying elements may only include one variable pressure region as shown with respect to cleaning and/or drying element 502b. As in previous embodiments, the combination of these sections creates variable pressure that induces high shear stress against the walls on the lumen.

FIGS. 11A-11D illustrates other configurations for the variable pressure region of the cleaning and/or drying element. In FIG. 11A, a cleaning and/or drying element 560 comprises a contraction section 562 with a larger angle between section 562 and the throat 566 than the angle between throat section 566 and diffusion section 564. FIG. 11B illustrates a cleaning and/or drying element 570 that does not include a specific throat section. As shown, a cleaning and/or drying element 570 includes a contraction section 572 that immediately forms into the diffusion section 574 (i.e., angles towards the inner lumen and then angles back inwardly without a central cylindrical throat section).

FIGS. 11C and 11D illustrate cleaning and/or drying elements 550 that create multiple high-pressure regions by comprising more than one throat section 552. In addition, the series of cleaning and/or drying elements may each have different configurations. As shown, in some instances, a cleaning and/or drying element with a single throat section can be followed by one with multiple throat sections or vice versa.

Figure 12:
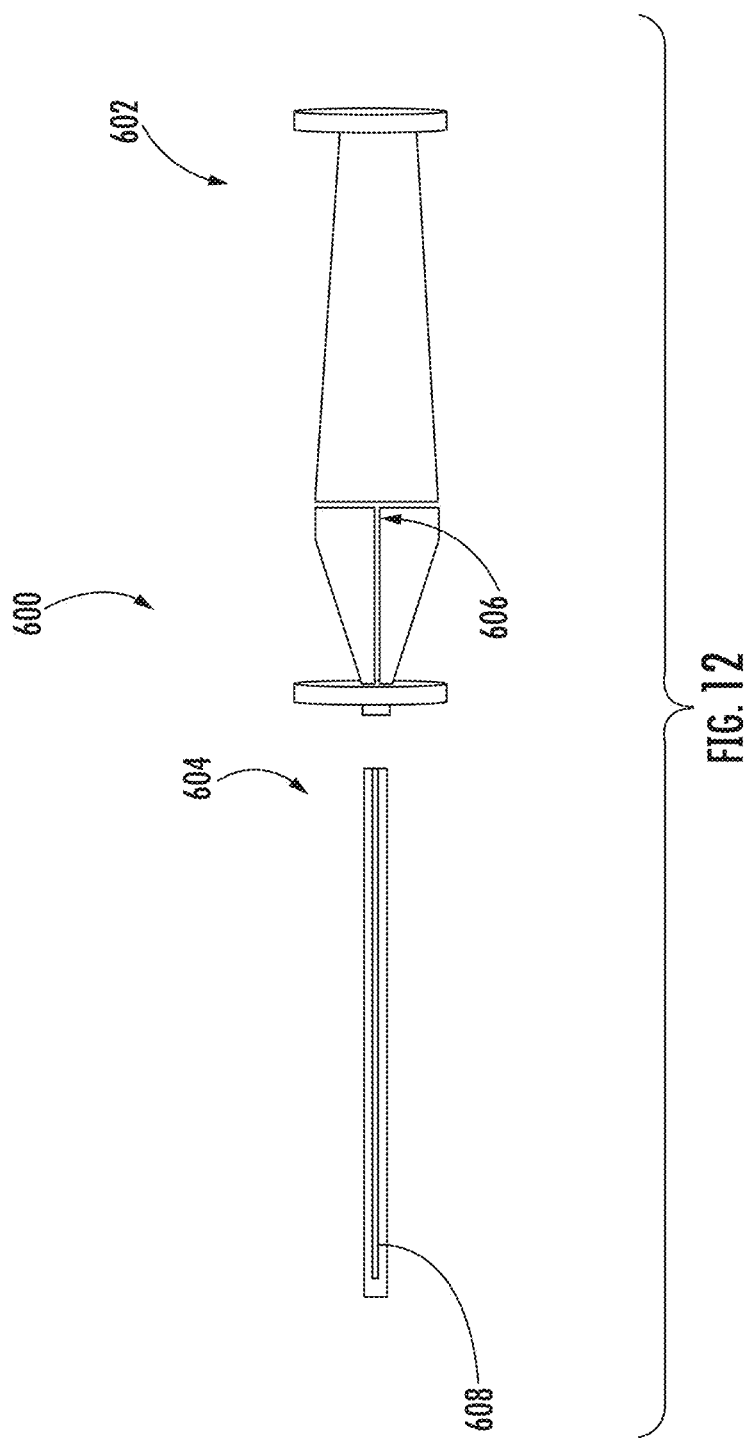
FIG. 12 is a side view of another embodiment of a cleaning and/or drying device incorporating a cleaning and/or drying element and a navigation element.

FIG. 12 illustrates yet another embodiment of a cleaning and/or drying device 600 that includes a cleaning and/or drying element 602 and a navigation element 604. In this embodiment, navigation element 604 includes an infusion lumen 608 for delivering air or additional fluid to cleaning and/or drying element 602. Cleaning and/or drying element 602 includes one or more infusion ports 606 for delivering the air and/or fluid into the variable pressure region within the lumen created by cleaning and/or drying element 602. Delivering fluid into the variable pressure region increases the pressure therein, which thereby increases the fluid or air forces against the internal wall of the lumen to be cleaned.

Cleaning and/or drying device 400 may be non-sterile, disinfected or sterilized using an appropriate sterilization method, including e-beam, gamma, eto gas, hydrogen peroxide, steam or the like. In the event that the device 400 is used for drying, it will typically be sterilized.

The materials for navigation element 301 can be any material sufficient to navigate through the channel being cleaned and able to manage the pull force associated with advancing the cleaning and/or drying element 300 through the channel being cleaned. This includes all metal and polymer-based materials, including stainless steel wires, nitinol, and other metals. It also includes all polymer-based materials, whether in a monofilament form, extruded tube, braided or any other form sufficient to facilitate advancing the cleaning and/or drying element 300 though the channel being cleaned. In a preferred embodiment, navigation element 301 is a monofilament composed of nylon, polyamide, polyurethane, PET or other polymeric material, with a diameter of at least 1 mm. Navigation element 301 may include a grip element at one end that facilitates holding and passing navigation element 301. In embodiments, this grip element is larger than the entry point to the biopsy channel to protect against over advancing navigation element 301 into the biopsy channel and losing one's grip on navigation element 301.

In an alternative embodiment, navigation element 301 comprises one or more internal channels that allow for cleaning fluid or air to be infused down navigation element 301 to one or more ports and also allow for suctioning fluid if desired. An infusion port may be present in cleaning/drying device 300 to emit the fluid or air advanced through navigation element 301, allowing cleaning fluid or air to be infused through navigation element 302 into cleaning device 200 to further modify and increase the hydrodynamic pressure of the cleaning fluid against the channel wall. In embodiments, navigation element 301 and cleaning element 302 may also contain one or more suction channels which may be used to more rapidly circulate the cleaning fluid or air, and/or to flush the fluid and extract debris and fluid or moisture through the suction channel.

In certain embodiments, navigation element 301 is attachable to the cleaning and/or drying element 300 through permanent attachment, which can be through molding, overmolding, two shot molding, glue or other means to create an attachment between the navigation and cleaning and/or drying elements where the two elements are fixed or affixed for use. In a preferred embodiment, navigation element 301 is separately attachable and in certain embodiments attachable and detachable, so that navigation element 301 may be attached from one end of a channel the other end, exit the channel and then be attached to cleaning and/or drying element 300. The means of attachment is any way suitable for the intended use, which by way of example may include interlocking elements, compression fitting, a slide and locking mechanism, a loop and a hook mechanism, an insert and twist mechanism or variations and alternative combinations suitable for the diameter and shape of the navigation and cleaning and/or drying elements.

Figure 13:
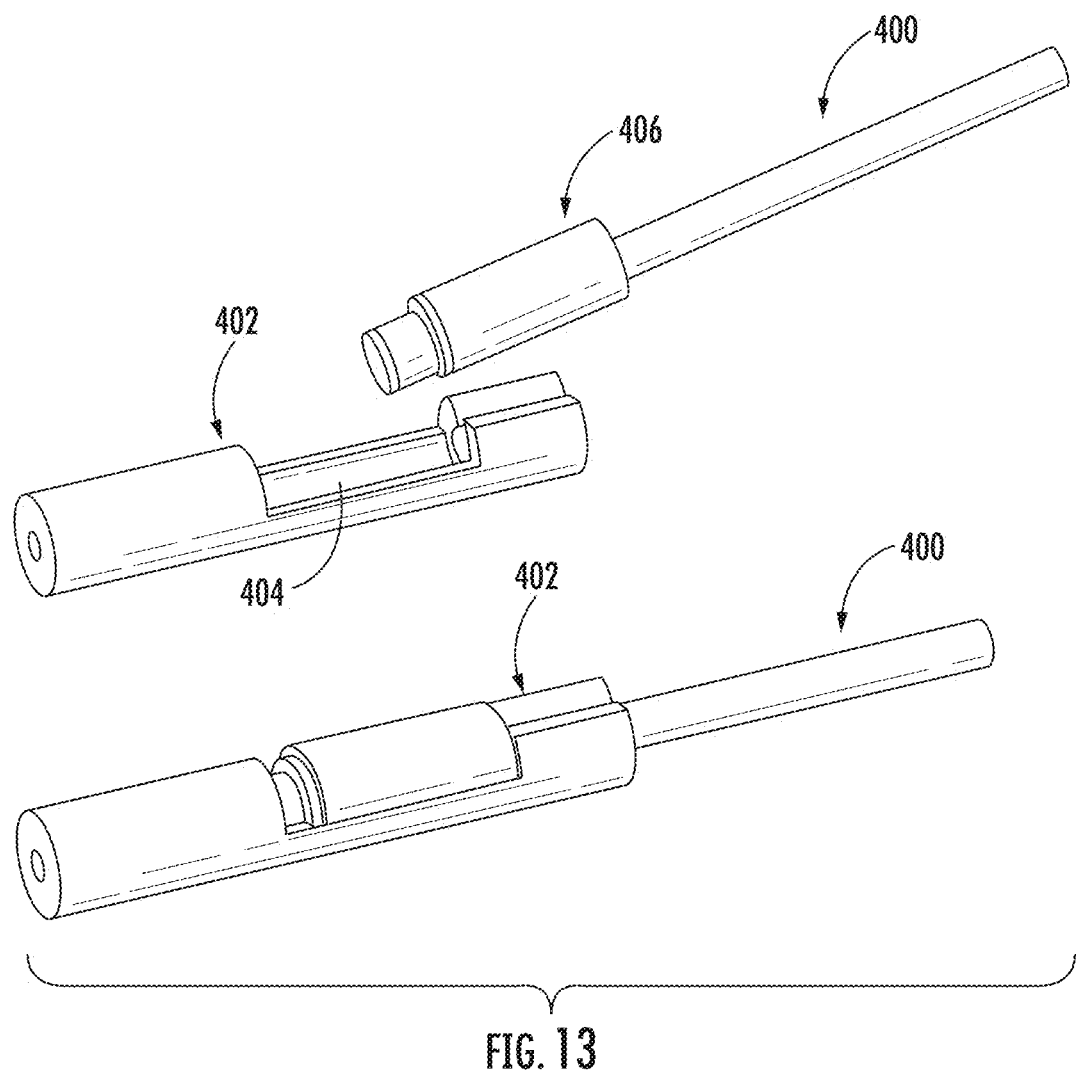
FIG. 13 is a side view of a cleaning and/or drying element and a navigation device, illustrating a method for removably coupling the devices together.
Figure 14:
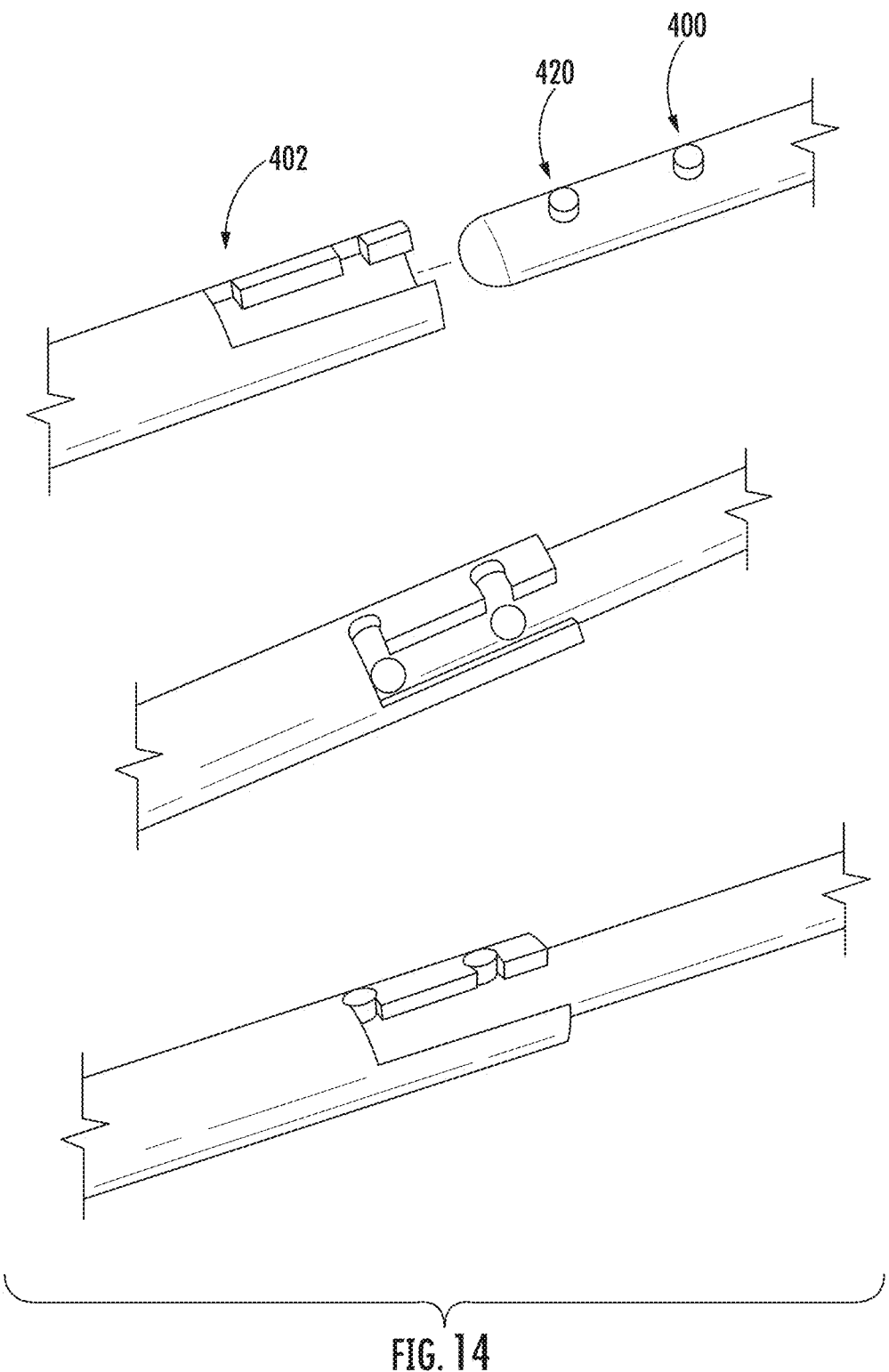
FIG. 14 illustrates another method for removably coupling a cleaning and/or drying device to a navigation device.
Figure 15:
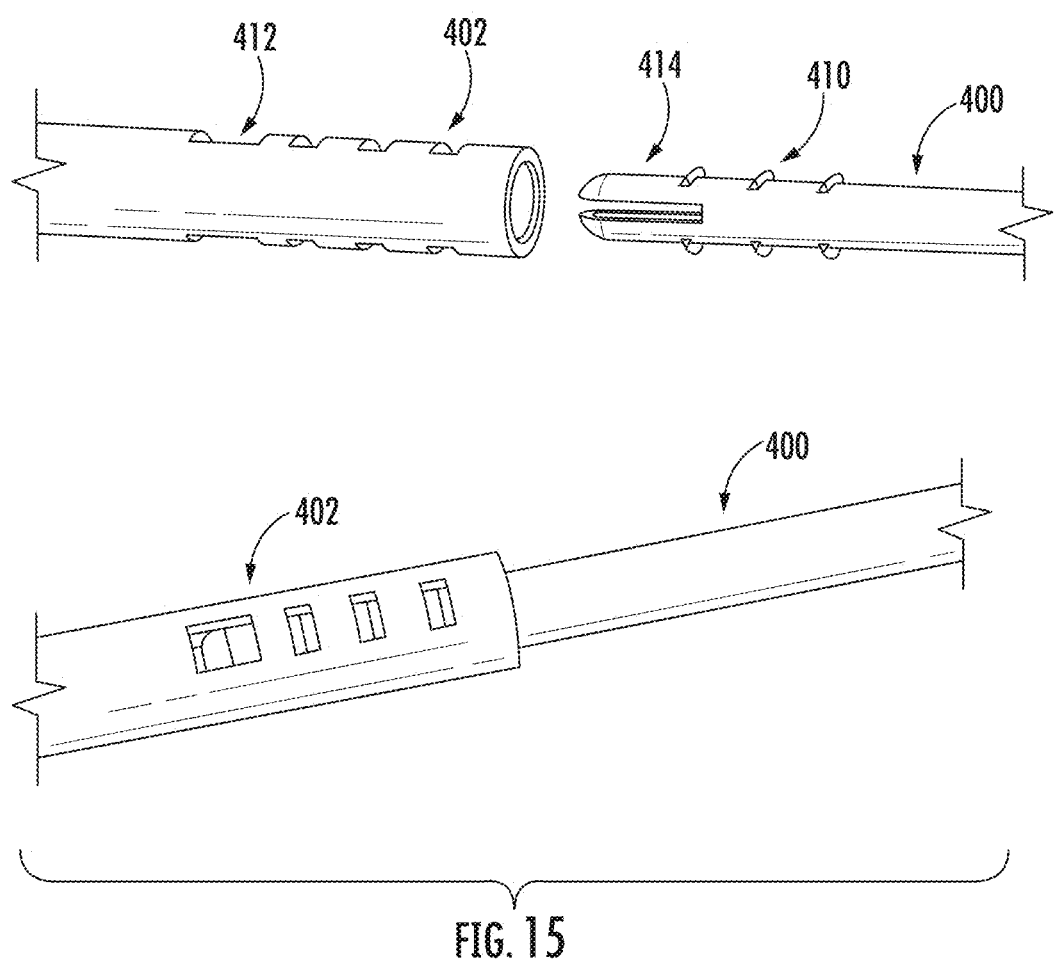
FIG. 15 illustrates yet another method for removably coupling a cleaning and/or drying device to a navigation device.

FIGS. 13-15 illustrate three different embodiments for removably attaching a shaft 400, such as a navigation element to a cleaning and/or drying element 402. As shown in FIG. 13, cleaning and/or drying element 402 may include a recess 404 for receiving a protruding section 406 of shaft 400. As shown in FIG. 15, shaft 400 may include one or more barbs 410 that fit within openings 412 of cleaning and/or drying element 402. Shaft 400 may include a flexible section 414 to allow barbs to 410 to fit within an internal lumen of cleaning and/or drying member 402. As shown in FIG. 14, shaft 400 may include one or more projections 420 that can be rotated into grooves on cleaning and/or drying member 402 to attach the cleaning and/or drying member to the shaft. One skilled in the art will appreciate that the devices and methods discloses herein are not limited to these embodiments. For example, other methods for coupling shaft 400 to cleaning and/or drying element 402 include, but are not limited to flattened monofilaments, wires, strings or filaments coupled to releasable or non-releasable knots, crimps, press-fit elements, projections engaging with holes, channels or other openings, heat staking, heat bending, heat piercing, hooks, snap-fit elements and the like.

In a method according to certain embodiments, navigation element 301 is advanced through a lumen of an endoscopic instrument, such as a biopsy channel 50 of an endoscope 10. The lumen is filled, or partially filled, with a fluid, such as an enzymatic detergent, or other cleaning fluid. The fluid functions to initially clean and/or disinfect the lumen to remove at least some of the biomatter and other pathogens from the lumen. Once the distal end portion of navigation element 302 has passed through the distal opening of the lumen, cleaning element 300 is removably attached to navigation element 301 through one of the devices and methods described above.

After attaching cleaning and/or drying element 300 to navigation element 301, navigation element 301 is withdrawn back through the lumen of the instrument. In certain embodiments, device 200 includes a pull cable configured to withdraw or advance elongate shaft 301 within an internal lumen in endoscope 10. Device may also include an energy source and a motor for advancing and/or withdrawing navigation element 301. Of course, it will be recognized that navigation element 301 may be manually translated through internal lumen via a proximal handle or suitable actuator (i.e., no motor).

As navigation element 301 is withdrawn through the lumen, each cleaning and/or drying element 300 creates its own variable pressure region between proximal and distal ends 302, 304. Specifically, variable pressure regions 306 increase the relative velocity between the fluid within each cleaning and/or drying element 300 and the walls of cleaning and/or drying element 300, which causes the fluid to accelerate relative to the internal walls of the lumen, thereby creating more fluid force against the walls (as discussed in more detail above). This increased fluid force provides a more effective cleaning and/or drying than conventional devices.

Navigation element 301 may be withdrawn through lumen either manually or via a motor, as described above. Preferably, navigation element 301 is withdrawn at a predetermined speed, such as about 20-50 cm/sec, preferably about 30 cm/sec. Applicant has discovered that withdrawal at this velocity optimizes the effects of pressure variable regions 306 on the fluid within cleaning and/or drying elements 300.

Navigation element 301 may be withdrawn only once, or it may be advanced again, and withdrawn a second or third time, depending on the particular cleaning and/or drying requirements. In certain embodiments, 301 is only withdrawn partially through the lumen before it is advanced again so that the cleaning and/or drying elements do not push biomatter and other debris from the proximal portion of the scope (i.e., biopsy channel) back into the lumen.

A kit is also provided for use in cleaning and/or drying an endoscopic instrument. The kit includes any of the cleaning and/or drying devices described above and may include an endoscope instrument or an endoscope, such as any of the endoscopes described above in reference to FIG. 1, or others known by those skilled in the art. In addition, or alternatively, the kit may include a variety of other devices used for cleaning and/or drying procedures in any combination, such as cleaning brushes, swabs and/or sponges, enzymatic cleaners, disinfectants, and other devices and agents for sterilizing and/or disinfecting medical devices, scope drying agents, test strips or other sensors for determining the effectiveness of such cleaning and/or drying devices (i.e., detecting the presence of proteins, biomatter, bacteria, fungi, viruses, protein, ATP or bacteria markers, or other pathogens), personal protective equipment (PPE), scope housings for transporting scopes to and from, for example a reprocessing location, contamination bags and the like.

Another kit provided herein includes a cleaning device and a drying device. In certain embodiments, both the cleaning and drying devices may comprise one or more of the embodiments described above. The kit may include a non-sterilized cleaning device and a sterilized drying device. Alternatively, the kit may include one device that functions to both clean and dry an internal lumen of an endoscopic device. In embodiments, a cleaning device may be one color and a drying device may be a different color in order for users to easily determine the purpose of each device. This aids in identifying the use of each device and it aids in making clear which device is sterilized after it is opened. The color difference may be the navigation element, the cleaning/drying element, a pad print line, or other marker to make clear the different uses of each device.

In certain embodiments, the kit includes a cleaning device such as one the embodiments described above and a drying device that comprises an advancement element that may be a filament, wire, tube or other element capable of advancement into an internal channel, including a long, curved, or other channel that is difficult to access because it is recessed or internal. In embodiments, this element can be grasped at an end once it is pulled through the internal channel and then pulled through the channel as part of the drying process. It also can be advanced from the other end through pushing the advancement element. This element may include a version that is able to advance air through the device and into the channel, including to a removed location well inside the channel and beyond the typical effectiveness of forced air drying in a channel.

The drying member may comprise one or more substantially cylindrical members spaced from each other along the advancement member. The cylindrical members are configured to maintain contact with the channel wall to displace and remove any moisture as the advancement element travels through the channel. The advancement element may be advanced through being pushed, pulled or by other means, including back and forth agitation, advancement and withdrawal based on a pattern. The advancement element may travel through the scope by connection to an automated or mechanized approach or any other means of moving the channel drying element through the channel to displace, absorb and or remove water at least in part through direct contact with the surface area to be dried.

In embodiments, the drying member may comprise a series of one or more cylindrical squeegees that are designed to make wall contact with the internal walls of the channel to remove fluid and moisture from the channel. These cylindrical squeegees may be arranged in any manner that is effective at removing fluid and moisture from the channel. This includes in groups of two and then three squeegees, or vice versa, or in other configurations of squeegees, such as groups of one and then two squeegees, two and then four, three and three, four in a row, five in a row or any other number and configuration of squeegees that is effective for the removal of water and moisture, depending on the channel diameter, length, curves, junctures with other channels and other factors.

In embodiments, certain of these squeegees may be of different heights in order to make the device more adaptable to use in channels of different sizes. For example, the device may have a squeegee that is 5 to 5.2 mm in diameter followed by a smaller squeegee that is between 2 to 2.2 mm in diameter, followed by another squeegee that is 3.8 to 4 mm in diameter to create variable wall contact across a variety of channel sizes. In embodiments, the height and arrangement of squeegees is not limited to this description and these diameters, placements, squeegee thickness and other shall vary based on what is most effective for the drying for a given channel drying application.

The spacing between squeegees and any other elements, including drying elements, may be any spacing that supports rapid and predictable channel drying, including a spacing of 1 mm, 1.25 mm, 1.5 mm, 2 mm, close spacing of 1.25 mm and then a 4 mm gap and then spacing of 1.25 to 1.5 mm or other spacing closer or farther or more variable that optimizes and supports rapid and predictable channel drying. Spacing, diameters and alignment and grouping of drying elements may vary based on channel size, channel material, the number of curves to navigate around, the number of junctions with other channels, if any, the channel dryer material, and other factors specific to the given channel drying application, in embodiments.

The thickness of squeegees, discs and fins are any thickness that aids in channel drying and the positioning of the fins and squeegees to dry and, in embodiments, clean. In embodiments, this includes squeegee and fin thickness of between 0.2 and 0.5 mm, other variants with a thickness of 0.5 to 1.0 mm; other variances with tapered thickness with the thickness greater at the base of the squeegee or fin and tapering closer to the channel wall to enhance deflection and conformance of the element to the channel wall, while providing support and a certain rigidity and flexibility around the advancing element.

In embodiments, the innovation includes a centering element, so that the drying element remains centered as it is advanced through the channel to dry. This element prevents a squeegee or cleaning element from losing contact with the wall of the channel being cleaned, enhancing drying action. The centering element is any shape that keeps the drying element in the relative center of the channel, so that any lateral movement needed to navigate through the channel, especially around curves, does not cause the drying element to flatten against a wall and thereby lose contact with the channel wall it is drying as it is advanced. In an exemplary embodiment, the cleaning element is between 50% and 95% of the diameter of the channel being dried or cleaned. The centering element may be placed anywhere on the advancing element or the drying element, including multiple centering elements to enhance and preserve drying and cleaning performance.

EXAMPLE 1

Applicant conducted a number of tests comparing various characteristics of the cleaning devices disclosed herein (labeled Venturi™ Cleaner in FIGS. 16-18) with a commercial cleaning brush, the Pull Thru™ Cleaner manufactured for Cantel Medical. The Pull Thru™ Cleaner is designed with five cylindrical fins, which are arranged in very close proximity to each other with two of the fins clustered together, followed by a larger space and then three additional fins clustered together. The fins are a flexible polymer overmolded on to a rod of stiffer material that is used to advance the cleaner down the scope biopsy channel from the proximal end of the scope to the distal end, while the scope is submerged in cleaning fluid. The space between each cluster of fins is uniform and the polymer between the fins is a thin, uniform thickness that is overmolded to adhere to the cylindrical monofilament.

Figure 16:
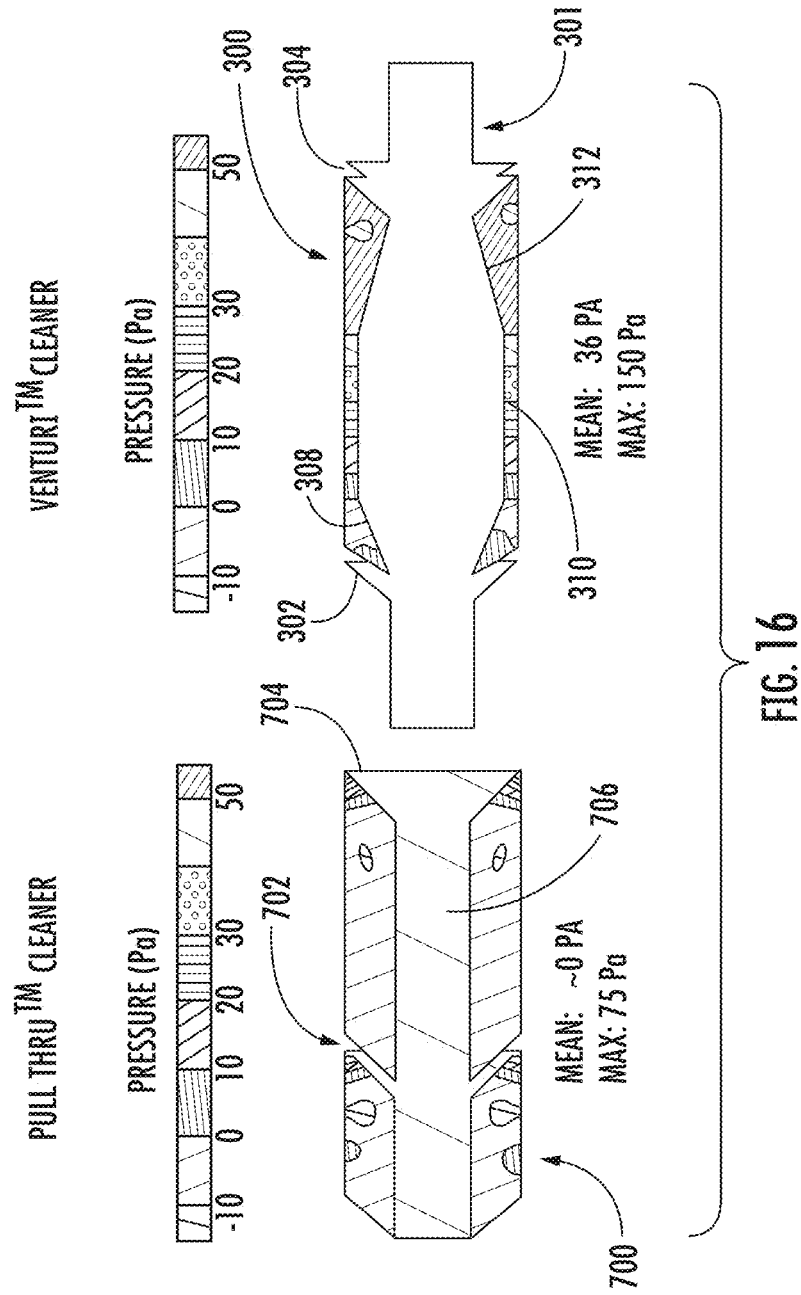
FIG. 16 illustrates test data from a comparison of pressures created by the cleaning and/or drying element disclosed herein and a prior art device.
Figure 17:
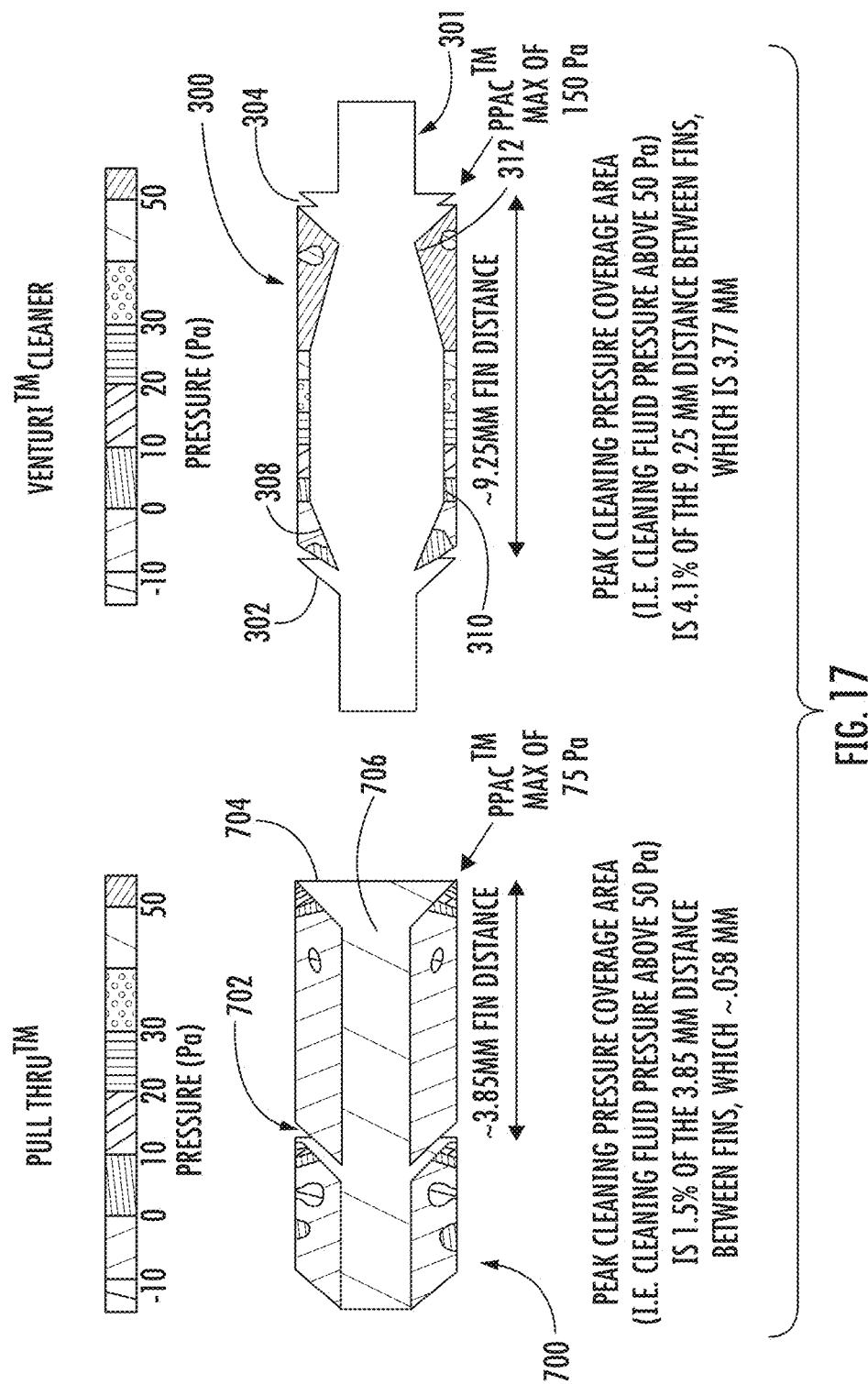
FIG. 17 illustrates the peak pressure cleaning and/or drying area created by the devices of FIG. 16.
Figure 18:
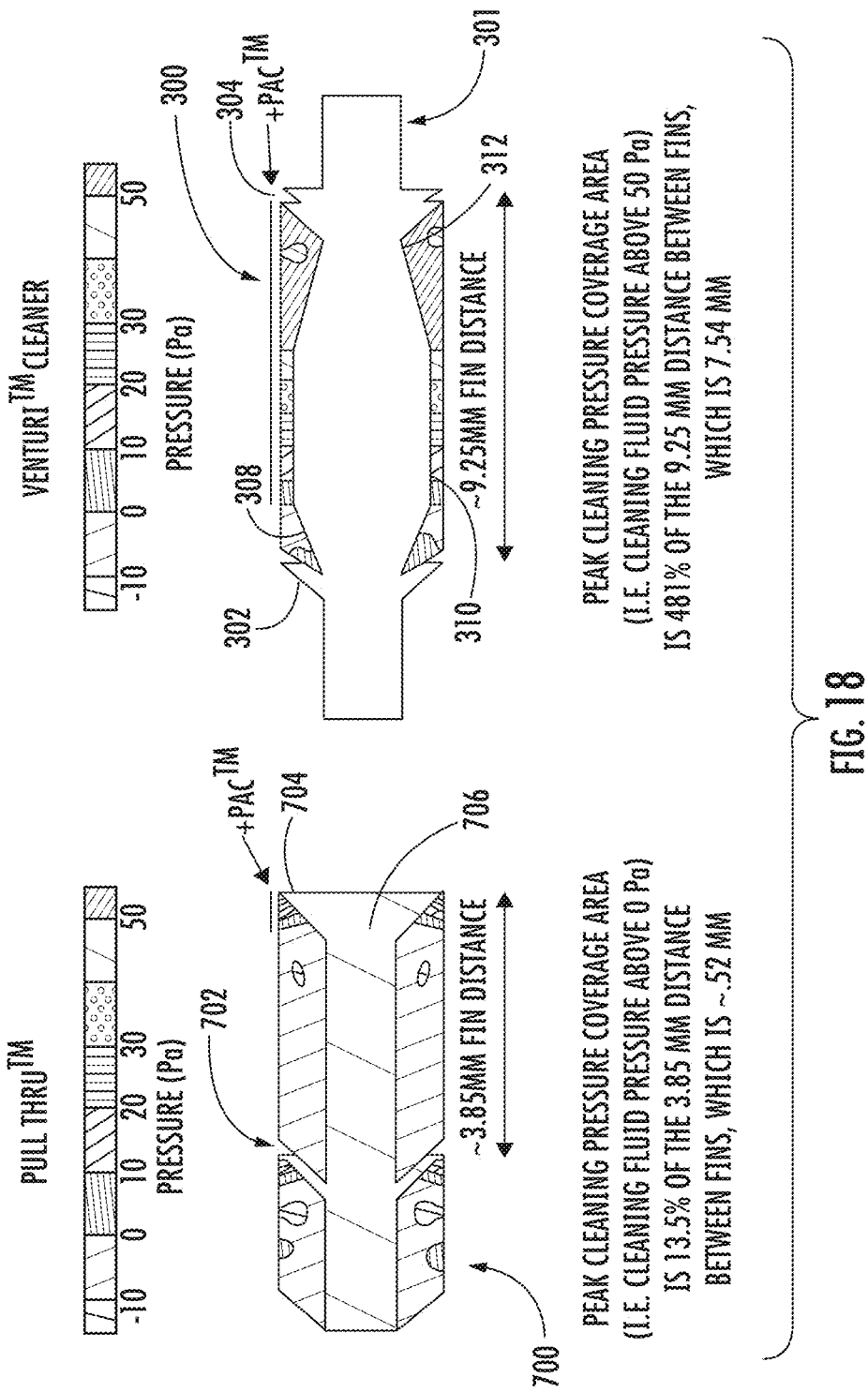
FIG. 18 illustrates the positive pressure cleaning and/or drying areas created by the devices of FIG. 16.

FIGS. 16-18 illustrate the results of these tests. In both cases, a fluid was introduced into a representative lumen of an endoscopic device and cleaning device 200 and the Pull Thru™ Cleaner were advanced through the lumen at a comparative velocities (i.e., about 30 cm/sec). Computational pressure flow modeling was conducted to measure the positive pressure cleaning areas of both devices.

As shown in FIG. 16, the Pull Thru™ Cleaner 700 generated a mean pressure of approximately zero (0) Pa between the proximal and distal ends 702, 704 of each cleaning element 706. The cleaning device 200 disclosed herein (the Venturi™ Cleaner) generated a mean pressure of approximately 36 Pa across the length of each cleaning element 300 between cylindrical elements 302, 304. Thus, the cleaning/drying device 200 disclosed herein produced significantly greater mean pressure against the internal wall of the lumen than the Pull Thru™ Cleaner 700. In addition, the cleaning device 200 disclosed herein had peak pressures over 50 Pa over a significant portion of cleaning element 300 (across the entire throat region 312) with a maximum pressure of 150 Pa. By contrast, the Pull Thru™ Cleaner 700 had peak pressures over 50 Pa in a very small portion of the cleaning element 706 adjacent end 704 and a maximum pressure of only 75 Pa. Thus, the cleaning/drying device 200 disclosed herein produced peak pressures that were dramatically higher and extended over a longer length of the device than the Pull Thru™ Cleaner 700.

Referring now to FIG. 17, the Pull Thru™ Cleaner 700 has a length of about 3.85 mm between proximal and distal ends 702, 704, whereas cleaning/drying device 200 disclosed herein has an average distance of about 9.25 mm between cylindrical elements 302, 304. The Peak Cleaning Pressure Coverage Area ("PPAC™") was considered to be the distance in which a cleaning fluid or air pressure above 50 Pa was present within each cleaning element. The Pull Thru™ Cleaner 700 had a Peak Cleaning Area of about 0.58 mm or 1.5% of the total distance between ends 702, 704. By contrast, the cleaning/drying device 200 disclosed herein had a Peak Cleaning Area of about 3.77 mm or 41% of the total distance between cylindrical elements 302, 304.

Referring now to FIG. 18, the Positive Pressure Cleaning Area ("+PAC™") is defined as the distance along a cleaning/drying element wherein the cleaning fluid or air pressure against the internal wall of the lumen is positive or above zero. As shown, the Pull Thru™ Cleaner 700 had a +PAC of about 0.52 mm or 13.5% of the total distance between ends 702, 704. The cleaning device 200 disclosed herein had a +PAC of about 7.54 mm or about 81% of the length between cylindrical elements 302, 304. Thus, the vast majority of the area between cleaning/drying device 200 and the internal luminal wall had a positive cleaning pressure.

EXAMPLE 2

Applicant also conducted a number of tests comparing the cleaning performance of the cleaning/drying devices disclosed herein (labeled Venturi™ Endoscope Scope Cleaner in FIGS. 25-29) with a commercial cleaning brush, the Pull Thru™ Cleaner manufactured for Cantel Medical. The test objectives were to compare the cleaning performance of several different endoscope channel cleaners in a test circumstance the follows the FDA guidance to test endoscope channel cleaning under worst-case, but clinically relevant conditions.

Fresh egg whites where combined with fluorescent dye and mixed to create a test soil. Egg white's viscosity is equivalent to the internal duodenum contamination in a patient with various forms of disease in which bile and mucous have a higher viscosity than a normal, healthy patient. A 45 cm scope biopsy channel with internal scratches made by an 0.035 hypo tube to simulate instrument passage wear and tear was used for the test. Test soil in the amount of 4 mLs was infused into the test scope biopsy channel, then ends were plugged to prevent escape. The channel was rotated and rocked back and forth to distribute the test soil evenly and then the contaminated test channel was allowed to dry for 3 and a half hours for a worst case scenario. Scope company guidelines require cleaning of a contaminated channel within 1 hour of use.

After 3 and a half hours, the ends of the test channel were unplugged, the test channel was submerged in water for 10 seconds and then a Test Device channel cleaner was advanced through the test channel After one pass of the Test Device channel cleaner, the test channel was inspected under black light for any residual egg white protein and dye remaining in the channel. After each test, the Test Channel was flushed, cleaned and inspected under black light to confirm it was clean before the next test.

Figure 25:
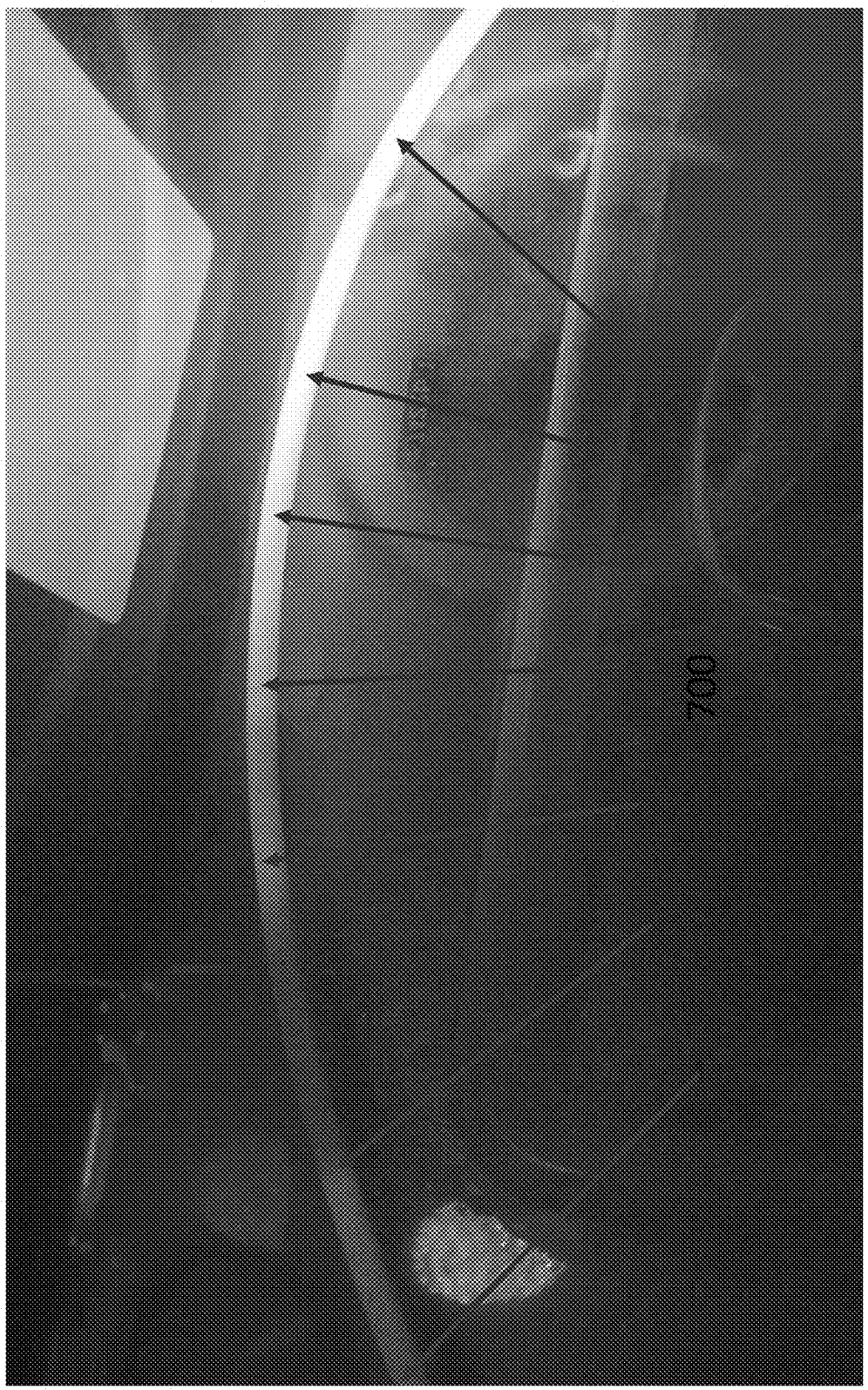
FIG. 25 is a photograph of a black light inspection of a contaminated endoscope channel.
Figure 26:
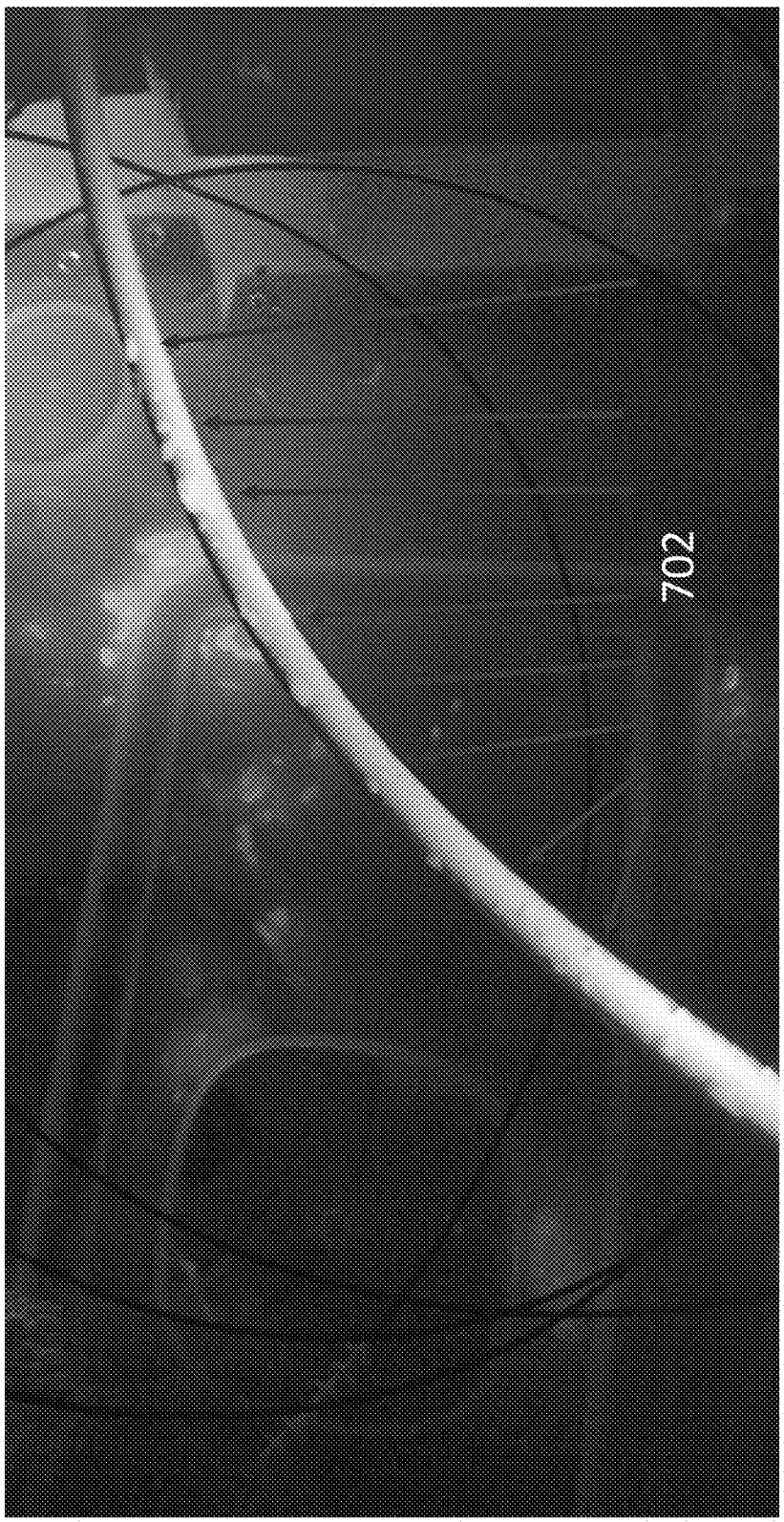
FIGS. 26 and 27 are photographs of a black light inspection of the endoscope channel of FIG. 25 after cleaning with a prior art device.
Figure 27:

FIG. 25 illustrates a photograph of a black light inspection of a contaminated endoscope test channel 700. Egg White and Fluorescent Dye were dried for 3 hours and 30 minutes in the channel. FIGS. 26 and 27 illustrate a photograph of a black light inspection of the endoscope channel 700 after a single pass of the Pull Thru™ Cleaner (labeled 700 in FIGS. 16-18). The residual contamination can be seen throughout the channel (labeled 702 in FIGS. 26 and 704 in FIG. 27).

Figure 28:
FIG. 28 is a photograph of a black light inspection of a contaminated endoscope channel.
Figure 29:
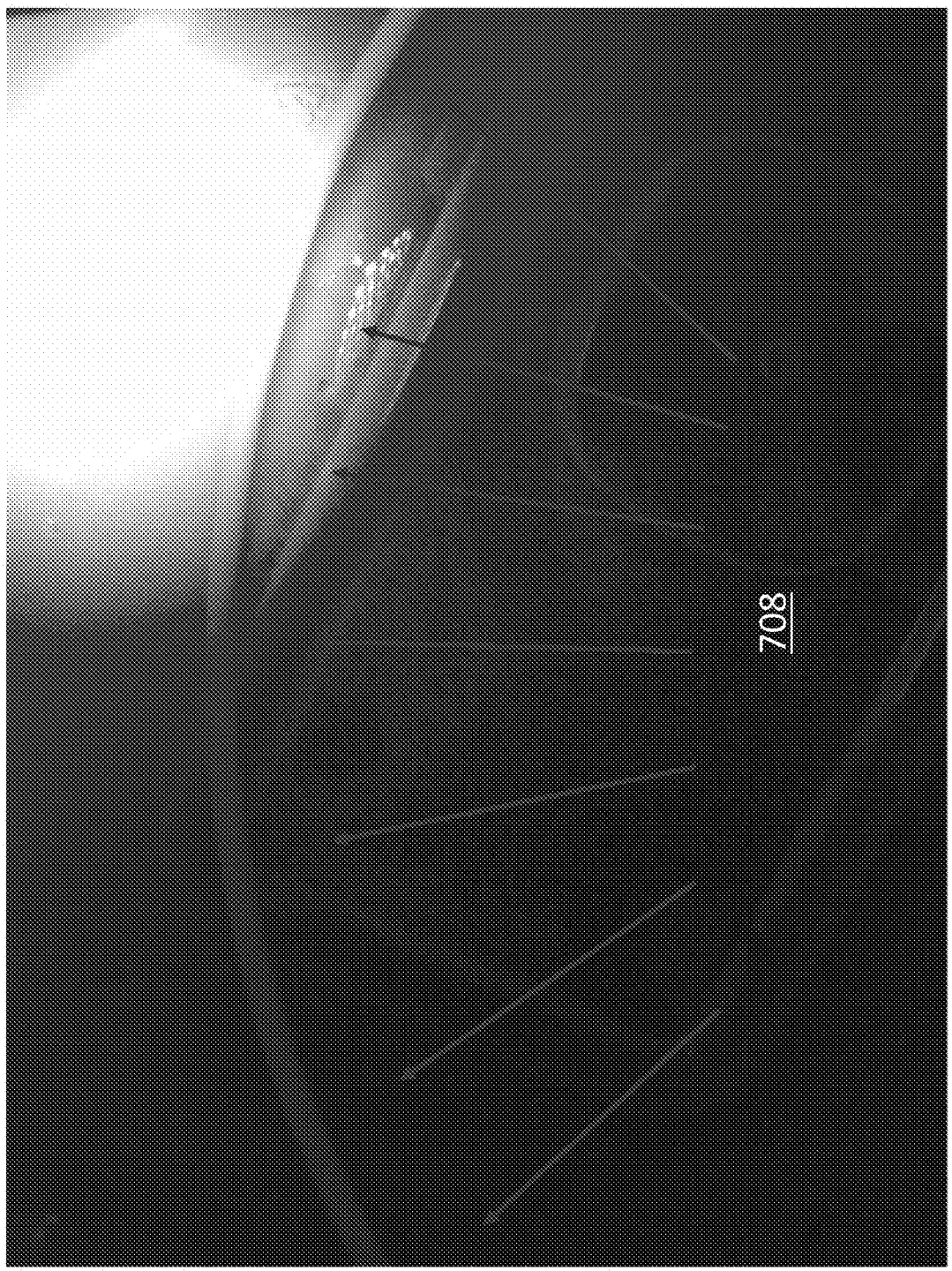
FIG. 29 is a photograph of a black light inspection of the endoscope channel of FIG. 28 after cleaning with a cleaning device disclosed herein.

FIG. 28 also illustrates a photograph of a black light inspection of a contaminated endoscope test channel 700. Egg White and Fluorescent Dye were dried for 3 hours and 30 minutes in the channel. FIG. 29 illustrate a photograph of a black light inspection of the endoscope channel 700 after a single pass of the Venturi TM Endoscope Scope Cleaner. As can be seen, there is no egg white or fluorescent dye present in the channel—it is clean and dry. In addition, the channel contains no residual contamination 708.

EXAMPLE 3

Cleaning the internal channels of a duodenoscope or other endoscope is a critical part of the key manual cleaning steps that must be performed as part of reprocessing a reusable endoscope to safely and effectively return the scope to service. The FDA guidance for this portion of the overall reprocessing process involves testing either an actual scope channel or a representative example using a protein-based soil, preferably with blood. The preferred approach is to infuse the soil into the channel, distribute the soil evenly and then allow the soil to remain until dry or until it reaches a worst-case timeframe. Once at this state, a channel cleaner is passed, the channel is flushed at a level below the level normally used as part of scope reprocessing and then the level of contamination is assessed.

A concentrated protein-based soil with added sheep's blood was prepared by Mycoscience, an independent test lab which prepared and administered the testing. The protein concentration was 19,421 ug/cm2, which is on the high end of the range for duodenoscope channel contamination. A 4.2 mm×180 cm PTFE duodenoscope channel was used for each test. 10 mLs of soil was infused into the test channel, the ends of the channel were capped and the channel was rocked back and forth and rotated to distribute the soil evenly within the test channel. The contaminated test channel was allowed to sit in a container with the ends capped to prevent migration of the soil out of the test channel for two hours. This is double the one hour time limit used by endoscope manufacturers in their reprocessing testing as a worst-case approach.

After the end of the two hour period, the test channel was placed in a container filled with non-enzymatic cleaning detergent at a concentration recommended for endoscope reprocessing. The endoscope test channel was submerged in the detergent, consistent with the endoscope manufacturer's reprocessing instructions and then the scope channel cleaner was advanced through the test channel to clean the contaminated endoscope test channel. Consistent with the FDA's guidelines, detergent was flushed through the endoscope test channel at a substantially reduced level from the amount recommended by the endoscope manufacturer. Next, the endoscope test channel was extracted with 25 mLs of extraction media, and residual protein counts were determined.

The test was performed comparing a Pull Thru™ Endoscope Channel Cleaner, with the Venturi™ Endoscope Channel Cleaner and with a positive control test channel that was extracted without cleaning from a channel cleaner to confirm the level of contamination. The positive control indicated that the level of protein concentration for the test was 19,421 ug/cm2. The Venturi™ Cleaner reduced the level of contamination to 0.08 ug/cm2 in this test. The result for the Pull Thru Cleaner was over 162 percent higher, with the Pull Thru cleaner reducing the level of contamination to 0.13 ug/cm2.

Figure 19:
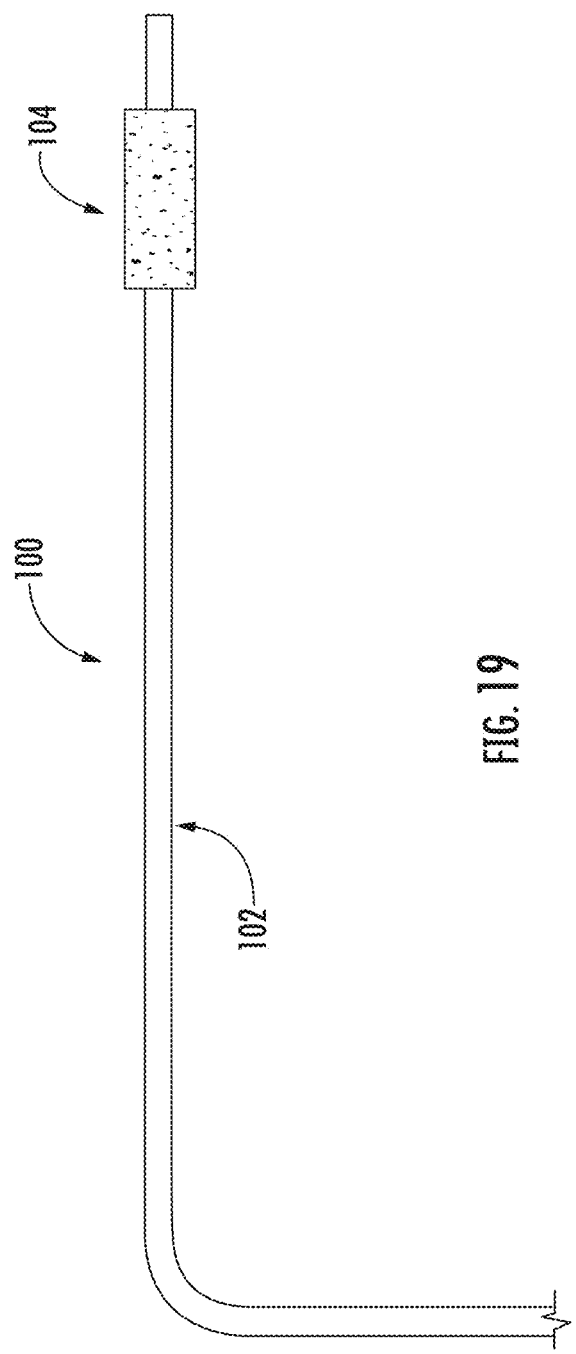
FIG. 19 is a perspective view of an embodiment of a cleaning and/or drying device according to the alternative embodiment.

Referring now to FIG. 19, a cleaning/drying device 100 according to another embodiment includes an elongate shaft 102 and a cleaning member 104 disposed on one portion of shaft 102. Shaft 102 may comprise any suitable material that provides sufficient rigidity for shaft 102 to be advanced through a lumen of an endoscope. Elongate shaft 102 has an outer diameter sized to fit within, and translate through, the internal lumens in endoscope 10. In the exemplary embodiment, shaft 102 will have an outer diameter in the range of about 0.5 to about 5 mm, preferably about 1 to 4 mm.

In certain embodiments, device 100 includes a pull cable configured to withdraw or advance elongate shaft 102 within an internal lumen in endoscope 10. Device may also include an energy source and a motor for advancing and/or withdrawing elongate shaft 102. Of course, it will be recognized that elongate shaft 102 may be manually translated through internal lumen via a proximal handle or suitable actuator (i.e., no motor).

Cleaning/drying member 104 preferably comprises a flexible material that is designed to fit within the internal lumens of an endoscope or other endoscopic instrument and absorb or remove any debris or biomatter that resides within the lumens. As shown, cleaning member/drying 104 has an outer diameter greater than the outer diameter of shaft 102 and is configured to contact the inner surface of a lumen within the endoscope or instrument. Cleaning/drying member 104 comprises a material configured to absorb tissue, biomatter or other debris from at least a portion of an inner surface of the lumen. Removing biomatter, tissue or other debris and moisture eliminates one potential area for pathogens to survive and grow within the instrument.

Cleaning/drying member 104 preferably comprises a material that effectively absorbs biomatter, tissue or other debris and moisture from the internal surfaces of the instruments without creating defects, such as scratches or the like, on these surfaces. This allows the instruments to be reused multiple times without making them progressively more difficult to clean and/or sterilize.

Figure 20:
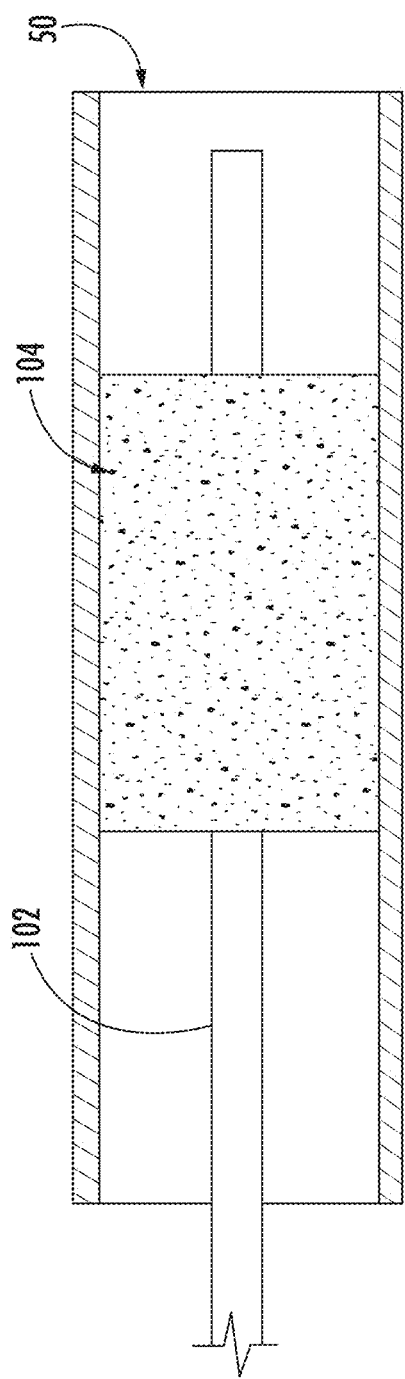
FIG. 20 illustrates use of the cleaning and/or drying device of FIG. 19 within a representative lumen of an endoscopic instrument.

As shown in FIG. 20, cleaning member 104 preferably comprises an expandable material that allows cleaning member 104 to expand from a first position, wherein cleaning member 104 has an outer diameter less than an inner diameter of the lumen 50, to a second position wherein cleaning member 104 has an outer diameter substantially equal to, or greater than, the inner diameter of the lumen 50. In this embodiment, cleaning member 104 may be easily advanced through the lumen 50 and then expanded to contact the internal surfaces 52 of the lumen 50 and absorb biomatter therefrom.

Cleaning/drying member 104 may be expanded through a variety of different means known to those skilled in the art. In an exemplary embodiment, cleaning member 104 is configured to expand upon absorption of a fluid. In this embodiment, cleaning member 104 may be advanced into the lumen in a relatively dry state, and then allowed to absorb fluid therein, such that cleaning/drying member 104 expands to a diameter equal to, or greater than, the inner diameter of the lumen.

Endoscopic instruments may often contain small crevasses, scratches, joints or other irregularities in the internal surfaces of the lumens (see FIG. 3). Cleaning/drying member 104 is preferably configured to expand into these crevasses and irregularities to contact the entire surface therein. In this manner, cleaning member 104 may absorb biomatter, fluid or tissue from within these small crevasses, thereby removing substantially more biomatter from the instruments than conventional cleaning mechanisms.

Cleaning member 104 may comprise any material that absorbs biomatter, fluid or other debris, such as a polymer, foam, sponge, bamboo, hemp, microfibers, cotton or other absorbable fabric or the like. In one embodiment, cleaning member 104 comprises a sponge-like material, such as cellulose, dry, natural and/or compressed cellulose. In an exemplary embodiment, the material comprises a mixture of cellulose and compressed cellulose that allows the sponge to expand when it is hydrated. Preferably, the material is selected such that the sponge has the ability to expand to at least the internal surface of the lumen, while maintaining sufficient absorbability to absorb a volume of material at least equal to the volume of the segment of the lumen that cleaning member 104 occupies.

In the embodiment shown in FIG. 19, cleaning/drying member 104 extends outwardly from one segment of shaft 102 such that cleaning/drying member 104 absorbs biomatter and moisture from the internal surfaces of the lumen as shaft 102 is advanced, or retracted, through the lumen. Alternatively, cleaning/drying device 100 may include more than one cleaning/drying member 104 disposed on different segments of the elongate member (see FIG. 22A). In an exemplary embodiment, the cleaning/drying member(s), alone or in combination, comprise a material configured to absorb a volume of material equal to at least the volume of the lumen.

In certain embodiments, cleaning/drying device 100 further includes a programmable motor (not shown) that may be part of, or separate from, elongate shaft 102. The programmable motor is designed to withdraw shaft 102 from the internal lumen of endoscope 10 at a fixed or variable velocity. Alternatively, the motor may be programmed with a particular algorithm that corresponds to certain cleaning or drying objectives. In one embodiment, the motor is programmed to withdraw elongate shaft 102 at a fixed velocity based on established cleaning or drying times required to completely absorb and remove biomatter from the internal lumen. In an alternative embodiment, the motor is programmed to withdraw elongate shaft 102 in a series of discrete steps, i.e., holding the shaft in place for a specified period of time and then withdrawing it a specified distance and repeating this step until it has been withdrawn and the cleaning or drying procedure is complete.

In an embodiment, elongate shaft 102 is advanced or retracted through a lumen of an endoscopic instrument, such as a biopsy channel 50 of an endoscope 10. The lumen may be filled, or partially filled, with a fluid, such as an enzymatic detergent, or other cleaning fluid. The fluid functions to initially clean and/or disinfect the lumen to remove at least some of the biomatter and other pathogens from the lumen. In addition, the fluid may be absorbed by the sponge, causing the sponge to expand outward to the internal surface of the lumen. In preferred embodiments, the sponge will expand to a diameter greater than the inner diameter of the lumen such that the lumen at least partially constrains the sponge. This ensures that the sponge will expand into any crevasses, cracks or other defects in the walls of the lumen and provides sufficient pressure between the sponge and the internal walls of the lumen to allow the sponge to absorb and/or remove biomatter and fluid from the lumen as elongate shaft 102 is advanced or retracted therethrough.

In one embodiment, the method includes measuring a volume of the lumen and providing a cleaning/drying member configured to absorb an amount of material at least equal to this volume. This ensures that cleaning/drying member 104 completely absorbs all fluid, biomatter, tissue or other debris. The volume of the lumen may be measured with a variety of different methods. In one example, one of the ends of the lumen is sealed such that fluid cannot pass through that end and the opposite end is left open. Fluid is then delivered into the lumen until the lumen is completely full (i.e., any further delivery of fluid results in the fluid spilling out from the open end). The fluid is then emptied into a suitable measuring container to determine the volume of fluid that occupied the lumen.

Once the volume of a target lumen has been measured, a cleaning/drying member 104 is provided that has the capability of absorbing at least the volume of fluid that would fill the lumen. This process can be determined through a variety of different methods. In one example, the cleaning/drying member 104 is dried completely such that it contains substantially no fluid therein. The dried cleaning member 104 or sponge is then placed into a container housing a large volume of fluid that has already been measured. The cleaning member 104 is allowed to absorb fluid until it is completely saturated and the difference in fluid volume in the container provides the maximum absorption capability of the cleaning member.

After cleaning member 104 has been passed through the entire lumen, air is injected into the lumen to purge any remaining disinfectant solution from the lumen and to dry the lumen. Alcohol, such as 70% ethyl or isopropyl alcohol, may be delivered into the lumen to promote drying.

Figure 21B:
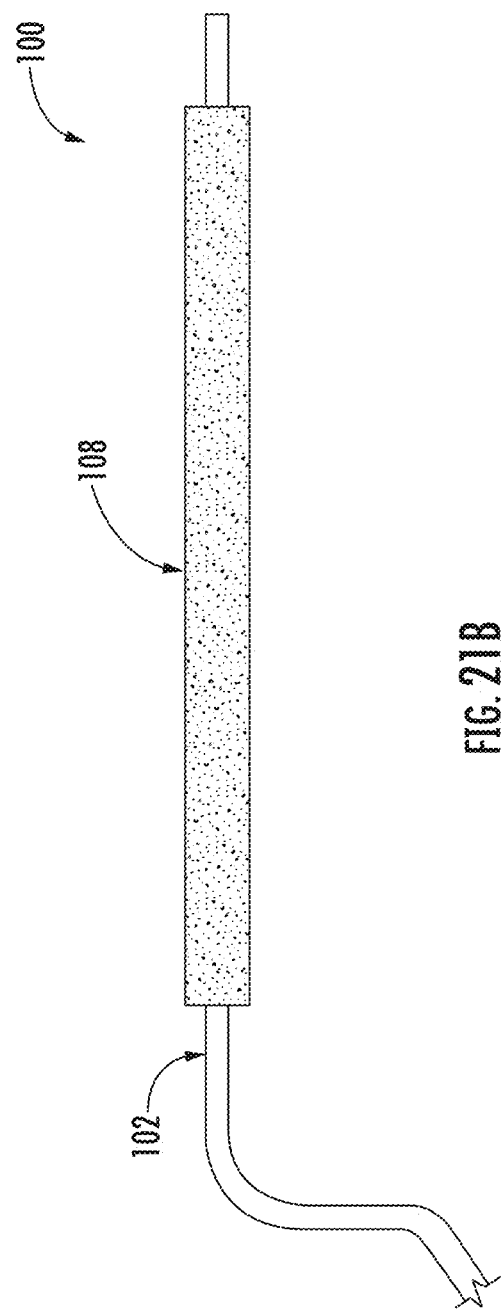

Referring now to FIG. 21B, another embodiment will now be described. As shown, cleaning/drying member 108 extends outwardly from shaft 102 along substantially the entire length of shaft 102, or at least the entire length of the lumen of the endoscopic instrument. In this embodiment, cleaning/drying member 104 has a length substantially equal to or greater than the length of the lumen to be cleaned and dried. Cleaning/drying member 104 preferably comprises a material configured to absorb a volume of material equal to at least the internal volume of the lumen.

Cleaning/drying device 104 may also perform the function of centering elongate shaft 102 within the internal lumen(s) of scope 10. Alternatively, or in addition, shaft 102 may further include a centering device (not shown) at its distal end to keep the cleaning/drying device 104 optimally positioned within the lumen(s) such that the absorption of biomatter is substantially uniform throughout the lumen of the scope 10.

Cleaning device 100 may include one or more sensors (not shown) along shaft 102 for detecting biomatter, pathogens, liquids or other particulate matter within the endoscope 10 or other device. Suitable sensors may include PCT and microarray based sensors, optical sensors (e.g., bioluminescence and fluorescence), piezoelectric, potentiometric, amperometric, conductometric, nanosensors or the like. Shaft 102 may further include an indicator, such as a display, coupled to the sensor(s) and configured to indicator the presence of biomatter pathogens, liquids or other particulars detected by the sensor. The indicator may be any suitable chemical indicator validated for cleaning and/or sterilization procedures that undergoes a physical or chemical change visible to the human eye after exposure to certain parameters. The indicator and sensor may be part of the same device, or separate from each other.

According to another aspect, some embodiments may include the ability to infuse a disinfectant, cleaning chemical or other fluid in advance of the cleaning member 104 or in connection with the absorption of biomatter to additional germicidal effect. The fluid may also serve to lubricate the lumen so it is easier to pull elongate shaft 102 and cleaning member 104 through or for other reasons, including to leave behind a chemistry with a longer half-life for acting as a germicide or for other benefits.

Figure 22:
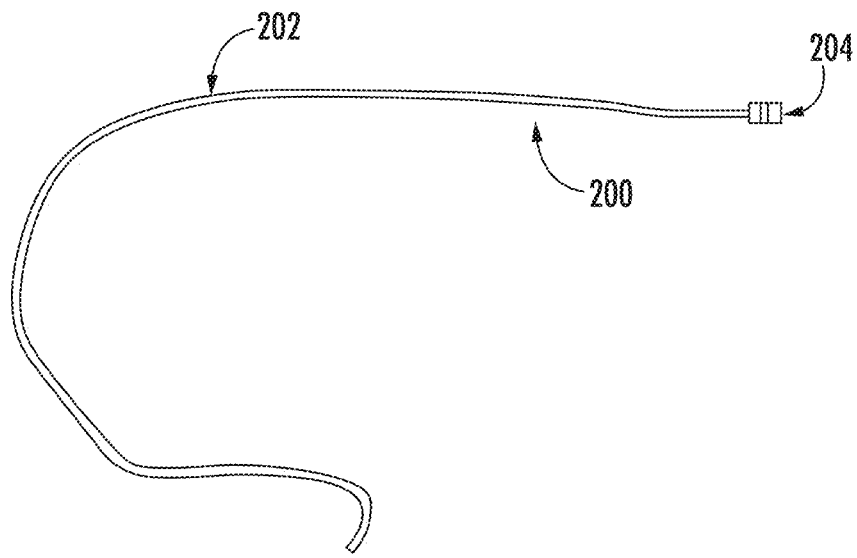
FIG. 22 is a perspective view of another embodiment of a cleaning and/or drying device.
Figure 23:
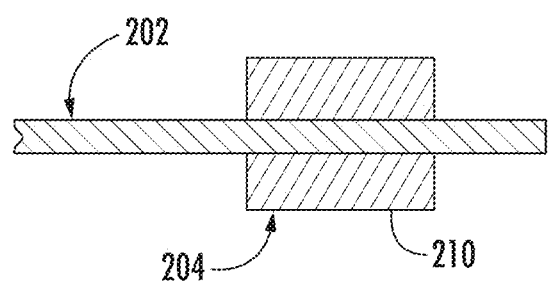
FIG. 23 is a cross-sectional view of a distal end portion of the cleaning and/or drying device of FIG. 22.

Referring now to FIGS. 22 and 23 another embodiment will be described. As shown in FIG. 22, a cleaning/drying device 200 includes an elongate shaft 202 and a cleaning/drying member 204 disposed at a distal end portion of shaft 202. As with the previous embodiment, shaft 202 may comprise any suitable material that provides sufficient rigidity for shaft 202 to be advanced through a lumen of an endoscope. Elongate shaft 202 has an outer diameter sized to fit within, and translate through, the internal lumens in endoscope 10. In the exemplary embodiment, shaft 202 will have an outer diameter in the range of about 0.5 to about 5 mm, preferably about 1 to 4 mm.

Cleaning/drying member 204 has an outer diameter greater than the outer diameter of shaft 202 and is configured to contact the inner surface of the lumen. Cleaning/drying member 204 comprises a material configured to remove tissue, biomatter or other debris from at least a portion of an inner surface of the lumen. Removing biomatter, tissue or other debris and moisture eliminates one potential area for pathogens to survive and grow within the instrument.

Cleaning member 204 preferably comprises a material with a defined degree of roughness such that it effectively removes biomatter, tissue or other debris from the internal surfaces of the instruments without creating defects, such as scratches or the like, on these surfaces. This allows the instruments to be reused multiple times without making them progressively more difficult to clean and/or sterilize.

Cleaning/drying member 204 includes an outer surface 210 comprising a material that is smooth enough to minimize or completely avoid creating any scratches or other defects in the surface of the lumen of the endoscopic instrument. Conventional endoscopes and other endoscopic instruments typically comprise materials with high flexural strength, resistance to water and a low coefficient of friction, such as PTFE, silicone and the like. Thus, outer surface 210 comprises a material that will minimize scratching or otherwise damaging these materials, while still having sufficient durometer and/or roughness to clean the surfaces of these materials of biomatter, tissue and other debris.

In the embodiments described above, cleaning/drying member 204 has a substantially annular cross-sectional shape designed to conform to the circumferential shape of an internal lumen of an endoscopic instrument. However, it will be understood that cleaning/drying member 204 may have a variety of different shapes and configurations. For example, cleaning/drying member 204 may be rectangular, triangular, circular, oval, square and the like. In addition, cleaning/drying member 204 may include surface perturbations, such as projections, bristles, barbs, roughened areas, or the like, to facilitate cleaning/drying of the internal surface of the lumens. However, it will be understood that in embodiments any such perturbations or bristles may be designed from a material similar to the overall cleaning member, or with multiple different materials.

Figure 24:
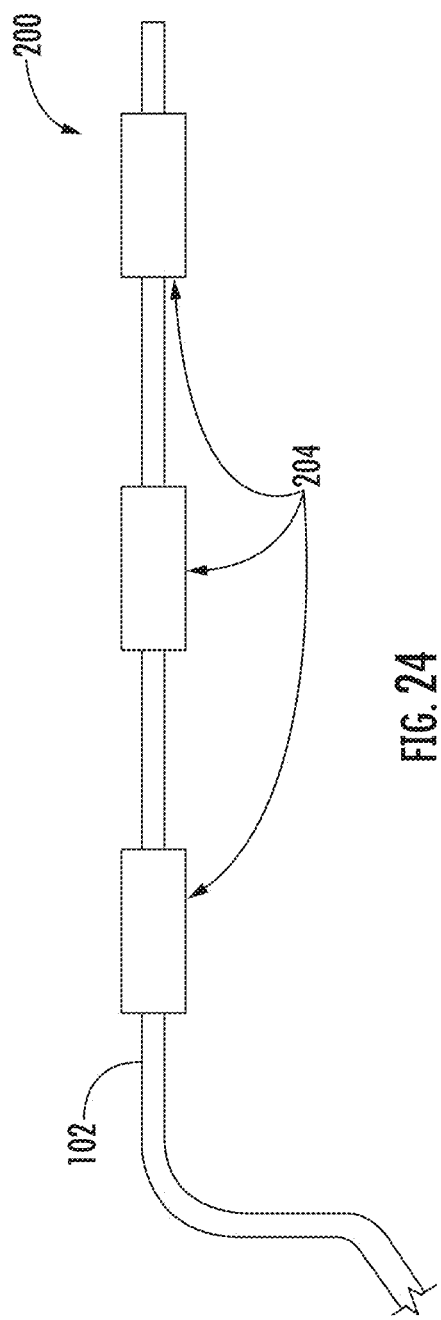
FIG. 24 illustrates another embodiment of a cleaning and/or drying device.

In one embodiment, cleaning/drying member 204 has an outer diameter greater than the outer diameter of shaft 202 and is configured to contact the inner surface of the lumen. Cleaning/drying member 204 may extend outwardly from a distal portion of the shaft 202 such that cleaning/drying member 204 removes biomatter from the internal surfaces of the lumen as the shaft 202 is advanced, or retracted, through the lumen. Alternatively, the device may include more than one cleaning/drying member 204 disposed on different portions of shaft 202, as shown in FIG. 24. In other embodiments, cleaning/drying member 204 extends outwardly from shaft 202 along substantially the entire length of shaft 202, or at least the entire length of the lumen of the endoscopic instrument.

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

While several embodiments of the description have been shown in the drawings, it is not intended that the description be limited thereto, as it is intended that the description be as broad in scope as the art will allow and that the specification be read likewise. Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the description. Accordingly, the present description is intended to embrace all such alternatives, modifications and variances. As well, one skilled in the art will appreciate further features and advantages of the present description based on the above-described embodiments. Accordingly, the present description is not to be limited by what has been particularly shown and described, except as indicated by the appended claims.

What is claimed is:

1. A drying device for use with an endoscopic instrument, the device comprising:
   an elongate member configured for advancement through a lumen within the endoscopic instrument;
   at least one drying member coupled to a portion of the elongate member, wherein the drying member comprises distal and proximal end portions and a central portion between the distal and proximal end portions, wherein the central portion is shaped to create a pressure gradient along the central portion from the distal end portion to the proximal end portion; and first and second cylindrical centering elements positioned on either end of the drying member for centering the drying member as the drying member is advanced through the lumen.

2. The drying device of claim 1, wherein the pressure gradient causes an increase in a relative velocity between the drying member and fluid within the lumen as the drying member is advanced through the lumen.

3. The drying device of claim 1, wherein the pressure gradient causes an increase in shear stress between fluid in the lumen and an internal wall of the lumen.

4. The drying device of claim 1, wherein the drying member is removably coupled to the elongate member.

5. The drying device of claim 1, wherein the at least one drying member is a first drying member, the device further comprising a second drying member coupled to a second portion of the elongate member and a third drying member coupled to the second drying member, wherein the first and second drying members each comprise distal and proximal end portions and a central portion between the distal and proximal end portions and wherein the central portion is shaped to create a pressure gradient along the central portion from the distal end portion to the proximal end portion.

6. The drying device of claim 5, wherein the proximal end portion of the second drying member is coupled to the distal end portion of the first drying member.

7. The drying device of claim 6, further comprising a third cylindrical centering element sized to contact a wall of the lumen, the third cylindrical centering element being positioned on a trailing end of the first and second drying members.

8. A drying device for use with an endoscopic instrument, the device comprising:
    an elongate member configured for advancement through a lumen within the endoscopic instrument;
    at least one drying member coupled to a portion of the elongate member, wherein the drying member comprises distal and proximal end portions and a central portion between the distal and proximal end portions, wherein the central portion is shaped to create a pressure gradient along the central portion from the distal end portion to the proximal end portion; and
    wherein the central portion of the drying member comprises a contraction section coupled to the proximal end portion, a diffusion section coupled to the distal end portion and a throat section coupling the diffusion and contraction sections, wherein the throat section has a diameter less than the diameter of the proximal and distal end portions and greater than a diameter of the diffusion and contraction sections, wherein the contraction section defines an angle with the throat portion that is about 4 degrees to about 85 degrees.

9. The drying device of claim 8, wherein the pressure gradient causes an increase in a relative velocity between the drying member and fluid within the lumen as the drying member is advanced through the lumen.

10. The drying device of claim 8, wherein the pressure gradient causes an increase in shear stress between fluid in the lumen and an internal wall of the lumen.

11. The drying device of claim 8, wherein the contraction section increases in diameter from the proximal end portion to the throat section and the diffusion section decreases in diameter from the throat section to the distal end portion.

12. The drying device of claim 11, wherein the throat section is substantially cylindrical.

13. The drying section of claim 8, wherein the contraction section defines an angle with the throat portion that is about 15 degrees to about 30 degrees.

14. The drying device of claim 8, wherein the diffusion section defines an angle with the throat portion that is about 4 degrees to about 85 degrees.

15. The drying device of claim 8, wherein the drying member is removably coupled to the elongate member.

16. A drying device for use with an endoscopic instrument, the device comprising:
    an elongate member configured for translation through a lumen within the endoscopic instrument;
    at least one drying element coupled to a portion of the elongate member, wherein the drying element comprises distal and proximal end portions and a central portion between the distal and proximal end portions, the central portion having an outer diameter less than the proximal and distal end portions, wherein the central portion is shaped to increase a force applied by a fluid within the lumen against an internal wall of the lumen as the drying element is advanced through the lumen; and
    wherein the force creates a pressure of at least about 100 Pa in at least one area between the distal and proximal end portions of the drying element.

17. The drying device of claim 16, wherein the force creates a shear stress of at least about 5 Pa in at least one area between the distal and proximal end portions of the drying element.

18. The drying device of claim 16, wherein the force creates an average pressure between the proximal and distal end portions of the drying element of at least about 10 Pa.

19. The drying device of claim 16, wherein the central portion has a distance a and the force creates a pressure of at least 50 Pa in at least 25% of the distance between the proximal and distal end portions of the drying element.

20. The drying device of claim 16, wherein the central portion has a distance and the force creates a pressure of greater than 0 Pa in at least 50% of the distance between the proximal and distal end portions of the drying element.

* * * * *